US010369280B2

(12) United States Patent
Nakagami et al.

(10) Patent No.: US 10,369,280 B2
(45) Date of Patent: Aug. 6, 2019

(54) INDWELLING NEEDLE ASSEMBLY

(71) Applicant: NIPRO CORPORATION, Osaka-shi, Osaka (JP)

(72) Inventors: Hiroyuki Nakagami, Osaka (JP); Shingo Sakamoto, Osaka (JP); Asumi Mino, Osaka (JP)

(73) Assignee: NIPRO CORPORATION, Osaka (JP)

( * ) Notice: Subject to any disclaimer, the term of this patent is extended or adjusted under 35 U.S.C. 154(b) by 106 days.

(21) Appl. No.: 15/526,832

(22) PCT Filed: Nov. 20, 2015

(86) PCT No.: PCT/JP2015/082717
§ 371 (c)(1),
(2) Date: Oct. 6, 2017

(87) PCT Pub. No.: WO2016/080525
PCT Pub. Date: May 26, 2016

(65) Prior Publication Data
US 2018/0043093 A1    Feb. 15, 2018

(30) Foreign Application Priority Data

Nov. 21, 2014  (JP) ................................. 2014-236318
Oct. 15, 2015  (JP) ................................. 2014-203436

(51) Int. Cl.
A61M 5/158    (2006.01)
A61M 5/50     (2006.01)
(Continued)

(52) U.S. Cl.
CPC .............. A61M 5/158 (2013.01); A61M 5/50 (2013.01); A61M 25/06 (2013.01);
(Continued)

(58) Field of Classification Search
CPC .......... A61M 25/0014; A61M 25/0017; A61M 25/06; A61M 25/0618; A61M 25/065; A61M 25/0693; A61M 5/158; A61M 5/50
See application file for complete search history.

(56) References Cited

U.S. PATENT DOCUMENTS

2014/0025009 A1    1/2014  Erskine

FOREIGN PATENT DOCUMENTS

EP    2517751 A1    10/2012
JP    4994775 B2     8/2012
(Continued)

OTHER PUBLICATIONS

Feb. 2, 2016 Search Report issued in International Patent Application No. PCT/JP2015/082717.
(Continued)

Primary Examiner — Imani N Hayman
(74) Attorney, Agent, or Firm — Oliff PLC

(57) ABSTRACT

In an indwelling needle assembly, a safety mechanism part is provided with an outer-needle-hub engaging part to be engaged with an outer needle hub, and an engaging-part opposing wall. Relative rotation of the outer-needle-hub engaging part and the engaging-part opposing wall is restricted, and at least one of the outer-needle-hub engaging part and the engaging-part opposing wall displaces integrally with urging parts. When an inner needle is pulled out of the outer needle hub, a block part engaged with the inner needle through an inner-needle engaging part is moved relative to the urging parts and forced to a non-contact state, and the urging parts displace in a direction approaching the inner needle, thereby preventing a needle tip of the inner needle from protruding from the safety mechanism part and releasing engagement of the outer needle hub with the safety mechanism part.

18 Claims, 32 Drawing Sheets

(51) Int. Cl.
    *A61M 25/06* (2006.01)
    *A61M 25/00* (2006.01)
(52) U.S. Cl.
    CPC .... *A61M 25/0618* (2013.01); *A61M 25/0693* (2013.01); *A61M 25/0014* (2013.01); *A61M 25/0017* (2013.01); *A61M 25/065* (2013.01)

(56) References Cited

FOREIGN PATENT DOCUMENTS

| | | |
|---|---|---|
| JP | 2014-517729 A | 7/2014 |
| WO | 2011/154767 A1 | 12/2011 |

OTHER PUBLICATIONS

May 23, 2017 International Preliminary Report on Patentability issued in International Patent Application No. PCT/JP2015/082717.
Sep. 11, 2018 Office Action issued in European Patent Application No. 15861629.2.
Jan. 18, 2019 Search Report issued in European Patent Application No. 15861629.2.
Jun. 10, 2019 Office Action issued in Japanese Patent Application No. 2016-560303.

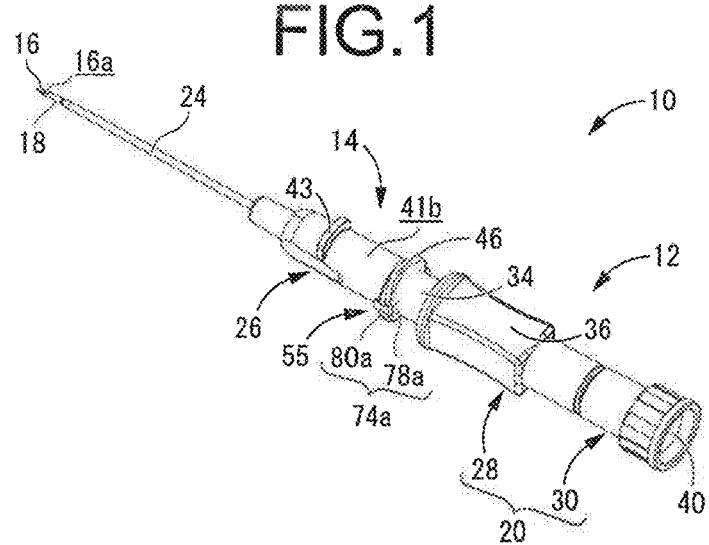
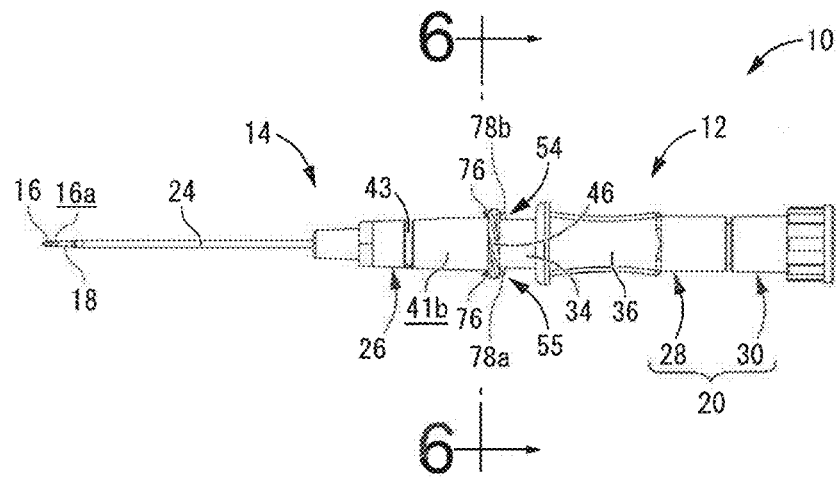
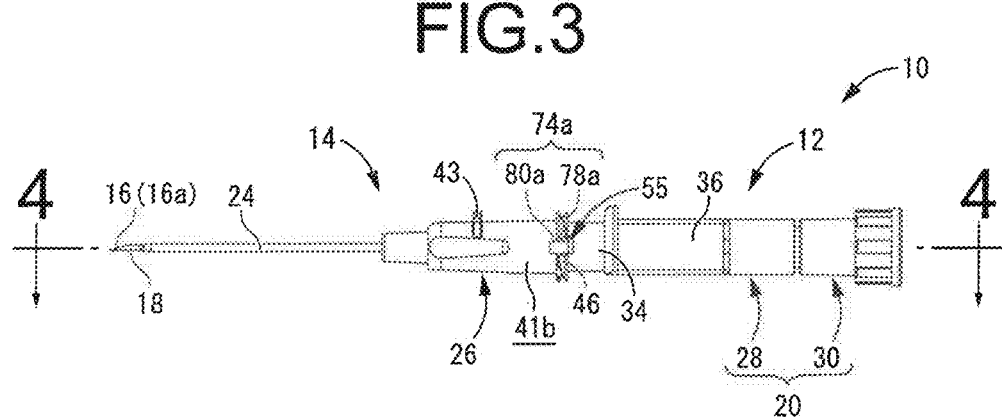

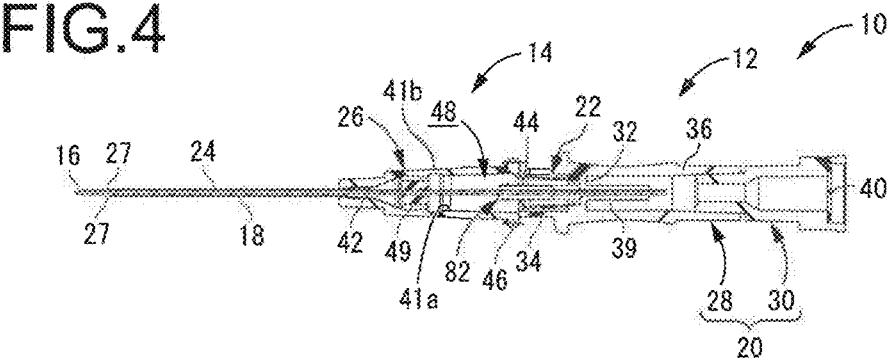
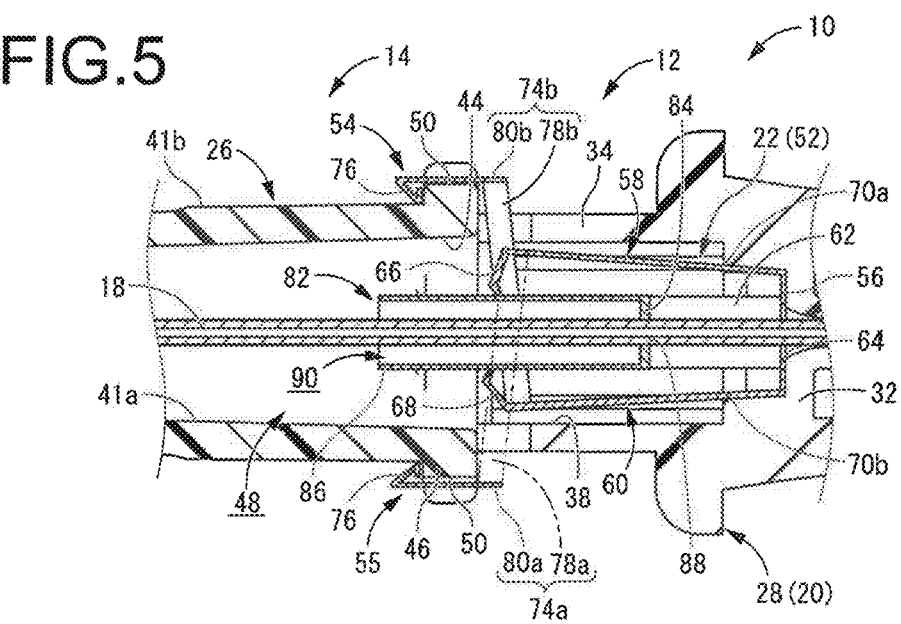
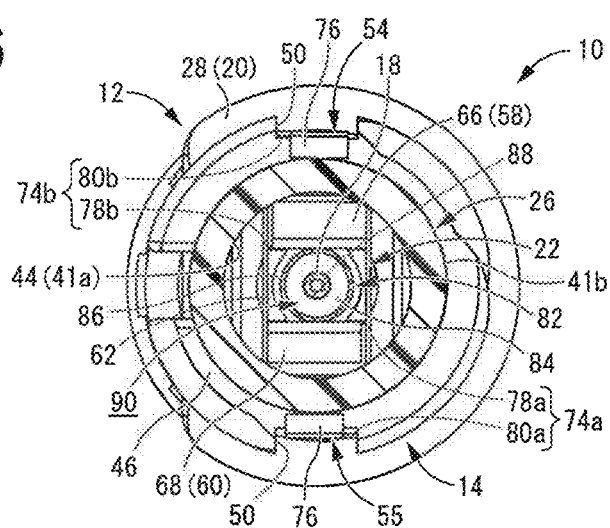

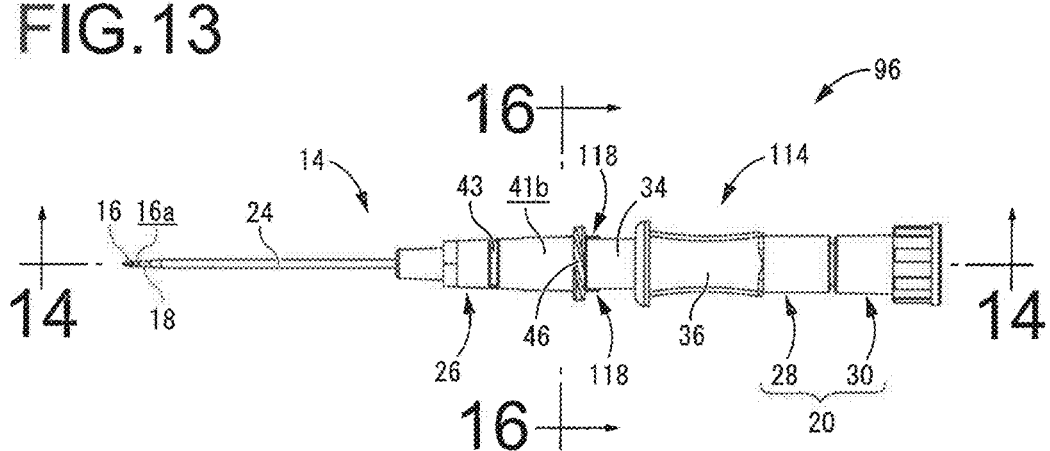

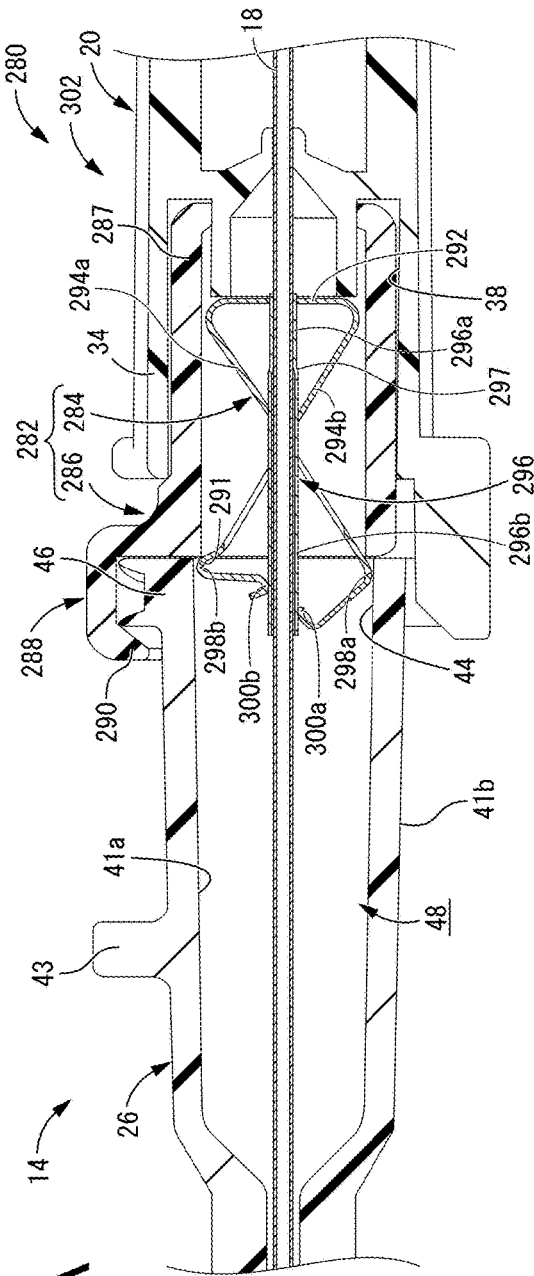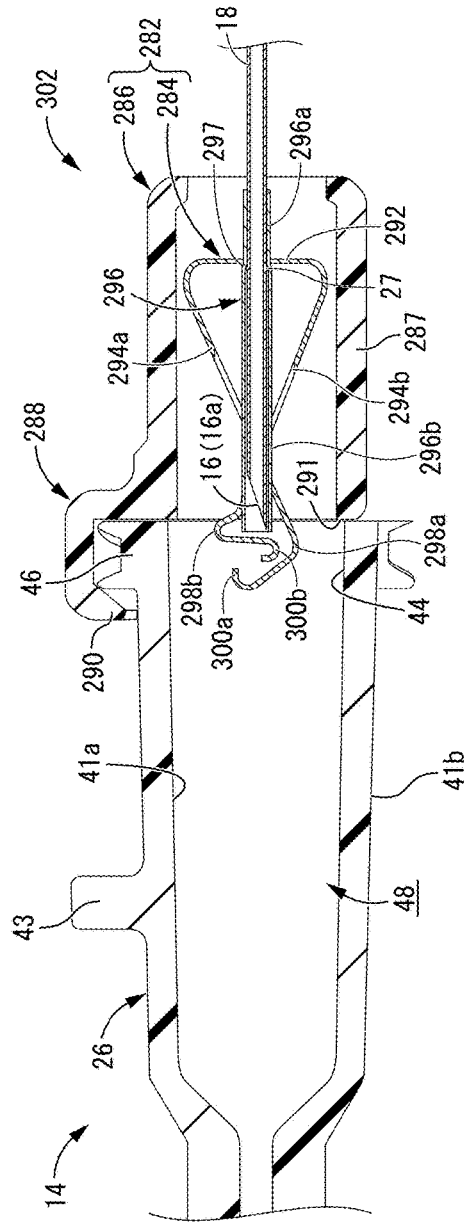
FIG.50A
FIG.50B

INDWELLING NEEDLE ASSEMBLY

TECHNICAL FIELD

The present invention relates generally to an indwelling needle assembly adapted to puncture a blood vessel and to be left therein during fluid transfusion, blood collection, blood dialysis or the like. More particularly, the present invention pertains to an indwelling needle assembly including a needle tip protector for protecting a needle tip of an inner needle after use.

BACKGROUND ART

Conventionally, there is known an indwelling needle assembly in which an inner needle of an inner needle unit is attached so as to pass through an outer needle of an outer needle unit.

When performing fluid transfusion, blood collection, blood dialysis, for example, the indwelling needle assembly is configured to puncture a blood vessel of the patient, and then, by detaching the inner needle unit including the inner needle from the outer needle unit including the outer needle, the outer needle is left in the blood vessel of the patient to be used for treatment.

Meanwhile, with such indwelling needle assembly, in order to prevent inadvertent pricking due to the inner needle of the inner needle unit detached from the outer needle unit after the puncture, it is desirable to mount a needle tip protector for covering the needle tip of the inner needle unit. Accordingly, the specification of U.S. Publication No. US 2014/0025009 (Patent Document 1) and Japanese Patent No. JP-B-4994775 (Patent Document 2) disclose an indwelling needle assembly in which an inner needle unit is inserted into an outer needle unit and an outer-needle-hub engaging part provided to a needle tip protector is engaged with an outer needle hub of the outer needle unit. After the puncture of such indwelling needle assembly, in conjunction with the inner needle being pulled out of the outer needle, the needle tip of the inner needle is configured to be covered by the needle tip protector while engagement of the outer needle hub with the outer-needle-hub engaging part is allowed to be released.

Specifically, the needle tip protector described in these Patent Document 1 and Patent Document 2 is provided with a protection part that covers the needle tip of the inner needle due to pulling out of the inner needle. The protection part is pressed against a sleeve that covers the periphery of the inner needle from the lateral side induced by urging force due to gravity or elastic force. By so doing, when the inner needle is pulled out of the outer needle, the inner needle can be pulled out without directly rubbing against the protection part. This will minimize occurrence of troubles such that when the inner needle is pulled out, the sliding resistance (friction) to the protection part increases and the outer needle is unintentionally pulled out of the skin of the patient together with the inner needle being pulled out.

However, with the needle tip protector described in FIG. 4 etc. of Patent Document 1, a spherical body is adopted as the protection part, and since the spherical body moves due to the gravity, there is a risk that the protection mechanism will not work stably with respect to some orientations for which the indwelling needle assembly is used. Besides, if the spherical body overrides the needle tip of the inner needle or the like, the inner needle will be permitted to move towards the distal end side, posing a risk of the needle tip of the inner needle being exposed again. Moreover, with the needle tip protector described in FIG. 29 etc. of Patent Document 1, there is shown a mode wherein the outer-needle-hub engaging part and the protection part provided to the needle tip protector are opposed to each other sandwiching the peripheral wall of the outer needle hub from the outside and the inside. If the protection part rotates by 90° relative to the outer-needle-hub engaging part from the state shown in FIG. 29 due to external force or the like, for example, the gap between the protection part and the inner surface of the outer needle hub becomes large, and there is a risk that the engagement of the outer-needle-hub engaging part with the outer needle hub will be unexpectedly released before the inner needle is completely pulled out. Furthermore, with the needle tip protector described in FIG. 43 etc. of Patent Document 1, the needle tip protector is inserted in a concave part within the outer needle hub so that the outer needle hub and the needle tip protector are engaged. However, since the concave part is formed within the outer needle hub, dimensional errors are likely to occur, and some dimensional errors cause a risk of insufficient engaging force between the outer needle hub and the needle tip protector. Additionally, since the needle tip protector is inserted in the outer needle hub, in the case where a hemostasis valve or the like is provided to the outer needle hub, it is difficult to obtain enough space for it. This will inevitably increase the size of the outer needle hub.

Also, with the needle tip protector described in Patent Document 2, a coil spring is adopted as an urging member that presses the protection part against the sleeve. This may pose a problem of increase in the number of parts such as the coil spring, and a component for accommodating the coil spring.

BACKGROUND ART DOCUMENTS

Patent Documents

Patent Document 1: US 2014/0025009
Patent Document 2: JP-B-4994775

SUMMARY OF THE INVENTION

Problem the Invention Attempts to Solve

The present invention has been developed in view of the above-described matters as the background, and it is an object of the present invention to provide an indwelling needle assembly with a novel structure which is able to minimize resistance when the inner needle is pulled out, while more effectively preventing the outer needle from being pulled out together with the pulling out of the inner needle.

Means for Solving the Problem

The above and/or optional objects of this invention may be attained according to at least one of the following modes of the invention. The following modes and/or elements employed in each mode of the invention may be adopted at any possible optional combinations.

A first mode of the present invention provides an indwelling needle assembly wherein an inner needle is inserted into an outer needle hub, a safety mechanism part is externally mounted about the inner needle and is configured to protect a needle tip of the inner needle when the inner needle is pulled out of the outer needle hub, the safety mechanism part includes at least one urging part urged in a direction of approaching the inner needle and a block part that is in contact with the urging part such that the urging part is kept remote from the inner needle, the block part includes an inner-needle engaging part that is engaged with the inner needle in an axial direction, and the urging part and the block part are movable relative to each other in a lengthwise direction of the inner needle, the indwelling needle assembly being characterized in that: the safety mechanism part further includes an outer-needle-hub engaging part that is engaged with an outer surface of the outer needle hub and an engaging-part opposing wall that is positioned in opposition to the outer-needle-hub engaging part and limits displacement of the outer needle hub in a direction of disengagement from the outer-needle-hub engaging part by being in contact with the outer needle hub, and relative rotation of the outer-needle-hub engaging part and the engaging-part opposing wall around the inner needle is restricted; at least one of the outer-needle-hub engaging part and the engaging-part opposing wall is configured to displace integrally with the urging part; and by the inner needle being pulled out of the outer needle hub, the block part engaged with the inner needle by the inner-needle engaging part is configured to move relative to the urging part to be in a state of non-contact, while the urging part is configured to displace in the direction of approaching the inner needle such that the needle tip of the inner needle is prevented from protruding from the safety mechanism part and engagement of the outer needle hub with the safety mechanism part is allowed to be released.

With the indwelling needle assembly constructed according to the present mode, the protecting operation of the needle tip of the inner needle by the safety mechanism part and the releasing operation of the engagement with the outer needle by the outer-needle-hub engaging part of the safety mechanism part are in conjunction with the operation for pulling the inner needle out of the outer needle hub. Therefore, when the operation for pulling the inner needle out of the outer needle hub is not performed, namely, before the use of the indwelling needle assembly or the like, engagement effect of the outer needle hub by the outer-needle-hub engaging part is stably exhibited, thereby decreasing the risk of unintentional detachment of the inner needle from the outer needle hub. Besides, when the inner needle is pulled out of the outer needle hub, it is not necessary to separately perform the operation for protecting the needle tip of the inner needle or the operation for releasing the engagement of the safety mechanism part with the outer needle hub. This makes it possible to smoothly perform the pulling-out operation of the inner needle and to promptly realize the protection of the needle tip in conjunction therewith.

In particular, according to the present mode, the block part is provided to the safety mechanism part. Since the block part keeps the urging part remote from the inner needle, the urging part is prevented from directly abutting against the inner needle. Therefore, when the inner needle is pulled out of the outer needle, sliding resistance (friction) due to rubbing between the inner needle and the urging part will be kept to a minimum, thereby avoiding the trouble of the outer needle being pulled out together with the inner needle. In addition, occurrence of noises due to rubbing between the inner needle and the urging part will be effectively prevented as well, so that improved operational feel can be attained.

Moreover, in the present mode, the urging part is urged in the direction of approaching the inner needle, and is not urged by means of gravity as shown in FIG. 4 of Patent Document 1 mentioned above. Thus, the indwelling needle assembly can be used regardless of its orientation. Additionally, in contrast to the urge by means of gravity, the urging part stably displaces, so that the protected state of the inner needle will be kept in a more reliable manner. This makes it possible to effectively avoid troubles such as the needle tip of the inner needle being exposed again.

A second mode of the present invention provides the indwelling needle assembly according to the first mode, wherein the engaging-part opposing wall extends to an inside of the outer needle hub.

With the indwelling needle assembly constructed according to the present mode, the outer-needle-hub engaging part and the engaging-part opposing wall are positioned in opposition to each other sandwiching the peripheral wall of the outer needle hub from the outside and the inside, and also, relative rotation of the outer-needle-hub engaging part and the engaging-part opposing wall around the inner needle is restricted. This makes it possible to decrease a risk that the engaging-part opposing wall unintentionally rotates with respect to the outer-needle-hub engaging part and produces a gap, resulting in unexpected release of the engagement of the outer-needle-hub engaging part with the outer needle hub when the inner needle is pulled out, as shown in FIG. 29 of Patent Document 1. Accordingly, the protecting operation of the needle tip of the inner needle can be improved in accuracy, thereby decreasing a risk of inadvertent pricking as well.

Besides, the engaging-part opposing wall extends to the inside of the outer needle hub. This makes it possible to avoid increased size of the indwelling needle assembly in comparison with the case where the engaging-part opposing wall is provided outside the outer needle hub.

A third mode of the present invention provides the indwelling needle assembly according to the second mode, wherein the engaging-part opposing wall is made of synthetic resin.

With the indwelling needle assembly constructed according to the present mode, the engaging-part opposing wall that extends to the inside of the outer needle hub is made of synthetic resin. This makes it possible to decrease a risk that, for example, the outer needle hub and the engaging-part opposing wall rub against each other and the fragment of the outer needle hub may be inserted into the blood vessel of the patient or the like.

Also, in the present mode, at least a portion of the safety mechanism part is made of synthetic resin. Therefore, in comparison with the case where the entire safety mechanism part is made of metal, it is possible to achieve reduced weight, decreased production cost, improved degree of freedom of shape, or the like.

A fourth mode of the present invention provides the indwelling needle assembly according to the second or third mode, wherein the outer-needle-hub engaging part includes on an inner surface thereof a sloping part that gradually slopes in the direction of approaching the inner needle towards a distal end side in a needle axis direction.

With the indwelling needle assembly constructed according to the present mode, the outer-needle-hub engaging part is configured to displace independently of the urging part. Thus, even if the urging part displaces, the engagement of the outer needle hub with the outer-needle-hub engaging part will not be released. Here, since the sloping part is provided to the inner surface of the outer-needle-hub engaging part, when the inner needle is horizontally pulled out so as to release the engagement of the safety mechanism part with the outer needle hub, the safety mechanism part is also able to undergo sliding movement or rotational movement in the diagonal direction toward the direction of sloping. This can effectively prevent catching of the engaging part and the outer needle hub.

A fifth mode of the present invention provides the indwelling needle assembly according to the first mode, wherein the engaging-part opposing wall is engaged with the outer surface of the outer needle hub.

With the indwelling needle assembly constructed according to the present mode, the outer-needle-hub engaging part and the engaging-part opposing wall are individually engaged with the outer surface of the outer needle hub so that the space inside the outer needle hub can be efficiently obtained. Thus, even if in the case where a hemostasis valve or the like is provided inside the outer needle hub, increase in size of the outer needle hub as shown in FIG. 43 of Patent Document 1 can be avoided.

A sixth mode of the present invention provides the indwelling needle assembly according to the fifth mode, wherein the at least one urging part comprises a pair of urging parts provided in opposition to each other, the outer-needle-hub engaging part continuously extends from one of the urging parts positioned on an opposite side thereof with the inner needle being interposed therebetween, while the engaging-part opposing wall continuously extends from another of the urging parts positioned on an opposite side thereof with the inner needle being interposed therebetween, and by the pair of urging parts displacing in the direction of approaching the inner needle, the outer-needle-hub engaging part and the engaging-part opposing wall are configured to displace with respect to the outer needle hub in a direction of separation from the inner needle such that engagement of the outer-needle-hub engaging part and the engaging-part opposing wall with the outer surface of the outer needle hub is released.

With the indwelling needle assembly constructed according to the present mode, by pulling out the inner needle, the outer-needle-hub engaging part and the engaging-part opposing wall, which are engaged with the outer surface of the outer needle hub, displace so as to be separated from the outer needle hub, whereby their engagement with the outer needle hub can be easily released. In particular, the outer-needle-hub engaging part and the engaging-part opposing wall respectively extend from the pair of urging parts in continuous fashion. Thus, the amounts of displacement of the outer-needle-hub engaging part and the engaging-part opposing wall due to pulling out of the inner needle are approximately equal to that of the urging part. Here, since the urging part is in contact with the block part at the position which is remote from the inner needle, the amount of displacement of the urging part due to the pulling out of the inner needle is greater than that in the case where the urging part and the inner needle are directly in contact with each other. Therefore, according to the present mode, in comparison with the case where the urging part and the inner needle are directly in contact with each other, the amounts of displacement of the outer-needle-hub engaging part and the engaging-part opposing wall can be sufficiently obtained, thereby more stably releasing the engagement of the safety mechanism part with the outer needle hub.

A seventh mode of the present invention provides the indwelling needle assembly according to any of the first through sixth modes, wherein the safety mechanism part further includes an outside tube part in which the urging part is inserted, and one of the outer-needle-hub engaging part and the engaging-part opposing wall is integrally provided with the outside tube part, while another of the outer-needle-hub engaging part and the engaging-part opposing wall is configured to displace integrally with the urging part.

With the indwelling needle assembly constructed according to the present mode, since the urging part is further protected by the outside tube part, the protection of the needle tip of the inner needle can be even more stably attained. By so doing, it is possible to make the structure of the urging part simpler.

An eighth mode of the present invention provides the indwelling needle assembly according to the seventh mode, wherein the outside tube part includes a rotation restricting part that restricts rotation relative to the urging part, and the rotation restricting part restricts the rotation of the outside tube part relative to the urging part while limiting disengagement of the outside tube part from the outer needle hub.

With the indwelling needle assembly constructed according to the present mode, even in the case where the outer-needle-hub engaging part and the engaging-part opposing wall are separately provided, the rotation restricting part makes it possible to easily realize the structure in which relative rotation of the outer-needle-hub engaging part and the engaging-part opposing wall is restricted.

A ninth mode of the present invention provides the indwelling needle assembly according to any of the first through eighth modes, wherein the urging part is made of synthetic resin at least in a portion that is in contact with the block part, and the portion made of synthetic resin is urged by a plate spring in the direction of approaching the inner needle.

With the indwelling needle assembly constructed according to the present mode, at least a portion of the safety mechanism part is made of synthetic resin. Therefore, in comparison with the case where the entire safety mechanism part is made of metal, it is possible to achieve reduced weight, decreased production cost, improved degree of freedom of shape, or the like.

A tenth mode of the present invention provides the indwelling needle assembly according to the ninth mode, wherein the safety mechanism part further includes an urging-part opposing wall that is provided integrally with the urging part and positioned mutually in opposition to the urging part with the inner needle being interposed therebetween, the plate spring is made of metal and has a U-letter shape, the urging part and the urging-part opposing wall have respective guiding grooves on outer surfaces thereof, and distal end portions of the plate spring, which are on an opening side of the plate spring, are inserted into the respective guiding grooves such that the urging part and the urging-part opposing wall are urged in the direction of approaching the inner needle.

With the indwelling needle assembly constructed according to the present mode, the urging means that urges the urging part and the urging-part opposing wall in the direction of approaching the inner needle is provided as a separate element from the urging part and the urging-part opposing wall. Thus, in comparison with the case where the urging part and the urging-part opposing wall have urging force per se, the degree of freedom in designing material, shape, structure or the like of the urging part and the urging-part opposing wall is considerably ensured, and the degree of freedom in setting contact force of the urging part and the urging-part opposing wall against the block part is greatly obtained as well. Therefore, for example, by making the contact force of the urging part and the urging-part opposing wall against the block part larger, it is possible to readily perform tuning such that the urging part and the urging-part opposing wall are even more promptly and reliably displaced in the direction of approaching the inner needle or the like.

Moreover, since the urging force required for displacement of the urging part and the urging-part opposing wall is exhibited by the spring made of metal, desired urging force can be stably obtained. Thus, even if the urging part and the urging-part opposing wall are retained by the block part in the positions remote from the inner needle over an extended period, for example, when the inner needle is pulled out, the urging part and the urging-part opposing wall are able to be stably displaced.

Furthermore, in the present mode, the urging part and the urging-part opposing wall have the respective guiding grooves on their outer surfaces, and the distal end portions of the plate spring having a U-letter shape are attached to the respective guiding grooves. By so doing, attachment of the plate spring to the urging part and the urging-part opposing wall can be made easy.

An eleventh mode of the present invention provides the indwelling needle assembly according to the ninth or tenth mode, wherein the plate spring is made of metal and has a U-letter shape, and distal end portions of the plate spring extend toward a proximal end side in a needle axis direction.

With the indwelling needle assembly constructed according to the present mode, it is possible to attach the plate spring having a U-letter shape to the urging part and the urging-part opposing wall from the distal end side. Thus, the urging part and the urging-part opposing wall can be inserted from the opening side of the plate spring, thereby making the attachment of the plate spring to the urging part and the urging-part opposing wall even easier.

A twelfth mode of the present invention provides the indwelling needle assembly according to any of the first through eleventh modes, wherein the block part has a plate shape.

With the indwelling needle assembly constructed according to the present mode, production of the block part can be easy. Specifically, as the block part, for example, a tubular member disposed externally about the inner needle or the like is conceivable. However, by imparting a plate shape to the block part, the block part will be formed by, for example, the metal flat plate being subjected to press working a plurality of times or the like, thereby making the production of the block part easy.

A thirteenth mode of the present invention provides the indwelling needle assembly according to any of the first through twelfth modes, wherein by the inner needle being pulled out of the outer needle hub, the urging part is configured to displace onto a needle axis of the inner needle such that the needle tip of the inner needle is prevented from protruding from the safety mechanism part.

With the indwelling needle assembly constructed according to the present mode, by pulling out the inner needle, the urging part displaces onto the needle axis of the inner needle so as to prevent the needle tip of the inner needle from protruding, thereby obviating the necessity of separately providing the protection part for protecting the needle tip of the inner needle and the urging part. Therefore, the structure of the safety mechanism part can be made simple without increasing the number of parts as shown in Patent Document 2, while easily realizing the protection mechanism of the needle tip of the inner needle by means of the protection part.

A fourteenth mode of the present invention provides the indwelling needle assembly according to any of the first through thirteenth modes, wherein the urging part includes a needle restricting part that is configured to come into contact with a side surface of the inner needle, and by the inner needle being pulled out of the outer needle hub, the needle restricting part is configured to come into contact with the side surface of the inner needle such that the needle tip of the inner needle is prevented from protruding from the safety mechanism part.

With the indwelling needle assembly constructed according to the present mode, by pulling out the inner needle, the needle restricting part of the urging part comes into contact with the side surface of the inner needle so as to prevent the inner needle from protruding, thereby obviating the necessity of separately providing the needle restricting part for restricting movement of the inner needle and the urging part. Therefore, effects such as prevention of increase in the number of parts, and simplification of the mechanism can be attained the same as the thirteenth mode.

Also, the needle restricting part of the indwelling needle assembly according to the present mode is retained in the position remote from the inner needle. Thus, even if restricting force by the needle restricting part is made large, friction between the inner needle and the needle restricting part never becomes large. This makes it possible to achieve improvement of the restricting force by the needle restricting part and reduction in sliding resistance due to the friction in a compatible manner.

A fifteenth mode of the present invention provides the indwelling needle assembly according to the fourteenth mode, wherein the needle restricting part is configured to be engaged with either one of a convex part and a concave part formed on an outer circumferential surface of the inner needle by the inner needle being pulled out of the outer needle hub.

With the indwelling needle assembly constructed according to the present mode, the convex part or the concave part is provided to the inner needle. Since the convex part or the concave part and the needle restricting part of the urging part become engaged so as to restrict movement of the inner needle, the mechanism for restricting the movement of the inner needle can be easily realized. Note that the engagement of the convex part or the concave part with the needle restricting part may adopt various modes. For example, on the side surface of the inner needle, the needle restricting part of the urging part may be in contact on the distal end side beyond the convex part, or may be inserted into the concave part, or may alternatively be in contact on both the distal end side and the proximal end side beyond the convex part. Besides, the convex part or the concave part may be provided in plurality in the axial direction of the inner needle.

A sixteenth mode of the present invention provides the indwelling needle assembly according to the fourteenth or fifteenth mode, wherein the safety mechanism part further includes a reinforcing part that is configured to limit flexure of the needle restricting part in a position to which the urging part displaces in the direction of approaching the inner needle.

With the indwelling needle assembly constructed according to the present mode, when the inner needle is pulled out, the reinforcing part limits deformation or displacement of the needle restricting part due to flexure. Thus, the inner needle can be stably kept prevented from protruding from the safety mechanism part.

A seventeenth mode of the present invention provides an indwelling needle assembly wherein an inner needle is inserted into an outer needle hub, a safety mechanism part is externally mounted about the inner needle and is configured to protect a needle tip of the inner needle when the inner needle is pulled out of the outer needle hub, the safety mechanism part includes an urging part urged in a direction of approaching the inner needle and a block part that is in contact with the urging part such that the urging part is kept remote from the inner needle, the block part includes an inner-needle engaging part that is engaged with the inner needle in an axial direction, and the urging part and the block part are movable relative to each other in a lengthwise direction of the inner needle, the indwelling needle assembly being characterized in that: the safety mechanism part further includes an outer-needle-hub engaging part that is engaged with an engaging projection provided to an outer surface of the outer needle hub and an engaging-part opposing wall that limits disengaging displacement of the outer-needle-hub engaging part radially outward from the engaging projection by coming into contact with an inner surface of the outer needle hub; an amount of displacement to be limited by the engaging-part opposing wall coming into contact with the inner surface of the outer needle hub is set so as not to reach an amount of displacement required for disengagement of the outer-needle-hub engaging part radially outward from the engaging projection in every axis-perpendicular direction of the outer needle hub; at least one of the outer-needle-hub engaging part and the engaging-part opposing wall is configured to displace integrally with the urging part; and by the inner needle being pulled out of the outer needle hub, the block part engaged with the inner needle by the inner-needle engaging part is configured to move relative to the urging part to be in a state of non-contact, while the urging part is configured to displace in the direction of approaching the inner needle such that the needle tip of the inner needle is prevented from protruding from the safety mechanism part and engagement of the outer needle hub with the safety mechanism part is allowed to be released.

With the indwelling needle assembly constructed according to the present mode, in the initial assembly state, in every axis-perpendicular direction, the permitted amount of displacement of the engaging-part opposing wall is made smaller than the amount of displacement of the outer-needle-hub engaging part required for releasing the engagement of the outer-needle-hub engaging part with the engaging projection provided to the outer surface of the outer needle hub. Thus, even if the engaging-part opposing wall unintentionally rotates with respect to the outer-needle-hub engaging part when the inner needle is pulled out, it is possible to avoid a resultant risk of producing a gap as shown in FIG. 29 of Patent Document 1 and releasing the engagement of the outer needle hub with the outer-needle-hub engaging part. Then, by the inner needle being completely pulled out, the urging part is displaced, so that the remote distance between the outer-needle-hub engaging part and the engaging-part opposing wall becomes greater, which allows the outer needle hub to undergo disengaging displacement through that space. Therefore, the protecting operation of the inner needle by the safety mechanism part can be stably realized.

An eighteenth mode of the present invention provides the indwelling needle assembly according to the seventeenth mode, wherein the engaging-part opposing wall has a curving surface shape in a portion that is configured to come into contact with the inner surface of the outer needle hub.

With the indwelling needle assembly constructed according to the present mode, the portion of the engaging-part opposing wall that is configured to be in contact with the inner surface of the outer needle hub has a curving surface shape. This makes it possible to decrease a risk that, for example, the engaging-part opposing wall and the inner surface of the outer needle hub come into contact and rub against each other so that the fragment of the outer needle hub may be inserted into the blood vessel of the patient or the like.

Effect of the Invention

With the indwelling needle assembly constructed according to the present invention, the urging part that prevents the inner needle from protruding from the safety mechanism part is retained by the block part so as to be remote from the inner needle. Thus, when the inner needle is pulled out, it is possible to keep sliding resistance (friction) between the urging part and the inner needle to a minimum, thereby avoiding the trouble of the outer needle being pulled out together with the inner needle.

BRIEF DESCRIPTION OF THE DRAWINGS

FIG. 1 is a perspective view of an indwelling needle assembly as a first embodiment of the present invention.

FIG. 2 is a top plane view of the indwelling needle assembly shown in FIG. 1.

FIG. 3 is a front view of the indwelling needle assembly shown in FIG. 1.

FIG. 4 is a cross sectional view taken along line 4-4 of FIG. 3.

FIG. 5 is an enlarged view of a principal part of FIG. 4.

FIG. 6 is a cross sectional view taken along line 6-6 of FIG. 2.

FIG. 13 is a top plane view of an indwelling needle assembly as a second embodiment of the present invention.

FIG. 14 is a cross sectional view taken along line 14-14 of FIG. 13.

FIG. 15 is an enlarged view of a principal part of FIG. 14.

FIGS. 30A and 30B are enlarged cross sectional views of a principal part for explaining the operation of the indwelling needle assembly shown in FIG. 20, wherein FIG. 30A illustrates the state before the metal member moves with respect to a resin member, and FIG. 30B illustrates the state of completion of needle-tip protection where the metal member has moved with respect to the resin member.

FIGS. 50A and 50B are vertical cross sectional views of a principal part of an indwelling needle assembly as a seventh embodiment of the present invention, wherein FIG. 50A illustrates the assembly state of the indwelling needle assembly, and FIG. 50B illustrates the state where an inner needle has been pulled out thereof.

EMBODIMENTS FOR CARRYING OUT THE INVENTION

Figure 7:
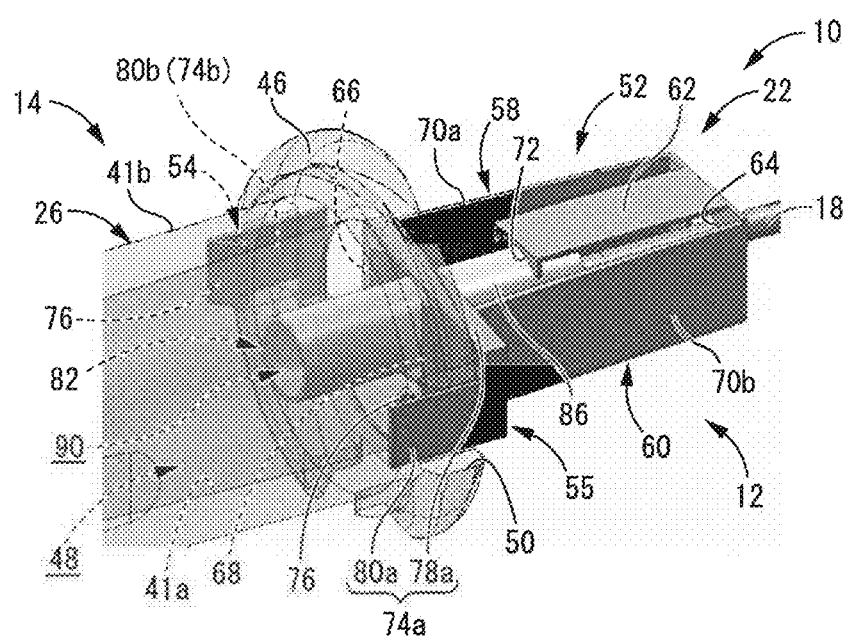
FIG. 7 is a perspective view partially transmitting a principal part of the indwelling needle assembly shown in FIG. 1, which illustrates the state where an inner needle and an inner-needle engaging part of a block part are engaged when the inner needle is pulled out of an outer needle hub.

Embodiments of the present invention will be described below in reference to the drawings.

Referring first to FIGS. 1 to 6, there is depicted an indwelling needle assembly 10 as a first embodiment of the present invention. The indwelling needle assembly 10 includes an inner needle unit 12 and an outer needle unit 14. The inner needle unit 12 includes an inner needle 18 having a needle tip 16, and an inner needle hub 20 provided on the proximal end side of the inner needle 18. Furthermore, a protector 22 serving as a safety mechanism part is externally mounted about the inner needle 18 so as to be movable in the needle axis direction. Meanwhile, the outer needle unit 14 includes an outer needle 24 and an outer needle hub 26 provided on the proximal end side of the outer needle 24, and the inner needle 18 is inserted into the outer needle 24 and the outer needle hub 26. In the description hereinbelow, the axial direction refers to the lateral direction in FIG. 2, in which the inner needle 18 extends. Also, the distal end side or front side refers to the left side in FIG. 2, which is the needle tip 16 side of the inner needle 18, while the proximal end side or rear side refers to the right side in FIG. 2, on which the inner needle hub 20 is positioned with respect to the inner needle 18. Moreover, the upper and lower sides refer to the upper and lower sides in FIG. 3, respectively.

With the inner needle unit 12, the inner needle 18 of the present embodiment is a hollow needle, and is made of publicly known material such as stainless steel, aluminum, titanium, and an alloy of those, for example. The needle tip 16 of the inner needle 18 has a sharp configuration so as to be able to easily puncture a living body. In the present embodiment, since the distal end portion of the inner needle 18 has a needle tip inclined surface 16a inclined with respect to the needle axis direction, the needle tip 16 is made sharp. On the outer circumferential surface of the distal end portion of the inner needle 18, there is provided a large-diameter part 27, whose diametrical dimension is made large and which serves as a convex part as well as an engaging part, about the entire circumference or partially about the circumference (in the present embodiment, the large-diameter part 27 is provided in pairs on opposite sides in one diametrical direction). The inner needle may be a solid needle.

The inner needle hub 20 provided on the proximal end side of the inner needle 18 has a structure in which an inner needle hub main body 28 and a cap 30 are connected in the axial direction. The inner needle hub main body 28 has a roughly tubular shape overall, and includes a partition wall 32 projecting radially inward at the axially medial portion on its inner circumferential surface. Accordingly, with the inner needle hub main body 28, the distal end side beyond the partition wall 32 constitutes a housing tube part 34 while the proximal end side beyond the partition wall 32 constitutes a mounting tube part 36.

The housing tube part 34 has a bottomed tubular shape for which the partition wall 32 is the bottom wall, and includes a housing space 38 opening to the distal end side. Meanwhile, the mounting tube part 36 has a bottomed tubular shape for which the partition wall 32 is the bottom wall, and opens to the proximal end side. On the radially inside of the mounting tube part 36, a fixing tube part 39 is provided concentrically with the mounting tube part 36 so as to extend to the proximal end side from the end face of the proximal end side of the partition wall 32. The proximal end portion of the inner needle 18 is inserted into the inner hole of the fixing tube part 39 and is subjected to a process such as bonding as needed, so that the inner needle 18 is fixed. By so doing, the inner needle 18 is fixed to the inner needle hub 20, and extends to the distal end side beyond the housing tube part 34.

The cap 30 has a stepped round tubular shape overall, and the diameter dimension on the proximal end side is made larger than that on the distal end side. Besides, a ventilation filter 40 is provided to the proximal end opening part of the cap 30. The ventilation filter 40 is characterized by transmitting gas but not liquid. Such ventilation filter 40 is mounted onto the proximal end opening part of the cap 30, and the distal end portion of the cap 30 is press-fitted into the proximal end opening part of the inner needle hub main body 28, thereby liquid-tightly closing the proximal end opening part of the inner needle hub 20, namely the proximal end opening part of the indwelling needle assembly 10.

The inner needle hub main body 28 and the cap 30 that constitute the inner needle hub 20 can be preferably formed of rigid synthetic resin for example, while the ventilation filter 40 can be preferably formed of porous synthetic resin for example. Moreover, by making the inner needle hub 20 transparent, it is possible to confirm flashback of the blood.

With the outer needle unit 14, the outer needle 24 has a tubular shape whose length is shorter than that of the inner needle 18, and the outer circumferential surface of the distal end portion of the outer needle 24 comprises a tapered surface which is gradually made smaller in diameter towards the distal end side. This reduces puncture resistance to the living body. Besides, the inside diameter dimension of the outer needle 24 is made roughly equal to or slightly larger than the outside diameter dimension of the inner needle 18. This enables the inner needle 18 to be inserted into the outer needle 24. There may be provided one or more passage holes on the peripheral wall of the distal end portion of the outer needle 24, which makes it possible to improve flowing efficiency of the fluid with respect to the outer needle 24. Such outer needle 24 can be preferably formed of soft synthetic resin, for example.

Moreover, the outer needle hub 26 has a roughly tubular shape overall, and extends in the axial direction. With the outer needle hub 26, an inner surface 41a and an outer surface 41b are made larger in diameter on the proximal end side rather than on the distal end side, so that the inside diameter dimension of the distal end portion of the outer needle hub 26 is roughly equal to the outside diameter dimension of the outer needle 24. To the inner surface 41a of the distal end portion of the outer needle hub 26, a roughly tubular caulking pin 42 is secured. The proximal end portion of the outer needle 24 is inserted radially between the caulking pin 42 and the outer needle hub 26, and is subjected to a process such as bonding as needed, so that the outer needle 24 extends from the distal end of the outer needle hub 26. Such caulking pin 42 can be preferably formed of metal or the like for example, thereby improving strength of the connected section of the outer needle hub 26 and the outer needle 24. Furthermore, on the outer surface 41b of the outer needle hub 26, a projecting operation piece 43 is integrally formed so as to project upward in FIG. 3. As will be described later, this makes it easy to press the outer needle hub 26 by a finger so as to retain the outer needle 24 in the puncture state when pulling the inner needle 18 out of the outer needle 24.

In addition, with the proximal end opening part 44 of the outer needle hub 26, a flange part 46 serving as an engaging projection is provided to the outer surface 41b of the outer needle hub 26 so as to project radially outward. The inside diameter dimension of the proximal end opening part 44 of the outer needle hub 26 is made roughly equal to the inside diameter dimension of the housing tube part 34. Accordingly, with the inner needle unit 12 and the outer needle unit 14 assembled as will be described later, an inside area 48 of the outer needle hub 26 and the housing space 38 of the housing tube part 34 communicate with each other in the axial direction. In the inside area 48 of the outer needle hub 26, there is provided a disk-shaped hemostasis valve 49 formed of a rubber elastic body or elastomer. Thus, when the inner needle unit 12 is attached, the hemostasis valve 49 is perforated by the inner needle 18, and when the inner needle 18 is removed, the hemostasis valve 49 closes so as to block the distal end side beyond the hemostasis valve 49 from the outside.

Furthermore, on the outer circumferential surface of the flange part 46, there are provided engaging grooves 50 partially along the circumference so as to extend in the axial direction. In the present embodiment, a pair of engaging grooves 50, 50 are provided on opposite sides in one diametrical direction (on both the upper and lower sides in FIG. 4), and in other words, the outside diameter dimension of the flange part 46 is made small at the portion where the engaging grooves 50, 50 are provided. On the outer circumferential surface of the flange part 46, a screw thread is provided at the portion away from the engaging grooves 50, 50, so that a luer-lock type syringe, connector or the like is connectable to the outer needle hub 26 after the outer needle 24 is indwelled.

Such outer needle hub 26 can be preferably formed of rigid synthetic resin for example, the same as the inner needle hub 20.

Additionally, the protector 22 is externally mounted about the inner needle 18 of the inner needle unit 12 attached to the outer needle unit 14, and the protector 22 is configured to protect the needle tip 16 of the inner needle 18 pulled out of the outer needle hub 26. The protector 22 includes a protector main body 52, and an outer-needle-hub engaging part 54 and an engaging-part opposing wall 55 are integrally provided to the protector main body 52. When the inner needle unit 12 and the outer needle unit 14 are attached, the outer-needle-hub engaging part 54 is engaged with the outer surface 41b of the outer needle hub 26. The engaging-part opposing wall 55 is positioned in opposition to the outer-needle-hub engaging part 54. Therefore, in the present embodiment, relative rotation of the outer-needle-hub engaging part 54 and the engaging-part opposing wall 55 around the inner needle 18 is restricted. Such protector 22 can be formed by cutting out a blank metal plate in a prescribed shape and performing press working a plurality of times or the like, or can also be formed of synthetic resin or the like.

The protector main body 52 has a roughly square tubular shape with a bottom overall, namely, with a rectangular bottom wall 56. On the outer peripheral end of the bottom wall 56, four plate bodies are formed so as to extend from the respective four sides to the distal end side. That is, on opposite sides in one diametrical direction (the vertical direction in FIG. 5), an upper plate part 58 and a lower plate part 60 serving as a pair of urging parts are positioned in opposition. Meanwhile, in the direction which is orthogonal to the direction of opposition of these upper and lower plate parts 58, 60 (the vertical direction in FIG. 3), a pair of side plate parts 62, 62 are positioned in opposition. Besides, a passage hole 64 perforates the center of the bottom wall 56 in the axial direction.

Moreover, the distal end portions of the upper and lower plate parts 58, 60 are bent in a hooked form inward in the direction of opposition, so that the hooked bent portions respectively constitute upper and lower contact parts 66, 68 for contacting and fixing a housing sleeve 82 (a block part) described later. That is, the upper and lower plate parts 58, 60 include respective straight parts 70a, 70b that straightly extend from the bottom wall 56, and the respective contact parts 66, 68 bent in a hooked form are provided to the distal ends of the straight parts 70a, 70b. The axial dimension of the side plate parts 62, 62 is made smaller than that of the upper and lower plate parts 58, 60. The distal ends of the side plate parts 62, 62 are bent inward in the direction of opposition thereof, with respective concave parts 72, 72 provided so as to curve along a peripheral wall 86 of the housing sleeve 82 described later (see FIG. 7).

To the distal end portion of the protector main body 52, the engaging-part opposing wall 55 and the outer-needle-hub engaging part 54 are provided. The engaging-part opposing wall 55 and the outer-needle-hub engaging part 54 are provided to the upper plate part 58 and the lower plate part 60 respectively, and the engaging-part opposing wall 55 and the outer-needle-hub engaging part 54 comprise respective arm parts 74a, 74b and locking claws 76, 76. Furthermore, the arm parts 74a, 74b comprise respective upper arm parts 78a, 78b and forearm parts 80a, 80b. Specifically, the forearm parts 80a, 80b are positioned further on the distal end side than the upper and lower plate parts 58, 60, and are positioned in opposition to each other in the same direction as the direction of opposition of the upper and lower plate parts 58, 60 (the vertical direction in FIG. 5), so as to extend roughly in the axial direction. The proximal end portions of the forearm parts 80a, 80b are connected to the respective distal end portions of the straight parts 70a, 70b of the upper and lower plate parts 58, 60 by the upper arm parts 78a, 78b. Here, the forearm part 80a on the lower side in FIG. 5 and the upper plate part 58 are connected to each other with the respective side surfaces bridged by the upper arm part 78a (illustrated by a chain double-dashed line in FIG. 5). Meanwhile, the forearm part 80b on the upper side in FIG. 5 and the lower plate part 60 are connected to each other with the respective side surfaces bridged by the upper arm part 78b. Therefore, the upper arm parts 78a, 78b are in opposition to each other in the direction orthogonal to the direction of opposition of the forearm parts 80a, 80b (the vertical direction in FIG. 3), and intersect each other in plan view. In other words, the upper arm parts 78a, 78b, which extend from the distal end portions of the upper and lower plate parts 58, 60, extend outward in the direction of opposition of the upper and lower plate parts 58, 60 while intersecting each other in plan view.

Figure 11:
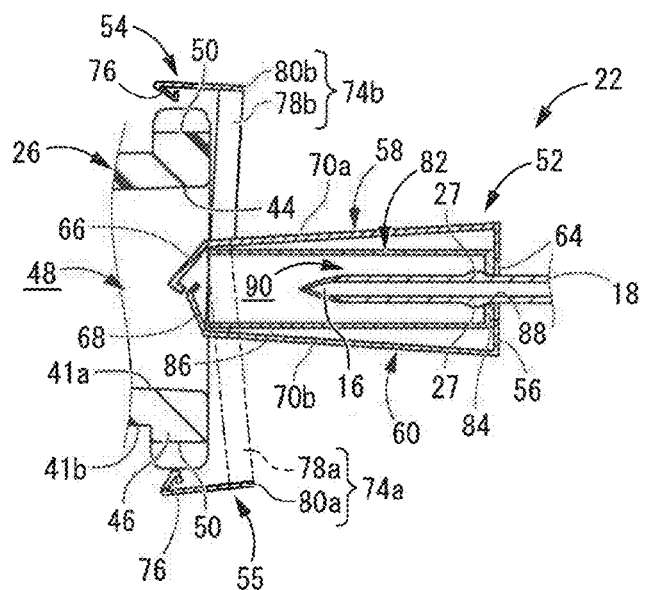
FIG. 11 is an enlarged view of a principal part of FIG. 10.

As shown in FIG. 11 described later, if the protector main body 52 does not clasp the housing sleeve 82, namely the protector 22 is in a free state, the straight part 70a of the upper plate part 58 and the forearm part 80a are roughly parallel to each other, and the upper arm part 78a that connects the straight part 70a and the forearm part 80a is roughly orthogonal to the straight part 70a and the forearm part 80a. Meanwhile, the straight part 70b of the lower plate part 60 and the forearm part 80b are roughly parallel to each other, and the upper arm part 78b that connects the straight part 70b and the forearm part 80b is roughly orthogonal to the straight part 70b and the forearm part 80b.

Moreover, the distal end portions of the forearm parts 80a, 80b are bent inward in the direction of opposition so as to provide the respective locking claws 76, 76.

The protector 22 having the above-described shape is externally mounted about the inner needle 18 of the inner needle unit 12. Accordingly, the upper and lower plate parts 58, 60 and the pair of side plate parts 62, 62 extend from the bottom wall 56 to the distal end side along the side of the inner needle 18. That is, the upper and lower plate parts 58, 60 serving as the urging parts are provided in pairs so as to sandwich the inner needle 18. Besides, the respective upper arm parts 78a, 78b of the engaging-part opposing wall 55 and the outer-needle-hub engaging part 54 extend in the direction of contact of the upper and lower contact parts 66, 68 with the housing sleeve 82 as far as the diametrically opposite sides of the upper and lower contact parts 66, 68 beyond the inner needle 18. That is, the outer-needle-hub engaging part 54 continuously extends from the lower plate part 60 which serves as the urging part and is positioned on the opposite side thereof with the inner needle 18 being interposed therebetween. Meanwhile, the engaging-part opposing wall 55 continuously extends from the upper plate part 58 which serves as the urging part and is positioned on the opposite side thereof with the inner needle 18 being interposed therebetween.

Here, with the inner needle 18, the proximal end side beyond the large-diameter parts 27, 27 is inserted into the passage hole 64 of the bottom wall 56 of the protector main body 52. Therefore, as to the inner needle 18, the portion between the large-diameter parts 27, 27 and the portion secured to the inner needle hub 20 is an inserted portion of the inner needle 18 into the protector 22. Furthermore, the housing sleeve 82 serving as the block part is externally mounted about the inserted portion of the inner needle 18 into the protector 22. Accordingly, the inner needle unit 12 includes the housing sleeve 82.

The housing sleeve 82 has an approximately round tubular shape with a bottom. Specifically, the housing sleeve 82 includes a circular bottom wall 84 serving as an inner-needle engaging part, and a peripheral wall 86 extending from the outer peripheral end of the bottom wall 84 to the distal end side. The outside diameter dimension of the bottom wall 84 of the housing sleeve 82 is made larger than the inside diameter dimension of the passage hole 64 of the bottom wall 56 of the protector main body 52. Besides, a passage hole 88 perforates the center of the bottom wall 84 in the axial direction. The inside diameter dimension of the passage hole 88 is made roughly equal to or slightly larger than the outside diameter dimension of the inner needle 18, while being made smaller than the outside diameter dimension of the inner needle 18 at the large-diameter parts 27, 27. The axial dimension of the housing sleeve 82 is made smaller than the axial dimension of the straight parts 70a, 70b of the protector main body 52 when the protector 22 is in a free state. In addition, there is provided a prescribed remote distance between the concave parts 72, 72 at the distal ends of the side plate parts 62, 62 and the peripheral wall 86 of the housing sleeve 82 in the radial direction. Owing to such side plate parts 62, 62, the housing sleeve 82 can be prevented from largely deviating in the direction of opposition of the side plate parts 62, 62 by the peripheral wall 86 and the concave part 72 coming into contact with each other. Meanwhile, since the peripheral wall 86 and the concave parts 72, 72 are remote from each other by a prescribed distance, resistance or noise due to friction will not be generated during movement of the housing sleeve 82 in the axial direction.

Furthermore, the inside diameter dimension of the peripheral wall 86 is made sufficiently larger than the outside diameter dimension of the inner needle 18. By the housing sleeve 82 having such configuration being externally mounted about the inner needle 18 of the inner needle unit 12, there is provided a gap 90 radially between the peripheral wall 86 and the inner needle 18.

The indwelling needle assembly 10 of the present embodiment is constituted by the inner needle 18 of the inner needle unit 12 being inserted into the outer needle unit 14 of the above-described configuration. Specifically, with the inner needle unit 12 of the indwelling needle assembly 10, in the initial state shown in FIGS. 1 to 6, the proximal end of the inner needle 18 is fixed to the inner needle hub 20 and the inner needle 18 extends from the inner needle hub 20 to the distal end side, while the proximal end side of the inner needle 18 beyond the large-diameter parts 27, 27 is inserted into the passage hole 64 of the bottom wall 56 of the protector main body 52. In other words, the proximal end of the inner needle 18 passes through the protector main body 52 and is fixed to the inner needle hub 20. In the initial state, the protector main body 52 is positioned within the housing space 38 of the housing tube part 34 of the inner needle hub main body 28, while the distal end portions of the outer-needle-hub engaging part 54 and the engaging-part opposing wall 55 project to the distal end side beyond housing space 38.

Moreover, to the inserted portion of the inner needle 18 into the protector 22, there is provided the housing sleeve 82. Specifically, the proximal end side of the inner needle 18 is inserted into the passage hole 88 of the bottom wall 84 of the housing sleeve 82. At that time, the peripheral wall 86 of the housing sleeve 82 is clasped and retained between the upper and lower contact parts 66, 68 from both sides. When the protector main body 52 does not clasp the housing sleeve 82, namely the protector 22 is in a free state, the upper and lower contact parts 66, 68 overlap each other when viewed in the axial direction and seem to deviate in the axial direction (see FIG. 11). That is, by the housing sleeve 82 being clasped between the upper and lower contact parts 66, 68, the upper and lower contact parts 66, 68 and the distal end portions of the straight parts 70a, 70b continuously extending from the contact parts 66, 68 are pushed to be elastically expand outward in the direction of opposition, to be elastically deformed. In other words, in the initial state shown in FIGS. 1 to 6, the peripheral wall 86 of the housing sleeve 82 is subjected to elastic recovery force, namely urging force, by the upper and lower contact parts 66, 68 inward in the direction of opposition (the direction of approaching the inner needle 18). Thus, displacement of the upper and lower plate parts 58, 60 in the direction of approaching the inner needle 18 is limited by the upper and lower contact parts 66, 68 being in contact with the housing sleeve 82. Consequently, the upper and lower plate parts (the urging parts) 58, 60, and the upper and lower contact parts 66, 68 provided to the distal ends of the upper and lower plate parts 58, 60 are kept in positions remote from the inner needle 18. Accordingly, due to such urging force, the housing sleeve 82 is positioned to be fixed to the protector main body 52 in the axial direction.

In the initial state, the upper and lower contact parts 66, 68 clasp the roughly same axial position in the axially medial portion of the housing sleeve 82, and the distal end portion of the housing sleeve 82 extends to the distal end side beyond the housing space 38. Besides, since the housing sleeve 82 is clasped between the upper and lower contact parts 66, 68, the straight parts 70a, 70b slope with respect to the axial direction so as to expand outward in the direction of opposition toward the distal end. The upper arm parts 78a, 78b that are roughly orthogonal to the respective straight parts 70a, 70b extend from the distal ends of the respective straight parts 70a, 70b so as to slope to the distal end side going outward in the direction of opposition. At the distal end edge of the housing tube part 34, cut-out side holes are formed, and the upper arm parts 78a, 78b pass the respective side holes. The shape of the distal end edge of the housing tube part 34 is appropriately changeable, and for example, the shape that covers the outer surface of the locking claw 76 may be acceptable.

The outer needle unit 14 is externally placed about the inner needle 18 of the inner needle unit 12 having the above-described configuration. In other words, the inner needle 18 is inserted from the proximal end opening part 44 of the outer needle hub 26, so that the needle tip 16 of the inner needle 18 projects from the distal end side of the outer needle 24. At that time, the distal end surface of the inner needle hub main body 28 of the inner needle hub 20 is in contact with the end face of the proximal end side of the outer needle hub 26. By so doing, the housing space 38 and the inside area 48 communicate with each other, and the distal end portion of the housing sleeve 82 is inserted within the inside area 48. Besides, the engaging grooves 50, 50 formed on the outer circumferential surface of the flange part 46 on the outer surface 41b of the outer needle hub 26 and the locking claws 76, 76 respectively provided to the engaging-part opposing wall 55 and the outer-needle-hub engaging part 54 are aligned in the circumferential direction, so that the locking claws 76, 76 are locked with respect to the end face of the distal end side of the flange part 46 via the engaging grooves 50, 50. Accordingly, the engaging-part opposing wall 55 and the outer-needle-hub engaging part 54 are engaged with the outer surface 41b of the outer needle hub 26, so that the protector 22 and the outer needle hub 26 are positioned in the axial direction. Here, the forearm parts 80a, 80b extend in the roughly axial direction. Also, between the engaging-part opposing wall 55 and the outer surface 41b (the flange part 46) of the outer needle hub 26, there may be provided a clearance to a slight extent such that the engagement of the outer needle hub 26 and the outer-needle-hub engaging part 54 will not be released. By the engaging-part opposing wall 55 and the outer surface 41b (the flange part 46) of the outer needle hub 26 being in contact with each other, displacement of the outer-needle-hub engaging part 54 in the direction of disengagement from the outer needle hub 26 is limited.

Operation of the indwelling needle assembly 10 of the present embodiment constructed in the above manner in use will be described hereinbelow while indicating in FIGS. 7 to 12.

First, the blood vessel of the patient is punctured by the indwelling needle assembly 10 in the initial state as depicted in FIGS. 1 to 6. Then, as depicted in FIGS. 7 to 10, with the outer needle 24 kept inserted in the blood vessel of the patient, the inner needle 18 is pulled out of the outer needle 24 to the proximal end side. By so doing, the outer needle 24 is indwelled while being kept inserted in the blood vessel of the patient.

Figure 8:
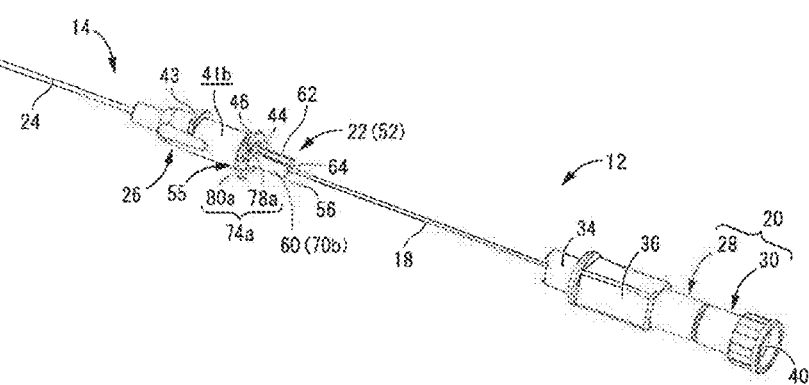
FIG. 8 is a perspective view corresponding to FIG. 1, which is suitable for explaining the state where, with the indwelling needle assembly shown in FIG. 1, the inner needle is pulled out of the outer needle hub and engagement by an outer-needle-hub engaging part is released.
Figure 9:
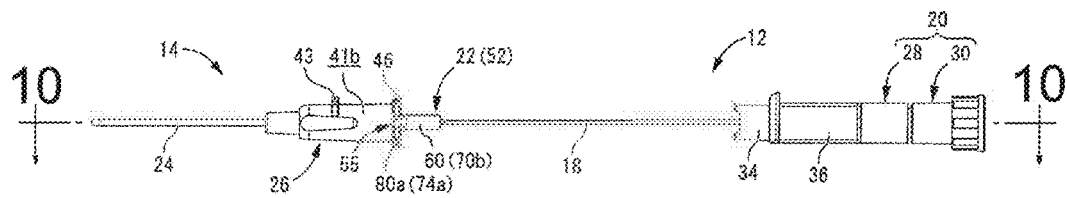
FIG. 9 is a front view of the indwelling needle assembly shown in FIG. 8.
Figure 10:
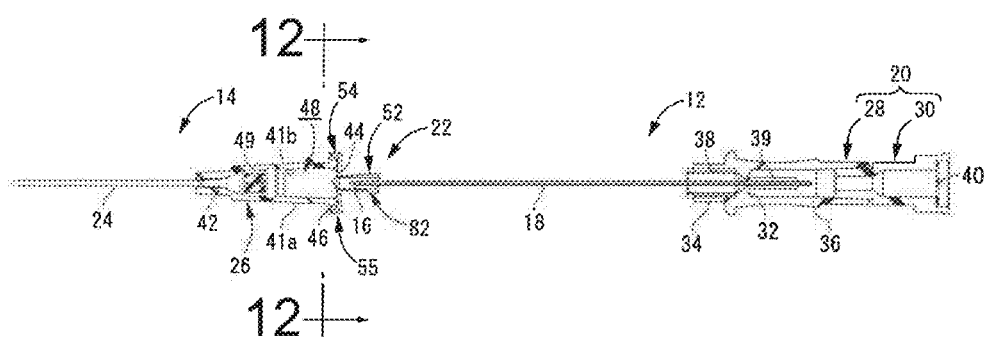
FIG. 10 is a cross sectional view taken along line 10-10 of FIG. 9.

Here, the passage hole 88 of the bottom wall 84 of the housing sleeve 82 has the inside diameter dimension smaller than the outside diameter dimension of the large-diameter parts 27, 27. Thus, by the inner needle 18 being pulled out to the proximal end side, as shown in FIG. 7, the large-diameter parts 27, 27 of the inner needle 18 and the bottom wall 84 of the housing sleeve 82 serving as the inner-needle engaging part are engaged in the axial direction. In this state, as depicted in FIGS. 8 to 10, by the inner needle 18 being pulled out further to the proximal end side, the housing sleeve 82 will be pulled together with the inner needle 18 to the proximal end side with respect to the protector 22. In the present embodiment, the axial dimension of the housing sleeve 82 is made larger than the axial dimension from the large-diameter parts 27, 27 to the needle tip 16 of the inner needle 18. Therefore, in the state where the large-diameter parts 27, 27 of the inner needle 18 and the bottom wall 84 of the housing sleeve 82 are engaged, the outer circumference of the inner needle 18 is covered by the peripheral wall 86 of the housing sleeve 82.

Figure 12:
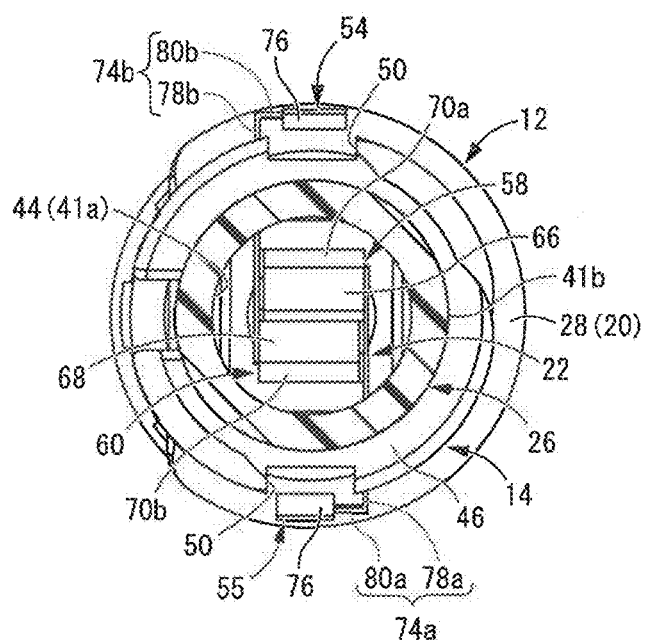
FIG. 12 is a cross sectional view taken along line 12-12 of FIG. 10.

Besides, the axial dimension of the housing sleeve 82 is made smaller than the axial dimension of the straight parts 70a, 70b of the protector main body 52 in a free state of the protector 22. Thus, by the housing sleeve 82 being pulled to the proximal end side, as shown in FIG. 11, the housing sleeve 82 will be stored within the protector main body 52. Also, at this point, the housing sleeve 82 moves with respect to the upper and lower contact parts 66, 68 (the upper and lower plate parts 58, 60) to the proximal end side in the lengthwise direction of the inner needle 18. This will release the contact of the upper and lower contact parts 66, 68 of the protector main body 52 with the peripheral wall 86 of the housing sleeve 82, so that due to the urging force, the upper and lower contact parts 66, 68 of the upper and lower plate parts 58, 60 displace inward in the direction of opposition, namely, in the direction of approaching the inner needle 18. As depicted in FIGS. 11 and 12, the upper and lower contact parts 66, 68 that have displaced inward in the direction of opposition overlap each other when viewed in the axial direction, and are positioned so as to deviate in the axial direction. In the present embodiment, the lower contact part 68 is positioned further on the proximal end side than the upper contact part 66, and their distal end portions overlap each other when viewed in the axial direction. By so doing, the upper and lower contact parts 66, 68 are positioned on the needle axis of the inner needle 18 such that the needle tip 16 of the inner needle 18 is protected by being covered with the upper and lower contact parts 66, 68 of the protector 22.

That is, in the present embodiment, upper and lower contact parts 66, 68 each constitute a protection part for protecting the needle tip 16 of the inner needle 18.

In this way, by the upper and lower contact parts 66, 68 of the upper and lower plate parts 58, 60 displacing inward in the direction of opposition (the direction of approaching the inner needle 18), the upper arm parts 78a, 78b extending outward in the direction of opposition from the distal end portion of the straight parts 70a, 70b while intersecting each other, the forearm parts 80a, 80b extending from the upper arm parts 78a, 78b to the distal end side, and the locking claws 76, 76 will be displaced in the direction of separation from the inner needle 18, namely outward in the direction of opposition. Specifically, the straight parts 70a, 70b displace so as to slope with respect to the axial direction and to narrow inward in the direction of opposition as they go to the distal end side. Meanwhile, the upper arm parts 78a, 78b that are orthogonal to the straight parts 70a, 70b displace so as to slope and extend to the proximal end side as they go outward in the direction of opposition from the distal ends of the straight parts 70a, 70b. Moreover, the forearm parts 80a, 80b and the locking claws 76, 76, which extend from the distal ends of the upper arm parts 78a, 78b while being orthogonal thereto, displace so as to slope with respect to the axial direction and expand outward in the direction of opposition as they go to the distal end side. That is, the outer-needle-hub engaging part 54 and the engaging-part opposing wall 55 displace integrally with the urging parts (the lower plate part 60 and the upper plate part 58), and this will release the lock of the locking claws 76, 76 and the flange part 46, namely the engagement of the outer-needle-hub engaging part 54 and the engaging-part opposing wall 55 of the protector 22 with the outer surface 41b of the outer needle hub 26. By so doing, the inner needle 18 of the inner needle unit 12 is configured to be extracted from the outer needle unit 14.

It is preferable that the distal end portions of the straight parts 70a, 70b that have displaced inward in the direction of opposition are in contact with or slightly remote from the distal end portion of the housing sleeve 82. With this arrangement, the housing sleeve 82 will be stably positioned within the protector main body 52, so as to protect the needle tip 16 of the inner needle 18 with sufficient accuracy.

With the indwelling needle assembly 10 of the present embodiment having the structure described above, when the inner needle 18 is pulled out of the outer needle unit 14, the housing sleeve 82 moves to the proximal end side together with the pulling out of the inner needle 18 to the proximal end side. Consequently, the needle tip 16 will be protected by the protector 22, while the engagement of the outer needle hub 26 with the protector 22 by means of the outer-needle-hub engaging part 54 and the engaging-part opposing wall 55 will be released. That is, the pulling out of the inner needle 18 to the proximal end side, the protection of the needle tip 16 of the inner needle 18 by the protector 22, and the release of engagement of the outer-needle-hub engaging part 54 and the engaging-part opposing wall 55 are configured to be in conjunction with one another. By so doing, other than the time of pulling out the inner needle 18, the outer needle unit 14 and the protector 22 are engaged in a reliable manner, while at the time of pulling out the inner needle 18, the only operation is to pull out the inner needle 18 to the proximal end side and no separate operation is required for protecting the needle tip 16 of the inner needle 18 or for releasing engagement of the outer-needle-hub engaging part 54 and the engaging-part opposing wall 55. Thus, the pulling out of the inner needle 18 can be smoothly performed.

In particular, the upper and lower contact parts 66, 68 extending from the upper plate part 58 and the lower plate part 60 are in contact with the housing sleeve 82, and are not directly in contact with the inner needle 18. Thus, when pulling out the inner needle 18, there is no risk of the inner needle 18 and the upper and lower contact parts 66, 68 rubbing against each other and generating friction, noise or the like, so that it is possible to pull out the inner needle 18 with even better operational feel. That is, when the inner needle 18 is pulled out of the outer needle hub 26, large sliding resistance will not occur, thereby preventing a risk of the outer needle 24 being pulled out together with the inner needle 18.

Also, in the present embodiment, in the initial state, the upper and lower contact parts 66, 68 are in contact with the peripheral wall 86 of the housing sleeve 82, while during pulling out the inner needle 18, the housing sleeve 82 is housed within the protector main body 52 and contact of the upper and lower contact parts 66, 68 with the housing sleeve 82 is released. Accordingly, the upper and lower contact parts 66, 68 as well as the upper and lower plate parts 58, 60 displace inward in the direction of opposition (the direction of approaching the inner needle 18). By so doing, in comparison with the case where the upper and lower contact parts 66, 68 are directly in contact with the inner needle, for example, the amount of displacement of the upper and lower contact parts 66, 68 as well as the upper and lower plate parts 58, 60 can be made larger. Thus, the locking claws 76, 76 (the outer-needle-hub engaging part 54 and the engaging-part opposing wall 55) displace more greatly outward in the direction of opposition (the direction of separation from the inner needle 18). As a result, engagement of the protector 22 with the outer needle unit 14 can be released in a reliable manner.

Next, FIGS. 13 to 16 depict an indwelling needle assembly 96 as a second embodiment of the present invention. In the present embodiment, the shape of the protector and the engagement structure by means of the outer-needle-hub engaging part of the protector with the outer needle hub 26 are different from those in the indwelling needle assembly 10 of the first embodiment. Specifically, a protector 98 serving as a safety mechanism part of the present embodiment includes a protector main body 100 and urging means which is a separate component from the protector main body 100. In the following description, components and parts that are substantially identical with those in the preceding first embodiment will be assigned like symbols in the drawings and not described in any detail.

The protector main body 100 includes an upper mating piece 102 serving as the urging part and a lower mating piece 104 serving as the urging-part opposing wall that are positioned in opposition on the opposite sides in one diametrical direction (the vertical direction in FIG. 14) with the inner needle 18 being interposed therebetween. These upper and lower mating pieces 102, 104 are integrally connected by a proximal end wall 106 at their proximal end portions, whereby the protector main body 100 has a roughly overturned V-shaped or U-shaped cross section overall. The proximal end wall 106 includes a thin-walled portion (hinge part) 107 (see FIG. 17), and with this thin-walled portion (hinge part) 107 of the proximal end wall 106 being as the center, the distal end portions of the upper and lower mating pieces 102, 104 are able to approach and separate with respect to each other. Besides, the proximal end wall 106 includes a passage hole 108 at the center, in which the inner needle 18 is inserted. The inside diameter dimension of the passage hole 108 is made larger than the outside diameter dimension of the inner needle 18, while being made smaller than the outside diameter dimension of the housing sleeve 82 serving as the block part.

The upper mating piece 102 has an approximately rectangular plate shape overall, with its distal end side straightly extending in the axial direction while its proximal end side bending inward in the direction of opposition to the lower mating piece 104. The distal end portion of the upper mating piece 102 is made thicker than the other portion thereof, and this thick portion constitutes an upper contact part 110 which is in contact with the housing sleeve 82. Besides, the upper contact part 110 includes at its axially medial portion a mating concave part 112 that opens onto the lower mating piece 104 side. Specifically, the inner surface of the upper contact part 110 is segmented in the axial direction into the distal end side beyond the mating concave part 112 and the proximal end side beyond the mating concave part 112. The distal end side of the upper contact part 110 beyond the mating concave part 112 constitutes an insertion part 116 that is inserted between the peripheral wall of the proximal end opening part 44 of the outer needle hub 26 and the housing sleeve 82 when the inner needle unit 114 and the outer needle unit 14 are attached. When attached, it is not necessary for the insertion part 116 and the inner surface 41a of the outer needle hub 26 to be in contact with each other, and there may be a clearance therebetween to the extent such that engagement of the outer-needle-hub engaging part 118 with the flange part 46 is not unexpectedly released due to external force or the like.

Moreover, at the distal end portion of the upper mating piece 102, a pair of outer-needle-hub engaging parts 118, 118 are provided so as to extend to the diametrically opposite side across the inner needle 18 and be parallel each other. The outer-needle-hub engaging parts 118, 118 extend roughly in a straight line from the upper contact part 110 of the upper mating piece 102 in the direction parallel to the axis-perpendicular direction (downward in FIG. 16). Also, the outer-needle-hub engaging parts 118, 118 include respective arm parts 120, 120, and the arm parts 120, 120 include respective upper arm parts 122, 122 and forearm parts 124, 124 (see FIG. 17). The forearm parts 124, 124 extend roughly in the axial direction, and the proximal end portions of the forearm parts 124, 124 and the distal end portion of the upper mating piece 102 are connected by the upper arm parts 122, 122 that extend roughly in the axis-perpendicular direction (the vertical direction in FIG. 16). The upper arm parts 122, 122 incline to the proximal end side as they go to the upper mating piece 102 side so as to be wider in the needle axis direction. In addition, at the distal ends of the forearm parts 124, 124, respective locking claws 126, 126 are provided so as to project inward in the radial direction. Therefore, the arm parts 120, 120 and the locking claws 126, 126 constitute the respective outer-needle-hub engaging parts 118, 118. In the present embodiment, in the transverse cross section shown in FIG. 16, the pair of locking claws 126, 126 are arranged so as to be remote from each other on the circumference. Also, with the inner needle unit 114 attached to the outer needle unit 14, the locking claws 126, 126 are arranged on the opposite side to the needle tip inclined surface 16a of the inner needle 18 on the circumference. Specifically, in the present embodiment, the needle tip inclined surface 16a is provided so as to face upward, while the outer-needle-hub engaging parts 118, 118

(the locking claws 126, 126) are provided so as to project downward from the upper mating piece 102.

Meanwhile, the lower mating piece 104 has an approximately rectangular plate shape overall, with its distal end side straightly extending in the axial direction while its proximal end side bending inward in the direction of opposition to the upper mating piece 102. The distal end portion of the lower mating piece 104 bends inward in the direction of opposition to the upper mating piece 102, and the distal end of such bent portion constitutes a lower contact part 128 which is in contact with the housing sleeve 82. Furthermore, the bent portion of the distal end of the lower mating piece 104 branches into two forks. One of the two forks constitutes the above-mentioned lower contact part 128, while the other extends to the distal end side in the needle axis direction and constitutes an inside mating part 130 serving as the engaging-part opposing wall that extends as far as to the inside of the outer needle hub 26 when the inner needle unit 114 and the outer needle unit 14 are attached. In the present embodiment, the inside mating part 130 is formed circumferentially between the pair of locking claws 126, 126. That is, the locking claws 126, 126 (the outer-needle-hub engaging parts 118, 118) and the inside mating part 130 (the engaging-part opposing wall) are provided in opposition to each other at the position deviated in the circumferential direction. Besides, the lower contact part 128 is in opposition to the mating concave part 112 at approximately the same position in the axial direction, and the shape of the lower contact part 128 roughly corresponds to the shape of the mating concave part 112. Specifically, the upper contact part 110 and the lower contact part 128 are in contact with the housing sleeve 82 at the positions roughly deviated from each other in the axial direction.

In preferred practice, the protector main body 100 of such construction can integrally be made of a rigid synthetic resin material. However, the upper mating piece 102, the lower mating piece 104, and the proximal end wall 106 may be formed as separate components from one another and attached later.

The protector main body 100 with the structure described above includes urging means as a separate component at the proximal end side, and in the present embodiment, the urging means is constituted by a plate shape piece 132. The plate shape piece 132 is a plate spring comprising a thin metal plate, and curves in an approximate form of a U-letter overall. The inner surface of one distal end portion on the opening side of the plate shape piece 132 is inserted into a guiding groove 133a provided to the outer surface of the upper mating piece 102 and secured by bonding or the like as needed, and the distal end thereof is embedded and secured to the upper mating piece 102. Meanwhile, the inner surface of the other distal end portion on the opening side of the plate shape piece 132 is inserted into a guiding groove 133b provided to the outer surface of the lower mating piece 104 and secured by bonding or the like as needed, and the distal end thereof is embedded and secured to the lower mating piece 104. Besides, the medial portion of the plate shape piece 132 is arranged so as to cover the proximal end wall 106 from the proximal end side with a prescribed separation distance therebetween. Moreover, the plate shape piece 132 includes a passage hole 134 at the center portion, in which the inner needle 18 is inserted.

The housing sleeve 82 serving as the block part is provided to the inserted portion of the inner needle 18 into the protector 98. In the present embodiment, the axial dimension from the distal end surface of the proximal end wall 106 to the proximal end surface of the upper contact part 110 is made larger than the axial dimension of the housing sleeve 82.

The inner needle unit 114 of the present embodiment is constituted by the inner needle 18 being retained by the inner needle hub 20 while the protector 98 and the housing sleeve 82 being externally mounted about the inner needle 18. By the inner needle 18 of the inner needle unit 114 being inserted into the outer needle unit 14, the indwelling needle assembly 96 of the present embodiment is provided. Specifically, with the indwelling needle assembly 96, in the initial state shown in FIGS. 13 to 16, the proximal end side of the inner needle 18 is inserted into the passage hole 108 of the proximal end wall 106 and the passage hole 134 of the plate shape piece 132 of the protector main body 100. In addition, the protector 98 is positioned within the housing space 38 of the housing tube part 34 in roughly its entirety, while the distal end portion of the protector 98, namely, the insertion part 116 which is the distal end portion of the upper mating piece 102 and the inside mating part 130 which is the distal end portion of the lower mating piece 104, is inserted into the inside of the proximal end opening part 44 of the outer needle hub 26. When attached, the it is not necessary for the inside mating part (the engaging-part opposing wall) 130 and the inner surface 41a of the outer needle hub 26 to be in contact with each other, and there may be a clearance therebetween to the extent such that engagement of the outer-needle-hub engaging parts 118, 118 with the flange part 46 is not unexpectedly released.

Figure 18:
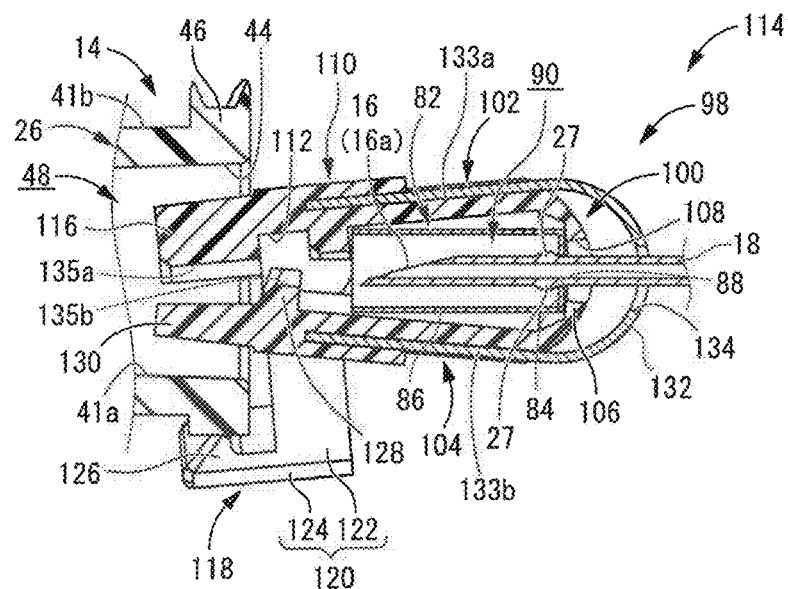
FIG. 18 is an enlarged vertical cross sectional view of a principal part of the indwelling needle assembly shown in FIG. 17.

The peripheral wall 86 of the housing sleeve 82 is retained between opposed faces of the upper and lower contact parts 110, 128 by being clasped from both sides. When the both end portions of the plate shape piece 132 are in a free state of not clasping the housing sleeve 82 as shown in FIG. 18 described later, they are closer to each other than they are in the state shown in FIG. 15. That is, by the housing sleeve 82 is being clasped between the upper and lower contact parts 110, 128, the upper and lower contact parts 110, 128 are pushed to expand outward in the direction of opposition. In other words, in the initial state as shown in FIG. 13 to 16, based on elastic recovery force of the plate shape piece 132, urging force is acted from both sides of the housing sleeve 82 such that the upper and lower contact parts 110, 128 are urged inward in the direction of opposition (in the direction of approaching the inner needle 18). Therefore, displacement of the upper and lower mating pieces 102, 104 inward in the direction of opposition is limited by being in contact with the housing sleeve 82. Besides, the housing sleeve 82 is positioned with respect to the protector 98 in the axial direction due to the urging force.

Figure 16:
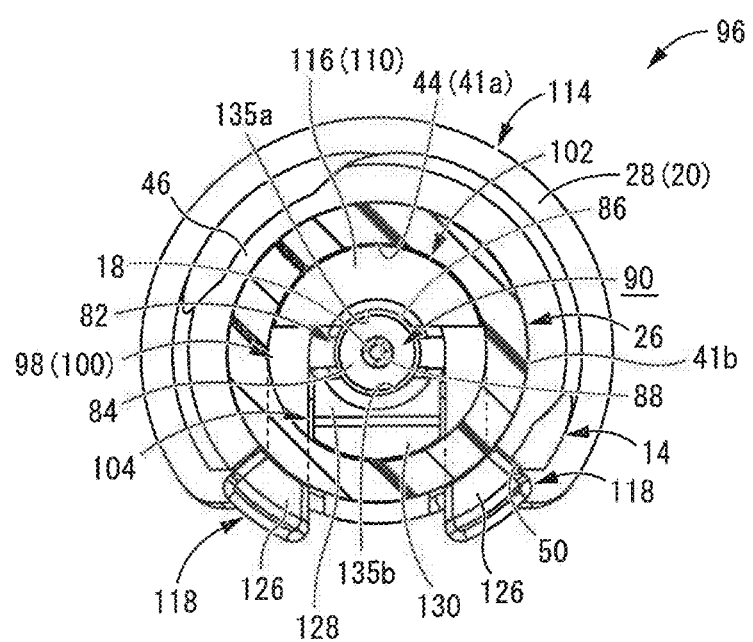
FIG. 16 is an enlarged transverse cross sectional view of a cross section taken along line 16-16 of FIG. 13.

The upper and lower contact parts 110, 128 includes, on the respective opposed faces, positioning concave parts 135a, 135b that curve in a shape corresponding to the peripheral wall 86 of the housing sleeve 82 at the center portion in the width direction (the lateral direction in FIG. 16). Accordingly, the peripheral wall 86 of the housing sleeve 82 is clasped and retained between the positioning concave parts 135a, 135b provided to the respective opposed faces of the upper and lower contact parts 110, 128. By so doing, the housing sleeve 82 can be clasped not only in the direction of opposition of the contact parts 110, 128 but also in the circumferential direction.

Moreover, in the state where the inner needle unit 114 and the outer needle unit 14 are attached, on the outer circumferential surface of the flange part 46 provided to the proximal end opening part 44 which is on the outer surface 41b of the outer needle hub 26, the engaging groove 50 provided with a prescribed circumferential dimension (see FIG. 16) and the locking claws 126, 126 are aligned in the circumferential direction, and the locking claws 126, 126 are engaged with the end face of the distal end side of the flange part 46 via the engaging groove 50. With this arrangement, the peripheral wall of the proximal end opening part 44 is clasped and retained between the inside mating part 130 (the engaging-part opposing wall) and the pair of locking claws 126, 126 (the outer-needle-hub engaging parts 118, 118) with a clearance as needed. By the inside mating part 130 being in contact with the inner surface 41a of the outer needle hub 26, displacement of the outer-needle-hub engaging parts 118, 118 from the outer needle hub 26 (the flange part 46) is limited.

Figure 17:
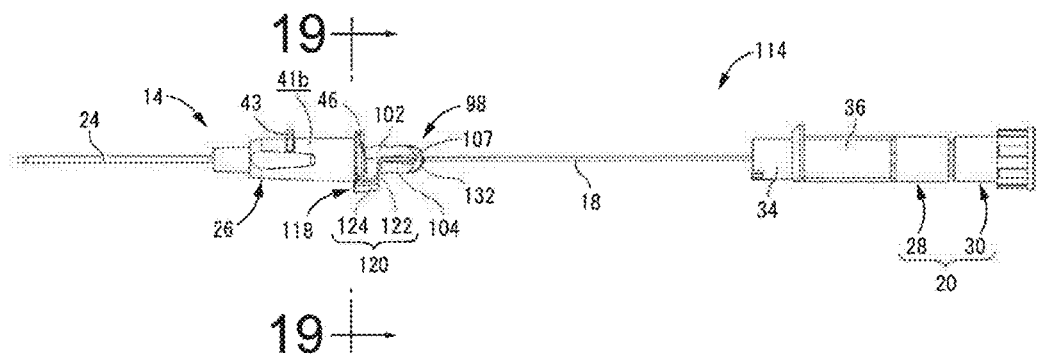
FIG. 17 is a front view suitable for explaining the state where, with the indwelling needle assembly shown in FIG. 13, an inner needle is pulled out of an outer needle hub and engagement by an outer-needle-hub engaging part is released.
Figure 19:
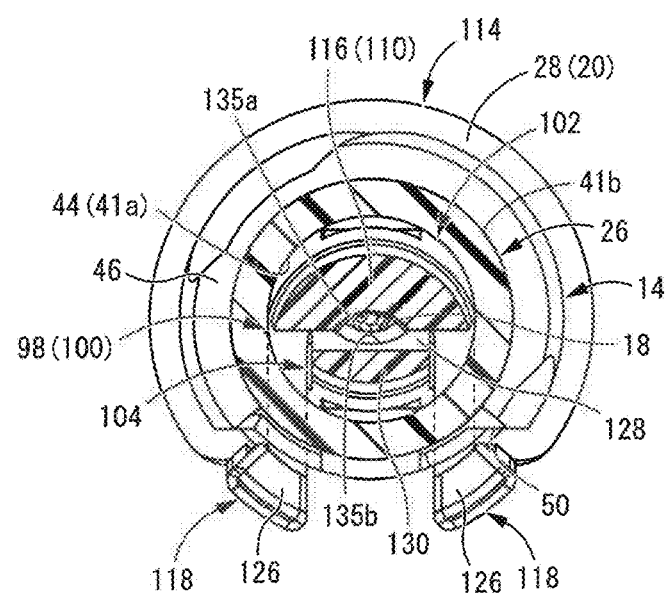
FIG. 19 is an enlarged transverse cross sectional view of a cross section taken along line 19-19 of FIG. 17.

Operation of the indwelling needle assembly 96 of the present embodiment constructed in the above manner in use will be described hereinbelow while indicating in FIGS. 17 to 19.

First, with the outer needle 24 kept inserted in the blood vessel of the patient, the inner needle 18 is pulled out of the outer needle 24 to the proximal end side. By so doing, the large-diameter parts 27, 27 of the inner needle 18 and the bottom wall 84 of the housing sleeve 82 are engaged, and the distal end side from the large-diameter parts 27, 27 of the inner needle 18 is covered by the housing sleeve 82. Then, by the inner needle 18 being pulled out further to the proximal end side, with the inner needle 18 and the housing sleeve 82 kept engaged, the housing sleeve 82 will be pulled together with the inner needle 18 to the proximal end side. In the present embodiment, the axial dimension from the distal end surface of the proximal end wall 106 to the proximal end surface of the upper contact part 110 is made larger than the axial dimension of the housing sleeve 82. Accordingly, by the housing sleeve 82 being pulled to the proximal end side, the proximal end surface of the housing sleeve 82 comes into contact with the distal end surface of the proximal end wall 106, so that the housing sleeve 82 is housed within the protector 98.

As a result, contact of the housing sleeve 82 with the upper and lower contact parts 110, 128 is released, and the upper and lower contact parts 110, 128 each displace inward in the direction of opposition (the direction of approaching the inner needle 18) due to the urging force by the plate shape piece 132. Consequently, as shown in FIGS. 18 and 19, the lower contact part 128 is inserted into the mating concave part 112, and the upper and lower contact parts 110, 128 will cover and protect the needle tip 16 of the inner needle 18 in the axial direction. That is, in the present embodiment, the upper and lower contact parts 110, 128 constitute a protection part that protects the needle tip 16 of the inner needle 18. After displacement of the upper and lower contact parts 110, 128 inward in the direction of opposition, it is preferable that the outer circumferential surface of the housing sleeve 82 and the inner surfaces of the upper and lower mating pieces 102, 104 be in contact or spaced away from each other with a slight distance. By so doing, the housing sleeve 82 will be stably retained within the protector 98. Also, the needle tip 16 of the inner needle 18 need not be protected entirely by the upper and lower contact parts 110, 128 when viewed in the axial direction, but may be partially protected as shown in FIG. 19. In this way, by at least a portion of the needle tip 16 being covered when viewed in the axial direction, it is possible to prevent protrusion and inadvertent pricking of the inner needle 18 after use.

Additionally, by the lower mating piece 104 displacing inward in the direction of opposition to the upper mating piece 102, the peripheral wall of the proximal end opening part 44 of the outer needle hub 26 is released from the clasp by the inside mating part 130 and the locking claws 126, 126 of the outer-needle-hub engaging parts 118, 118, whereby the engagement of the protector 98 with the outer needle hub 26 is released. Moreover, by the upper mating piece 102 displacing in the direction of approaching the inner needle 18, the outer-needle-hub engaging parts 118, 118 extending from the distal end portion of the upper mating piece 102 to the diametrically opposite side displaces in the direction of separation from the inner needle 18, namely the direction of separation from the outer peripheral surface of the flange part 46 of the outer needle hub 26. Furthermore, by the upper mating piece 102 displacing in the direction of approaching the inner needle 18, the gap between the insertion part 116 and the inner surface 41a of the outer needle hub 26 increases as well. For these reasons, the engagement of the outer needle hub 26 with the protector 98 by means of the outer-needle-hub engaging parts 118, 118 can be easily released.

The indwelling needle assembly 96 of the present embodiment is also able to exhibit the same effect as the indwelling needle assembly 10 described in the first embodiment.

In this embodiment in particular, the urging means that exerts urging force on the upper and lower contact parts 110, 128 is provided by the plate shape piece 132 which is a separate component from the protector main body 100. Thus, in comparison with the case where the protector main body 52 itself has the urging force as described in the first embodiment, it is also possible to exert stronger urging force, for example. With this arrangement, the needle tip 16 of the inner needle 18 can be more stably covered by the upper and lower contact parts 110, 128 which constitute the protection part. In addition, since the inside mating part 130 displaces more reliably in the direction of approaching the inner needle 18, the engagement of the protector 98 with the outer needle hub 26 by means of the outer-needle-hub engaging parts 118, 118 can be release with more sufficient accuracy.

Besides, normally, the needle tip inclined surface 16a of the inner needle 18 is inserted so as to be positioned on the circumferentially opposite side to the body surface of the patient. Thus, according to the present embodiment, the locking claws 126 that connect the protector 98 and the outer needle hub 26 are arranged on the body surface side of the patient during insertion. Therefore, the treating person who operates the indwelling needle assembly 96 is less likely to touch the connected portion of the protector 98 and the outer needle hub 26, thereby preventing unintended release of connection between the protector 98 and the outer needle hub 26.

Figure 20:
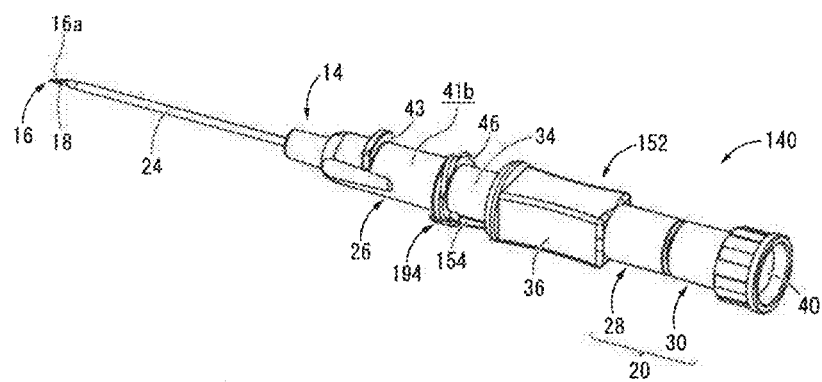
FIG. 20 is a perspective view of an indwelling needle assembly as a third embodiment of the present invention.
Figure 21:
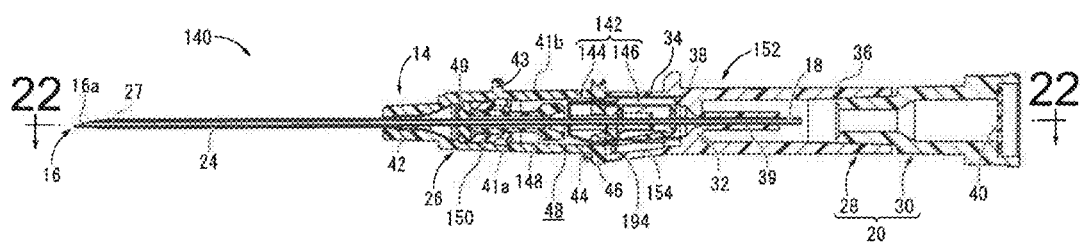
FIG. 21 is a vertical cross sectional view of the indwelling needle assembly shown in FIG. 20, taken along line 21-21 of FIG. 22.
Figure 22:
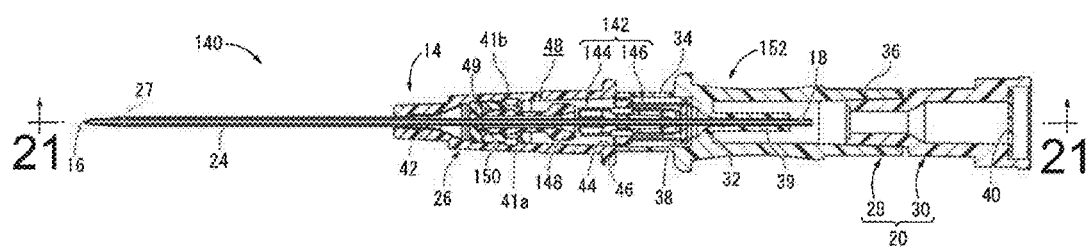
FIG. 22 is a cross sectional view taken along line 22-22 of FIG. 21.

Next, FIGS. 20 to 22 depict an indwelling needle assembly 140 as a third embodiment of the present invention. A protector 142 serving as the safety mechanism part of the in the present embodiment includes a metal member 144 and a resin member 146 attached to the metal member 144. In the present embodiment, the large-diameter part 27 whose diametrical direction is made large is integrally formed with the distal end portion of the inner needle 18 about the entire circumference in the circumferential direction. While no particular limitation is imposed in any way as to the manufacturing method of the inner needle 18 having such large-diameter part 27, the inner needle 18 can be preferably formed by centerless process or the like, for example.

In addition, a pusher 148 and a pusher guide 150 together with the hemostasis valve 49 are housed within the inside area 48 of the outer needle hub 26 of the present embodiment. The pusher 148 has a roughly tubular shape overall and its inside diameter dimension is made larger than the outside diameter dimension of the inner needle 18. Besides, the pusher guide 150 has a roughly tubular shape overall, and the pusher guide 150 is arranged radially between the pusher 148 and the outer needle hub 26. The hemostasis valve 49 is mounted inside the outer needle hub 26, while the pusher 148 and the pusher guide 150 are positioned at the proximal end side of the hemostasis valve 49. The pusher 148 slides with respect to the pusher guide 150 and is movable in the axial direction.

With such hemostasis valve mechanism, after the outer needle unit 14 is indwelled in the skin of the patient, by a syringe or the like being inserted from the proximal end opening part 44 of the outer needle hub 26, the distal end of the syringe pushes the pusher 148 toward the distal end so as to open the hemostasis valve 49. Meanwhile, by extracting the syringe or the like from the outer needle unit 14, the hemostasis valve 49 will rapidly close due to elastic recovery action.

Figure 23:
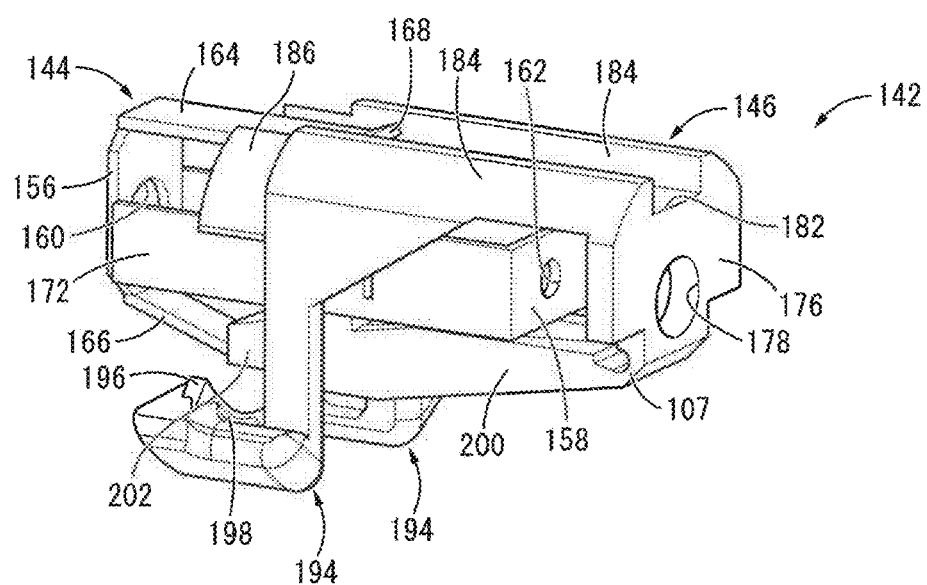
FIG. 23 is a perspective view of a safety mechanism part constituting the indwelling needle assembly shown in FIG. 20.
Figure 24:
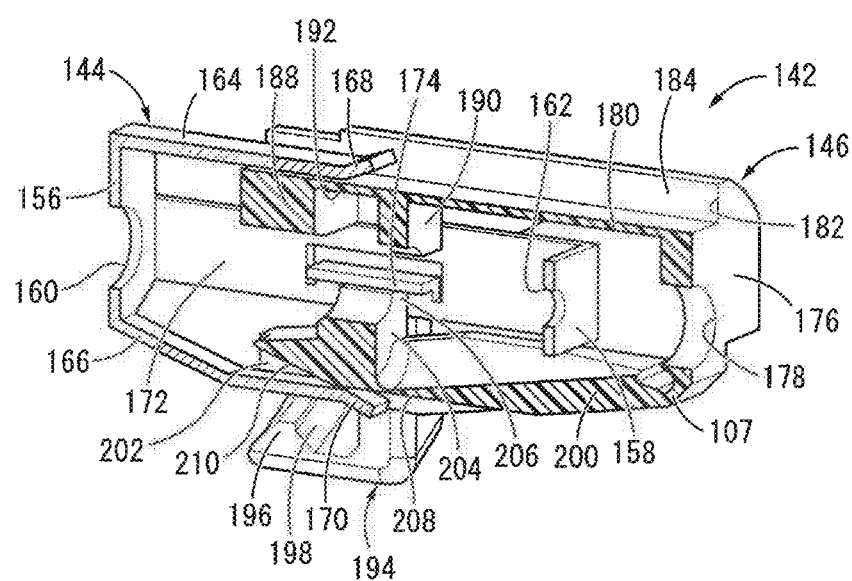
FIG. 24 is a perspective cross sectional view of the safety mechanism part shown in FIG. 23.
Figure 25:
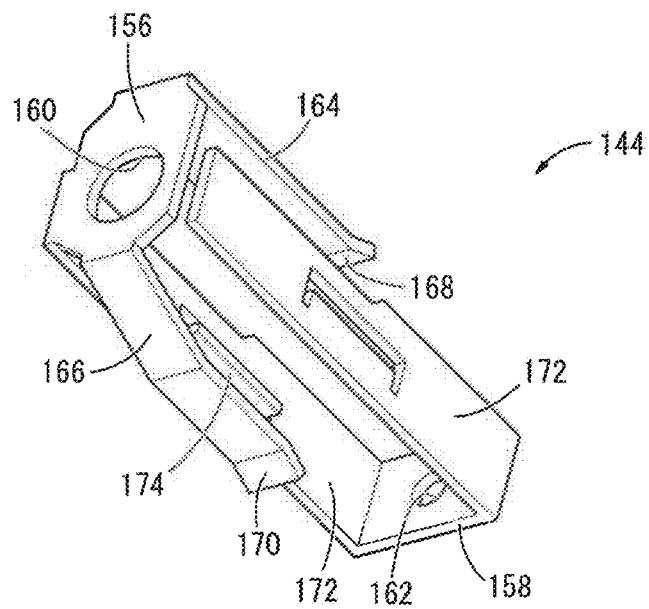
FIG. 25 is a perspective view of a metal member constituting the safety mechanism part shown in FIG. 23.

Here, the protector 142 is mounted to an inner needle unit 152, which is attached to the outer needle unit 14, of the present embodiment. With the housing tube part 34 of the present embodiment, the lower peripheral wall comprises a slope wall 154 that slopes radially outward toward the distal end side. Accordingly, the housing space 38 is largely obtained, so that when the protector 142 is mounted within the housing space 38, the peripheral wall of the housing tube part 34 is configured not to touch the protector 142. As depicted in FIGS. 23 and 24, the protector 142 includes the metal member 144 in which the inner needle 18 is inserted, and the resin member 146 attached to the metal member 144.

The metal member 144 is a component made of NiTi alloy, stainless steel or the like, and as shown in FIGS. 25 to 28, includes a front wall 156 and a rear wall 158 serving as the inner-needle engaging part that are opposed in front and rear. The front wall 156 has a roughly octagonal plate shape that extends in the direction orthogonal to the needle axis, and includes an inner-needle through hole 160 at the center portion in which the inner needle 18 is inserted. Meanwhile, the rear wall 158 has a roughly rectangular plate shape that extends in the direction orthogonal to the needle axis, and includes an inner-needle insertion hole 162 at the center portion in which the inner needle 18 is inserted. These inner-needle through hole 160 and the inner-needle insertion hole 162 are provided so as to be aligned on the needle axis of the inner needle 18. The inner-needle through hole 160 has a larger diameter than the maximum outside diameter of the inner needle 18 at the portion where the large-diameter part 27 is formed, while the inner-needle insertion hole 162 has a smaller diameter than the maximum outside diameter of the inner needle 18 at the portion where the large-diameter part 27 is formed.

Moreover, with the front wall 156, an upper elastic wall 164 and a lower elastic wall 166 are integrally formed. These elastic walls 164, 166 in pairs both have a plate shape and extend rearward from the upper and lower ends of the front wall 156 in a cantilever manner so as to be vertically opposed to each other with a prescribed distance in between. Also, each of the elastic walls 164, 166 is a plate spring which is permitted to undergo elastic bending deformation in the thickness direction. With this arrangement, in the front of the metal member 144, there is formed a plate spring which has a roughly U-letter shaped cross section overall including the front wall 156 and the upper and lower elastic walls 164, 166. The distal end portions thereof, which are on the opening side of the U-letter shaped plate spring, extend toward the proximal end side in the needle axis direction.

Figure 27:
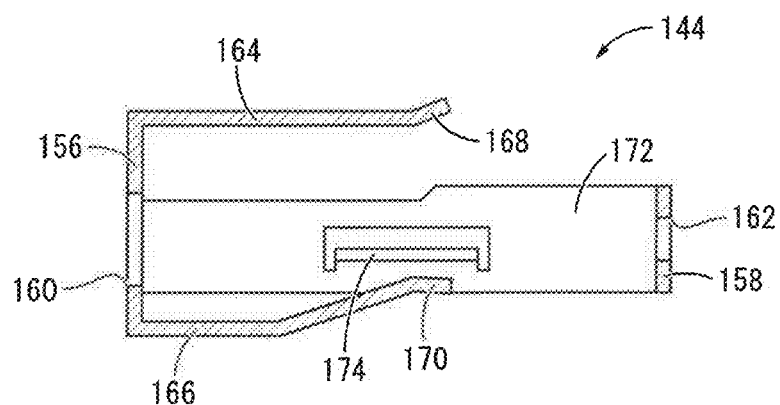
FIG. 27 is a cross sectional view taken along line 27-27 of FIG. 26.
Figure 28:
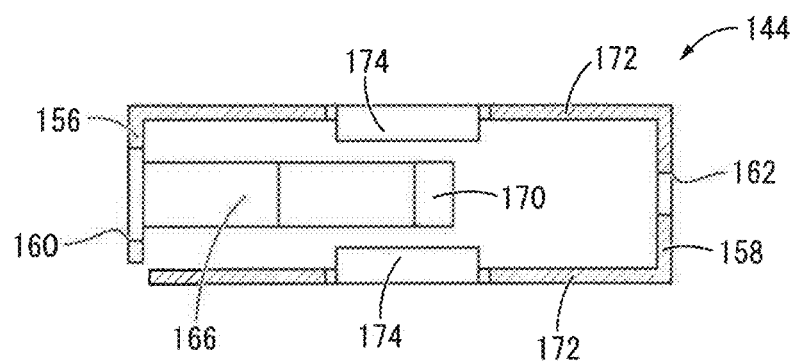
FIG. 28 is a cross sectional view taken along line 28-28 of FIG. 26.

More specifically, the upper elastic wall 164 extends rearward so as to be roughly orthogonal to the front wall 156, and the projecting distal end portion thereof projecting from the front wall 156 constitutes an upper guide part 168 serving as a guiding part that slopes upward as it goes rearward. Meanwhile, with respect to the lower elastic wall 166, as shown in FIGS. 27 and 28, the front-rear intermediate portion slopes relative to the front-rear end portions, and the front-rear intermediate portion slopes with respect to the needle axis direction so as to slope upward as it goes rearward. Moreover, the rear end part of the lower elastic wall 166 (the projecting distal end portion) constitutes a lower guide part 170 serving as a guiding part. As shown in FIG. 24, when the lower elastic wall 166 is elastically deformed until its intermediate portion becomes parallel to the needle axis direction, the lower guide part 170 is configured to be a slope shape that slopes downward as it goes rearward.

Furthermore, with the rear wall 158, a left/right pair of locking walls 172, 172 are integrally formed. The locking walls 172, 172 have a roughly flat plate shape and extend forward from the left and right ends of the rear wall 158, respectively, so as to be opposed to each other in the left-right direction with a prescribed distance in between.

Figure 26:
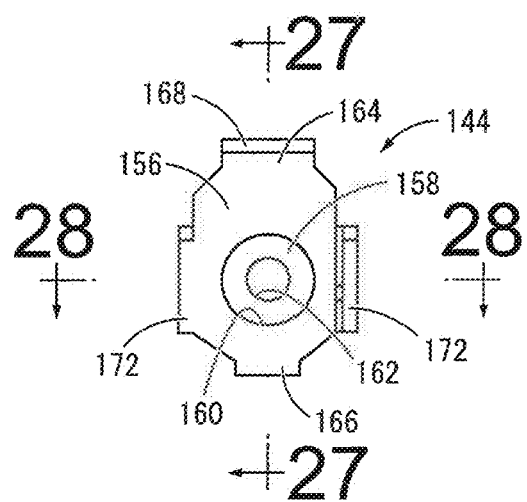
FIG. 26 is a left side view of the metal member shown in FIG. 25.

The locking walls 172, 172 include at their center portions respective locking pieces 174 serving as the block part that extend inward in the direction of opposition. The locking piece 174 is formed by the center portion of the locking wall 172 being bent inward direction of opposition through punch press working, and extends in the front-back direction with a prescribed length. Moreover, in the present embodiment, with respect to the pair of locking walls 172, 172, the respective locking pieces 174, 174 having a mutually symmetrical shape in the left-right direction in FIG. 26 are formed. The locking pieces 174, 174 are formed in the same positions as each other in the vertical direction as well as in the front-back direction, and are arranged in opposition in the left-right direction in FIG. 26. In the present embodiment, as will be described later, the metal member 144 is formed through press working of a plate material (a plate), and the locking pieces 174, 174 have a roughly plate shape.

Since the front end of one locking wall 172 is integrally continuous with the front wall 156, the entire metal member 144 is integrally formed. The metal member 144 of the present embodiment is formed by, for example, a metal plate material being subjected to press working, punched into a prescribed shape, and bent. Specifically, in the present embodiment, the metal member 144 including the locking pieces (the block part) 174, 174 is constituted by a process-formed product of a metal plate material (a plate).

Meanwhile, the resin member 146 is a rigid member made of synthetic resin material such as polypropylene, and includes a vertical wall 176 as shown in FIG. 24. The vertical wall 176 has a plate shape that extends in the direction orthogonal to the needle axis, and includes an inner-needle passage hole 178 at the center portion, in which the inner needle 18 is inserted. The inner-needle passage hole 178 is a circular hole that perforates the vertical wall 176 in the axial direction, and has a diameter that is sufficiently larger than the maximum outside diameter dimension of the inner needle 18. Thus, the inner needle 18 is inserted with a gap into the inner-needle passage hole 178 even with the relatively large dimension tolerance of the vertical wall 176 made of synthetic resin. In this way, by making the diameter of the inner-needle passage hole 178 larger than the outside diameter of the inner needle 18 so as to provide a clearance, it is possible to more effectively prevent the outer needle 24 from being subjected to force in the direction of dislodgment from the skin when the inner needle 18 is pulled out.

Besides, a sliding contact wall 180 serving as an urging-part opposing wall is integrally formed with the upper end portion of the vertical wall 176. The sliding contact wall 180 extends forward so as to be roughly orthogonal to the vertical wall 176, and includes on its upper surface an upper concave groove 182 serving as a guiding groove and extending in the front-back direction. Specifically, a pair of upper side walls 184, 184 project upward from both ends in the width direction (the vertical direction in FIG. 22) of the sliding contact wall 180, and the outer peripheral surfaces of the upper side walls 184, 184 each have a curving surface that curves gradually inward in the direction of opposition as it goes upward. Moreover, the outer peripheral surfaces at the distal end portions of the upper side walls 184, 184 are positioned radially inside (lower side) in comparison with other portions of the upper side walls 184, 184, and constitute respective insertion parts 186, 186. The curvature radius of the outer peripheral surfaces of the insertion parts 186, 186 is made roughly equal to the inner diameter radius of the proximal end opening part 44 of the outer needle hub 26.

Furthermore, at the front end of the sliding contact wall 180, a guide projection 188 and a positioning projection 190 are formed so as to project downward. The guide projection 188 and the positioning projection 190 are arranged in front and rear with a prescribed distance therebetween, so as to provide a recess 192 opening downward between the guide projection 188 and the positioning projection 190 in the front-back direction.

Moreover, at the front end of the sliding contact wall 180, integrally formed are a left/right pair of connecting parts 194, 194 that have the same structure as the outer-needle-hub engaging parts 118, 118 of the second embodiment. Specifically, the respective connecting parts 194, 194 are provided on the left and right ends of the sliding contact wall 180 in a roughly left-right symmetrical shape and extend downward so as to be roughly orthogonal to the sliding contact wall 180. The lower end portions of the connecting parts 194, 194 project forward, whose the front ends include respective locking claws 196, 196 that are integrally formed therewith and project upward. By the locking claws 196, 196 being engaged with the flange part 46 formed to the proximal end of the outer needle hub 26, the resin member 146 is connected to the outer surface 41b of the outer needle hub 26 in a detachable manner. In this way, by the locking claws 196, 196 of the connecting parts 194, 194 being engaged with the flange part 46, when the inner needle 18 is pulled out, to be described later, the resin member 146 is prevented from moving to the proximal end side together with movement of the metal member 144 to the proximal end side. Thus, the locking claws 196, 196 are able to assist movement of the metal member 144 relative to the resin member 146. In addition, on the proximal end side of the locking claws 196, 196 in the needle axis direction, there are formed respective sloping parts 198, 198 that gradually slope upward (namely, to the projecting distal end side of the locking claws 196, 196 and in the direction of approaching the inner needle 18) toward the distal end side in the needle axis direction. Accordingly, when the inner needle 18 is pulled out, the locking claws 196, 196 are configured to move while sliding or rotating in the diagonal direction with respect to the flange part 46. Owing to such sloping parts 198, 198, when the inner needle 18 is pulled out, the locking claws 196, 196 are less likely to be caught by the flange part 46, thereby even more effectively preventing the outer needle 24 from being subjected to force in the direction of dislodgment from the skin.

Additionally, to the lower end portion of the vertical wall 176, a retaining wall 200 is integrally and continuously provided. The retaining wall 200 is roughly orthogonal to the vertical wall 176 and extends forward, and includes a hinge part 107 at its rear end, which is the connected end with the vertical wall 176, so that the angle with respect to the vertical wall 176 is variable. The hinge part 107 of the present embodiment is formed by the inside of the connected section of the retaining wall 200 and the vertical wall 176 being gouged to be partially thin-walled. Moreover, the retaining wall 200 is situated in opposition to the sliding contact wall 180 so as to be remote downwardly therefrom, and the sliding contact wall 180 and the retaining wall 200 are able to approach each other due to deformation of the hinge part 107. Besides, the retaining wall 200 is made narrower than the sliding contact wall 180 so that a distal end portion 202 of the retaining wall 200 is inserted between the left/right pair of the connecting parts 194, 194.

Furthermore, a needle-tip protection part 204 is integrally formed with the retaining wall 200 of the resin member 146. The needle-tip protection part 204 has a block shape or thick-walled plate shape, and projects upward, namely in the direction of opposition to the sliding contact wall 180. Also, on the both left and right sides of the needle-tip protection part 204, respective contact retaining parts 206, 206 are integrally formed so as to project further upward than the needle-tip protection part 204 does, and a concave groove is formed between the contact retaining parts 206, 206 so as to open upward with a roughly semicircular cross section and extend in the front-back direction.

Moreover, on the lower surface of the retaining wall 200, a lower concave groove 208 serving as the guiding groove is formed so as to extend in the front-back direction. With the lower concave groove 208, the bottom surface on the distal end side beyond the needle-tip protection part 204 constitutes a sloping guide surface 210 sloping upwardly toward the distal end.

The metal member 144 and the resin member 146 of the above construction are assembled each other and constitute the protector 142.

Specifically, the sliding contact wall 180 and the retaining wall 200 are attached by being inserted between opposed faces of the upper/lower pair of elastic walls 164, 166 of the metal member 144 from the distal end side in the axial direction. By so doing, the upper elastic wall 164 is inserted into the upper concave groove 182 so as to be overlapped with the sliding contact wall 180 from above, while the lower elastic wall 166 is inserted into the lower concave groove 208 so as to be overlapped with the retaining wall 200 from below. Also, the rear end parts of the upper and lower elastic walls 164, 166 constitute the upper and lower guide parts 168, 170 that expand vertically outward. Due to contact of the resin member 146 with the upper and lower guide parts 168, 170 in the axial direction, the opposed elastic walls 164, 166 are vertically pushed open, and the resin member 146 is guided between the upper and lower elastic walls 164, 166. This makes it easy to attach the metal member 144 and the resin member 146 in the axial direction.

In addition, with the mutually attached metal member 144 and resin member 146, relative movement in the axial direction is permitted, while the amount of relative displacement is limited on the axially both sides so as to prevent separation. Specifically, when the metal member 144 moves to be distant from the resin member 146, the rear wall 158 of the metal member 144 and the positioning projection 190 of the resin member 146 come into contact, so as to limit the amount of movement and prevent separation. On the other hand, when the metal member 144 moves to be near to the resin member 146, the front wall 156 and the rear wall 158 come into contact with the resin member 146, so as to limit the amount of movement.

Besides, the guide projection 188 provided to the distal end part of the sliding contact wall 180 is inserted vertically between the upper elastic wall 164 and the left and right locking walls 172, 172, so that relative up-down tilting motion (prizing displacement in the vertical direction) of the metal member 144 and the resin member 146 is limited. Furthermore, the positioning projection 190 is inserted to the upper part between the opposed left and right locking walls 172, 172, the contact retaining parts 206, 206 are inserted to the lower part between the opposed left and right locking walls 172, 172, and the upper elastic wall 164 and the lower elastic wall 166 are respectively inserted into the upper concave groove 182 and the lower concave groove 208. With these arrangements, relative rotation (torsional displacement) and left-right tilting motion (prizing displacement in the lateral direction) of the metal member 144 and the resin member 146 are limited. Additionally, the left and right locking walls 172, 172 of the metal member 144 are inserted between the left and right connecting parts 194, 194 of the resin member 146, so as to limit relative movement of the metal member 144 and the resin member 146 in the direction other than the axial direction.

In this way, relative movement of the metal member 144 and the resin member 146 is limited in the direction other than the axial direction, and in particular, by providing tilting motion prevention mechanism for limiting tilting motion with respect to the needle axis, the metal member 144 is retained in the prescribed position with respect to the resin member 146. Therefore, when the inner needle 18 is pulled out, the needle-tip protection part 204 is moved reliably to the prescribed position, and the needle axis of the inner needle 18 inserted in the metal member 144 is prevented from tilting.

Also, the contact retaining parts 206, 206 provided to the retaining wall 200 are overlapped and in contact with the locking pieces 174, 174 provided to the locking walls 172, 172 of the metal member 144 from below. Since the contact retaining parts 206, 206 of the resin member 146 are interposed vertically between the lower elastic wall 166 and the left and right locking walls 172, 172 of the metal member 144, the lower elastic wall 166 is deformed downwardly in an elastic manner. By so doing, on the retaining wall 200 equipped with the needle-tip protection part 204 and the contact retaining parts 206, 206, urging force based on elasticity of the lower elastic wall 166 is exerted upward, namely in the direction of approaching the inner needle 18. Therefore, in the present embodiment, the retaining wall 200 constitutes the urging part that is urged in the direction of approaching the inner needle 18. In other words, the sliding contact wall 180 and the retaining wall 200 of the resin member 146 are elastically urged in the direction of approaching each other by the upper and lower elastic walls 164, 166 of the metal member 144.

Furthermore, by the contact retaining parts 206, 206 being in contact with the locking pieces 174, 174 of the metal member 144, approaching displacement of the retaining wall 200 to the sliding contact wall 180 or the inner needle 18 is prevented. Accordingly, the needle-tip protection part 204 provided to the retaining wall 200 is positioned below the needle axis of the inner needle 18, and retained at the standby position away from the needle axis of the inner needle 18. Therefore, in the present embodiment, the locking pieces 174, 174 constitute the block part that is in contact with the contact retaining parts 206, 206 provided to the retaining wall 200 and retains the needle-tip protection part 204 provided to the retaining wall 200 at the position remote from the inner needle 18. With this arrangement, the inner needle 18 is able to penetrate the protector 142 in the axial direction through the inner-needle through hole 160 and the inner-needle insertion hole 162 of the metal member 144 as well as the inner-needle passage hole 178 of the resin member 146.

With the protector 142 of the present embodiment, the mechanism for retaining the needle-tip protection part 204 at the position away from the needle axis of the inner needle 18 is provided between the metal member 144 and the resin member 146. Thus, by the needle-tip protection part 204 being retained at the position away from the needle axis of the inner needle 18 in advance before insertion of the inner needle 18 into the protector 142, the inner needle 18 is readily inserted into the protector 142. Moreover, the locking pieces 174, 174 are provided on the left and right sides of the metal member 144, respectively, and the locking pieces 174, 174 are in contact with the contact retaining parts 206, 206 respectively provided to the left and right ends of the needle-tip protection part 204. Thus, contact reaction force will act on the needle-tip protection part 204 in a balanced manner, thereby preventing unnecessary torsion of the resin member 146 with respect to the metal member 144.

Besides, the contact retaining parts 206, 206 of the resin member 146 are movable in the front-back direction while being in contact with the lower surfaces of the locking pieces 174, 174 of the metal member 144, so that the metal member 144 and the resin member 146 are relatively slidable in front and rear in the axial direction. By adopting synthetic resin or the like having self-lubricating ability as the forming material of the resin member 146 so as to make its friction coefficient small, frictional resistance will be minimized during sliding contact with the metal member 144, thereby realizing smoother operation.

Then, such protector 142 is attached to the proximal end part of the outer needle hub 26. Specifically, with the protector 142 externally placed about the inner needle 18, the insertion parts 186, 186 provided to the distal end portion and the distal end portion 202 of the retaining wall 200 are inserted from the proximal end opening part 44 of the outer needle hub 26 to the inside, while the locking claws 196, 196 provided to the connecting parts (the outer-needle-hub engaging parts) 194, 194 of the resin member 146 are engaged with the flange part 46 provided on the outer surface 41b of the outer needle hub 26. That is, the peripheral wall of the outer needle hub 26 are clasped by the locking claws 196, 196 and the distal end portion 202 of the retaining wall 200 from outside and inside. Accordingly, in the present embodiment, the distal end portion 202 of the retaining wall 200 constitutes the engaging-part opposing wall that is positioned in opposition to the connecting parts (the outer-needle-hub engaging parts) 194, 194 with the outer needle hub 26 interposed therebetween.

With the protector 142 attached to the outer needle hub 26 in this way, the front half of the protector 142 is inserted in the outer needle hub 26, while the rear half thereof is exposed. In the present embodiment, similar to the first embodiment described previously, there are provided a pair of engaging grooves (50, 50) to the flange part 46, and the left and right connecting parts 194, 194 are inserted in the respective engaging grooves (50, 50). That is, a portion of the flange part 46 of the outer needle hub 26 is inserted between the left and right connecting parts 194, 194 and engaged in the circumferential direction, so as to prevent relative rotation (torsional displacement) of the resin member 146 and the outer needle hub 26.

Moreover, the rear half of the protector 142 projecting from the outer needle hub 26 is housed in the housing space 38 of the inner needle hub 20. The housing tube part 34, which is the peripheral wall of the housing space 38, is provided with the slope wall 154 at its lower side. The slope wall 154 is overlapped with the connecting parts 194, 194 of the resin member 146 from the proximal side, thereby preventing release of engagement of the resin member 146 with the outer needle hub 26 due to deformation of the connecting parts 194, 194. With the slope wall 154 of the present embodiment, the projecting dimension from the outer circumferential surface of the housing tube part 34 becomes greater toward the side where the slope wall 154 is overlapped with the connecting parts 194, 194, and since the lower surface comprises a sloping surface, catching or the like is avoided.

The inner needle 18 is inserted into the protector 142, and the inner needle 18 passes through between the opposed faces of the upper and lower elastic walls 164, 166, and between the opposed faces of the left and right locking walls 172, 172 of the metal member 144. In addition, the inner needle 18 passes through between the opposed faces of the sliding contact wall 180 and the retaining wall 200 of the resin member 146.

Operation of the indwelling needle assembly 140 constructed in the above manner in use will be described hereinbelow while referring to the drawings.

Specifically, with the indwelling needle assembly 140 of the present embodiment as well, in the initial state before the use, as shown in FIGS. 20 to 22, the protector 142 is mounted externally about the inner needle 18 of the inner needle unit 152. Besides, the inner needle 18 that passes through the protector 142 is inserted into the outer needle hub 26 and the outer needle 24, and with the needle tip 16 of the inner needle 18 projecting from the outer needle 24, the inner needle unit 152 and the outer needle unit 14 are attached to each other. Also, in this attached state, the resin member 146 of the protector 142 is connected to the flange part 46 of the outer needle hub 26.

Figure 29:
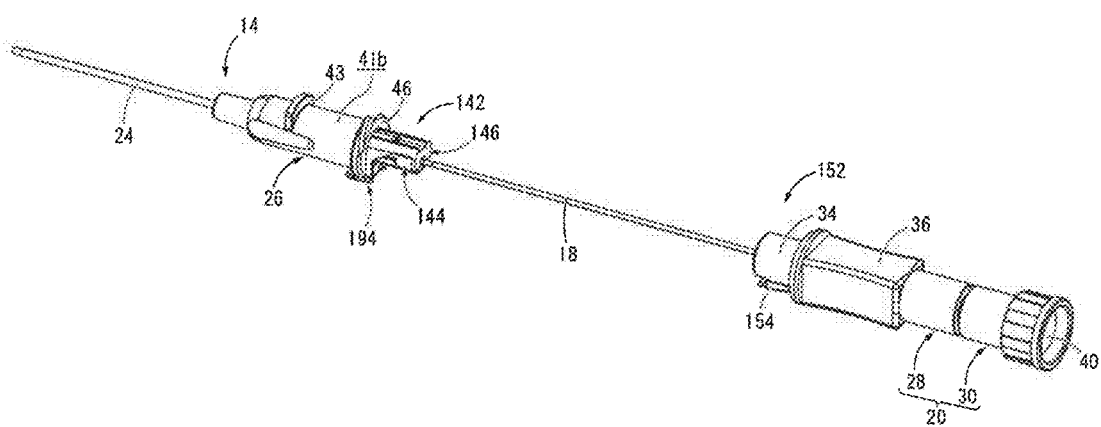
FIG. 29 is a perspective view of the indwelling needle assembly shown in FIG. 20, which illustrates the state of completion of needle-tip protection where an inner needle unit has been pulled out of an outer needle unit.

With such indwelling needle assembly 140, as shown in FIG. 29, by the inner needle 18 being pulled out of the outer needle 24, the needle tip 16 is housed within the protector 142, and roughly simultaneously, the needle-tip protection part 204 of the resin member 146 is configured to move in the direction of approaching the inner needle 18 and to cover the distal end side of the inner needle 18 on the needle axis.

Figure 30A:
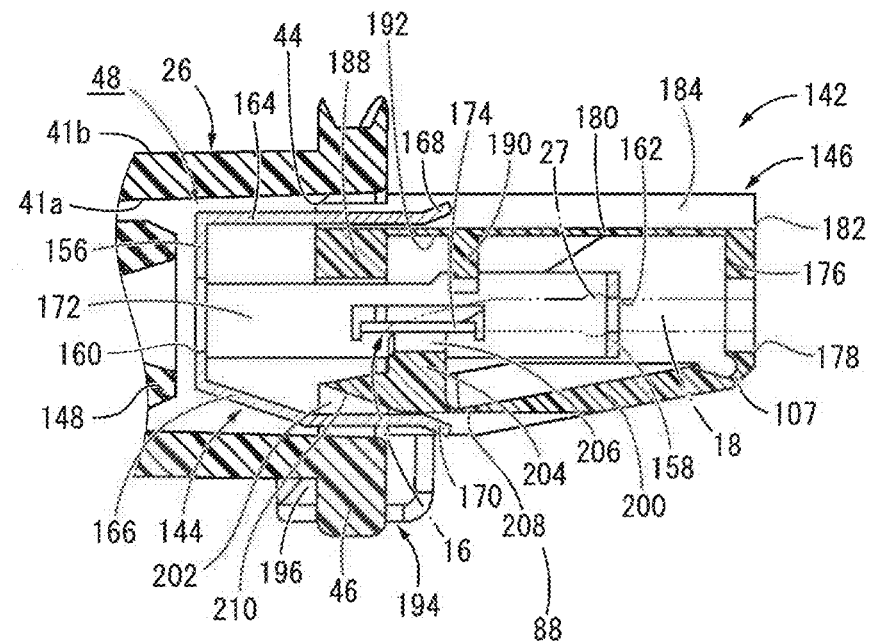

Described more specifically, in the state shown in FIG. 30A, the large-diameter part 27 of the inner needle 18 is positioned in the front beyond the rear wall 158 of the metal member 144. When the inner needle 18 is moved further to the pulling-out side from that state, the large-diameter part 27 is engaged with the rear wall 158 in the axial direction at the rim of the opening of the inner-needle insertion hole 162, and the metal member 144 undergoes relative movement near to the outer needle hub 26 and the resin member 146 together with the inner needle 18. Therefore, in the present embodiment, the rear wall 158 of the metal member 144 constitutes the inner-needle engaging part that is engaged with the inner needle 18 when the inner needle 18 is pulled out.

Figure 30B:
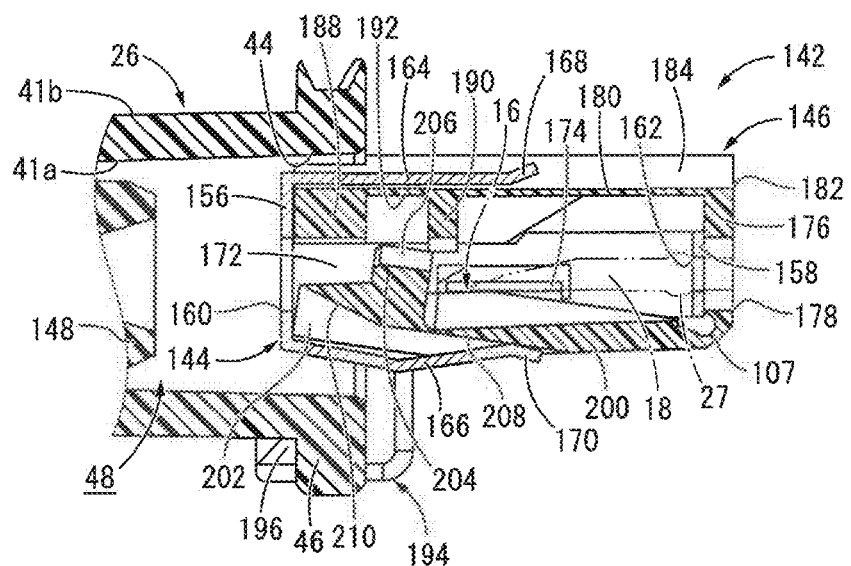

Then, by the metal member 144 being moved to the pulling-out side relative to the resin member 146 by the prescribed amount or more, as shown in FIG. 30B, the contact between the locking pieces 174, 174 of the metal member 144 and the contact retaining parts 206, 206 of the resin member 146 is released. By so doing, the retaining wall 200 of the resin member 146 is deformed at the hinge part 107 due to elasticity of the lower elastic wall 166 of the metal member 144, and displaces so as to approach the sliding contact wall 180, so that the needle-tip protection part 204 of the resin member 146 moves in the direction of approaching the needle axis of the inner needle 18 (the inner needle direction). As a result, the needle-tip protection part 204 is positioned on the needle axis of the inner needle 18 so as to cover its distal end side, so that the needle-tip protection part 204 limits movement of the inner needle 18 to the distal end side.

Concurrently, due to displacement of the retaining wall 200 of the resin member 146 in the direction of approaching the inner needle 18, the distal end portion 202 of the retaining wall 200 is separated from the inner surface 41a of the outer needle hub 26, thereby releasing engagement of the protector 142 with the outer needle hub 26. Specifically, with the protector 142 housing the needle tip 16 of the inner needle 18, the vertical dimension becomes smaller due to displacement of the retaining wall 200. This makes the protector 142 movable downward with respect to the outer needle hub 26. Moreover, the amount of downward movement allowed for the protector 142 with respect to the outer needle hub 26 is made larger than the engagement margin of the locking claws 196, 196 of the resin member 146 with the flange part 46 of the outer needle hub 26. Therefore, by moving the inner needle unit 152 including the protector 142 downward with respect to the outer needle unit 14 including the outer needle hub 26 so as to release engagement of the locking claws 196, 196 with the flange part 46 while pulling the inner needle unit 152 out of the outer needle unit 14, it is possible to detach the inner needle unit 152 from the outer needle unit 14.

Here, the sloping parts 198, 198 are provided to the proximal end side of the locking claws 196, 196 in the needle axis direction. This makes it possible to detach the inner needle unit 152 from the outer needle unit 14 simply by horizontally pulling out the inner needle unit 152, without the operation to move the inner needle unit 152 downward with respect to the outer needle unit 14.

In the present embodiment, during the displacement of the retaining wall (the urging part) 200 in the direction of approaching the inner needle 18, the connecting parts (the outer-needle-hub engaging parts) 194, 194 and the retaining wall 200 do not displace integrally with each other, but displace independently of each other.

With the indwelling needle assembly 140 of the present embodiment having the structure described above as well, the inner needle 18 is pulled out with the needle-tip protection part 204 being remote from the inner needle 18. Thus, it is possible to keep sliding resistance during pulling out the inner needle 18 to a minimum, thereby avoiding the trouble of the outer needle 24 being pulled out together with the inner needle 18.

In particular, with the indwelling needle assembly 140 of the present embodiment, the protector 142, which protects the needle tip 16 of the inner needle 18 after pulling it out, partially comprises the resin member 146. Thus, in comparison with the case where the protector 142 is entirely made of metal, reduced weight, reduced cost, improvement in degree of freedom of structure, or the like are achieved.

Besides, the engagement structure with the outer needle hub 26, the needle-tip protection part 204 for covering the distal end side of the needle tip 16, the contact retaining part 206 for retaining the needle-tip protection part 204 at a position away from the needle axis, or the like, namely, the parts which do not require a large elasticity per se, are constituted by the resin member 146. Thus, the use of resin will not have an adverse effect on the operation for protecting the needle tip, durability, or the like.

Moreover, since the needle-tip protection part 204 is urged in the direction of approaching the inner needle 18 by the lower elastic wall 166 made of metal, the required urging force can be obtained with excellent reliability. Furthermore, the rear wall 158 (the inner-needle engaging part), which is the rim of the opening of the inner-needle insertion hole 162 in which the inner needle 18 is inserted, is formed by the metal member 144 for which the dimensional error is smaller than that of the resin member 146. Thus, it is possible to stably obtain the inner-needle insertion hole 162 with high dimensional precision, and to enable the rim of the opening of the inner-needle insertion hole 162 to be engaged with the large-diameter part 27 of the inner needle 18 in the axial direction in a more reliable manner. Specifically, the inner-needle engaging part for limiting the amount of movement of the inner needle 18 to the pulling-out side requires high dimensional precision in order to allow the inner needle 18 to be inserted into the metal member 144 while engaging the inner needle 18 in the axial direction during pulling out the inner needle 18. Here, in the present embodiment, by providing the inner-needle engaging part to the metal member 144, which readily achieves high dimensional precision in comparison with the resin member 146, it is possible to stably prevent the inner needle 18 from being detached in a desired manner.

Furthermore, the sliding contact wall 180 and the retaining wall 200 for limiting or permitting movement of the needle-tip protection part 204 in the direction of approaching the inner needle 18 are provided to the resin member 146, while the upper and lower elastic walls 164, 166 for urging the sliding contact wall 180 and the retaining wall 200 in the direction of approaching the inner needle 18 are provided to the metal member 144. This makes it possible to stably obtain sufficient urging force for the movement of the needle-tip protection part 204 by means of the elastic walls 164, 166 made of metal, and concurrently, in comparison with the case where the protector 142 is entirely made of metal, reduced weight, reduced cost, and additionally excellent degree of freedom of shape or the like can be achieved by using the resin member 146.

With the indwelling needle assembly 140 before protection of the needle tip, vertical movement of the protector 142 with respect to the outer needle hub 26 is limited sufficiently to a minimum, so that the protector 142 and the outer needle hub 26 are stably engaged and secured. Besides, with the connecting parts 194, 194 that constitute the engagement structure of the protector 142 with the outer needle hub 26, the slope wall 154 of the inner needle hub 20 is overlapped from the proximal side. Accordingly, deformation of the connecting parts 194, 194 is limited by the slope wall 154, so that engagement of the protector 142 with the outer needle hub 26 is even less likely to be released. In addition, in order to reduce pain during the puncture, the inner needle 18 is inserted such that the needle tip inclined surface 16a is positioned on the opposite side to the body skin on the circumference. Thus, the slope wall 154 of the inner needle hub 20 arranged on the opposite side to the needle tip inclined surface 16a on the circumference is positioned on the body skin side during the puncture. In this way, the engaged portion of the protector 142 with the outer needle hub 26 is arranged on the opposite side to the needle tip inclined surface 16a of the inner needle 18, which faces upward, on the circumference. Therefore, when picking up the inner needle hub 20 for operation, the connecting parts 194, 194, namely, the engaged portion of the protector 142 with the outer needle hub 26, are less likely to be touched without intention, thereby avoiding unexpected release of engagement of the protector 142 with the outer needle hub 26.

Besides, when the metal member 144 and the resin member 146 are attached, by the locking pieces 174, 174 of the metal member 144 and the contact retaining parts 206, 206 of the resin member 146 being in contact with each other, it is possible to retain the needle-tip protection part 204 at a position remote from the needle axis of the inner needle 18 in advance. With this arrangement, the inner needle 18 is readily inserted into the protector 142 during production of the indwelling needle assembly 140, and the production becomes easy.

Moreover, when the metal member 144 and the resin member 146 are attached in the axial direction, the sliding contact wall 180 and the retaining wall 200 of the resin member 146 are guided by the upper and lower guide parts 168, 170 of the metal member 144. Thus, it is possible to readily insert the resin member 146 between the opposed upper and lower elastic walls 164, 166 of the metal member 144.

Figure 31:
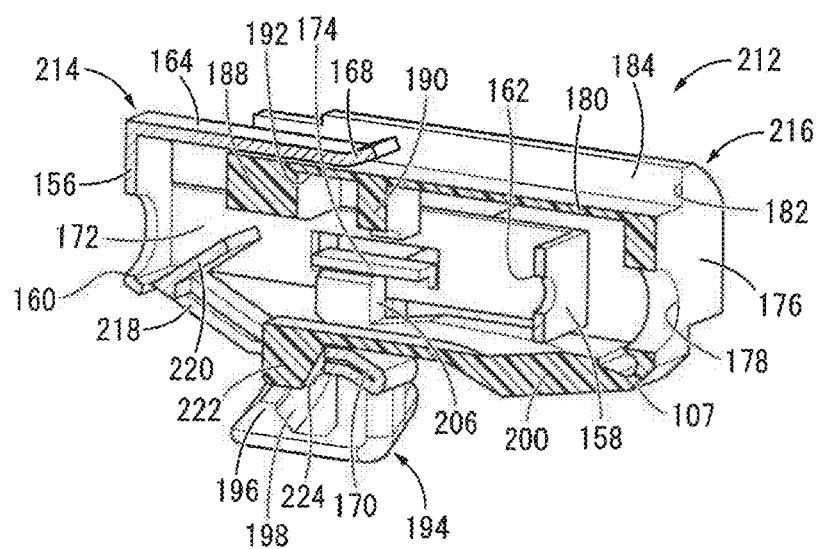
FIG. 31 is a perspective cross sectional view of a safety mechanism part constituting an indwelling needle assembly as a fourth embodiment of the present invention.

Next, FIG. 31 depicts a protector 212 serving as a safety mechanism part that constitutes an indwelling needle assembly as a fourth embodiment of the present invention. Like the third embodiment, the protector 212 is also constituted by a metal member 214 and a resin member 216, and a lower elastic wall 218 of the metal member 214 is provided with a needle-tip protection part 220. In the initial state where the inner needle 18 is inserted, the needle-tip protection part 220 is kept remote from the inner needle 18. Besides, a locking convex part 222 projecting radially outward from the distal end of the retaining wall 200 is inserted into a passage hole 224 provided to the lower elastic wall 218. Accordingly, with the indwelling needle assembly assembled, the connecting parts (the outer-needle-hub engaging parts) 194, 194 are engaged with the flange part (46) provided to the outer surface (41b) of the outer needle hub (26), while the locking convex part 222 provided to the resin member 216 extends to the inside of the outer needle hub (26). Therefore, in the present embodiment, the locking convex part 222 constitutes the engaging-part opposing wall that is in opposition to the connecting parts (the outer-needle-hub engaging parts) 194, 194 and extends to the inside of the outer needle hub (26).

Figure 32:
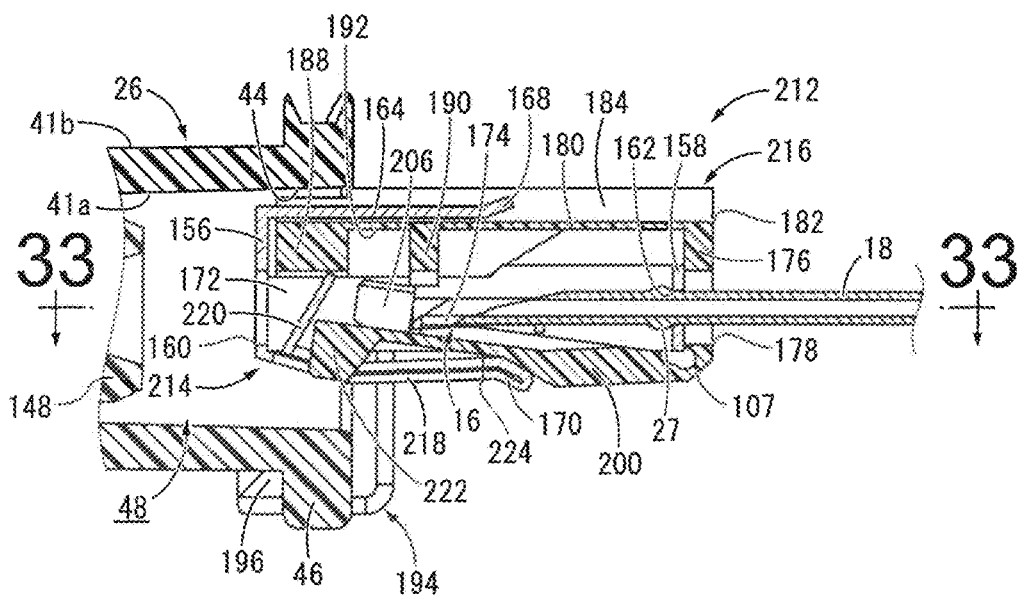
FIG. 32 is an enlarged vertical cross sectional view of a principal part of the indwelling needle assembly equipped with the safety mechanism part shown in FIG. 31 in the state of completion of needle-tip protection, taken along line 32-32 of FIG. 33.
Figure 33:
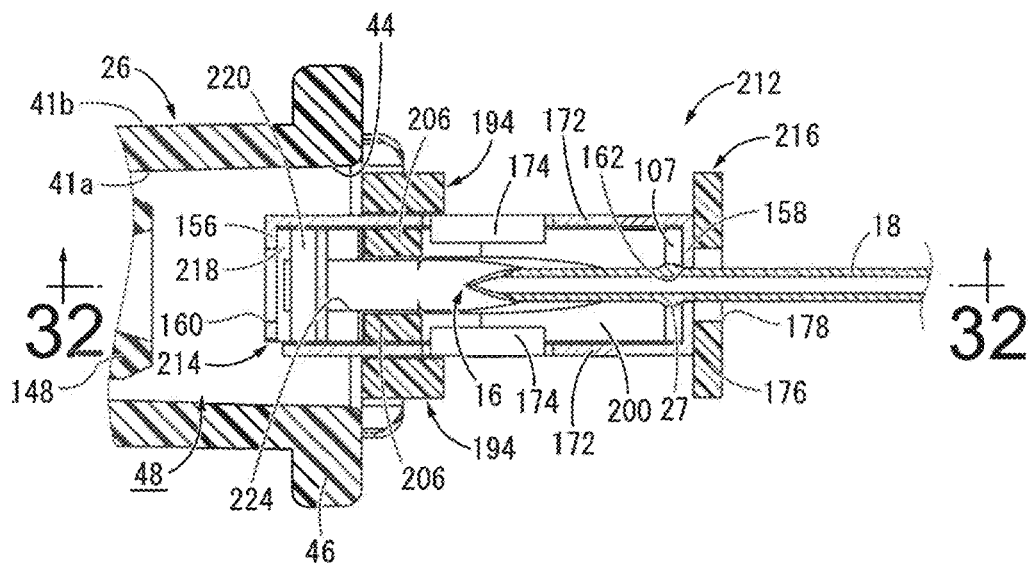
FIG. 33 is a cross sectional view taken along line 33-33 of FIG. 32.

As shown in FIGS. 32 and 33, by pulling out the inner needle 18, engagement of the locking pieces 174, 174 with the contact retaining parts 206, 206 is released, whereby the lower elastic wall 218 and the retaining wall 200 displace based on urging force of the lower elastic wall 218. As a result, the needle-tip protection part 220 provided to the lower elastic wall 218 covers and protects the needle tip 16 of the inner needle 18, while the locking convex part 222 becomes separated from the inner surface 41a of the outer needle hub 26, making it possible to release engagement of the protector 212 with the outer needle hub 26.

In the present embodiment as well, when the inner needle 18 is pulled out, the needle-tip protection part 220 and the inner needle 18 do not directly slide with respect to each other. This will reduce sliding resistance, thereby decreasing a risk of the outer needle (24) being pulled out together with the inner needle 18. Also, as described in the present embodiment, the needle-tip protection part 220 may be provided to the metal member 214 side. This makes it possible to improve protection effect of the needle tip 16 of the inner needle 18.

Figure 34:
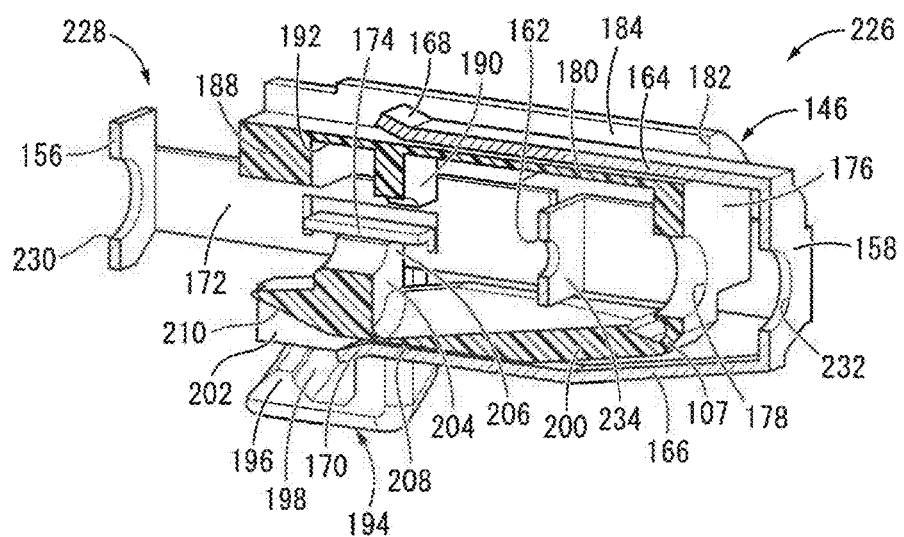
FIG. 34 is a perspective cross sectional view of a safety mechanism part constituting an indwelling needle assembly as a fifth embodiment of the present invention.
Figure 35:
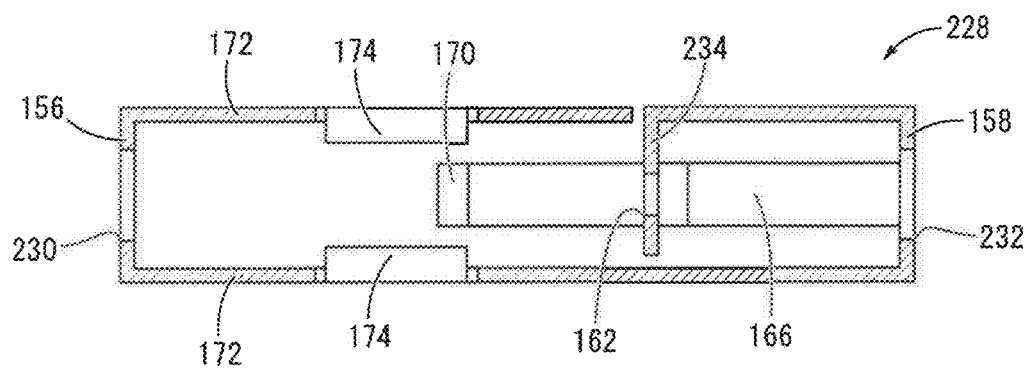
FIG. 35 is a vertical cross sectional view of a metal member constituting the safety mechanism part shown in FIG. 34.

Next, FIG. 34 depicts a protector 226 serving as a safety mechanism part that constitutes an indwelling needle assembly as a fifth embodiment of the present invention. The protector 226 is constituted by a metal member 228 shown in FIGS. 34 and 35 being attached to the resin member 146 which is the same as the one described in the third embodiment.

With the metal member 228 of the present embodiment, an inner-needle front through hole 230 and an inner-needle rear through hole 232 respectively provided to the front wall 156 and the rear wall 158 have inside diameter dimensions larger than the maximum outside diameter dimension of the large-diameter part 27 of the inner needle 18. Meanwhile, in the lengthwise medial portion of the metal member 228, there is provided a middle wall 234, which includes the inner-needle insertion hole 162 at its center. With this arrangement, when the inner needle 18 is pulled out, the large-diameter part 27 of the inner needle 18 and the middle wall 234 are engaged, so that the metal member 228 displaces rearward with respect to the resin member 146. That is, in the present embodiment, the middle wall 234 provided to the lengthwise medial portion of the metal member 228 constitutes the inner-needle engaging part that is engaged with the inner needle 18 during pulling out of the inner needle 18.

In the present embodiment, the upper elastic wall 164 and the lower elastic wall 166 extend from the respective upper and lower ends of the rear wall 158 toward the distal end side in the needle axis direction. Thus, the upper elastic wall 164, the rear wall 158, and the lower elastic wall 166 constitute a plate spring having a roughly U-letter shape, and the distal end portions thereof, which are on the opening side of the plate spring, extend toward the distal end side in the needle axis direction.

With the protector 226 of the present embodiment having such structure as well, sliding resistance will be kept to a minimum during pulling out of the inner needle 18, thereby decreasing a risk of the outer needle (24) being pulled out of the skin of the patient together with the inner needle 18.

Figure 36:
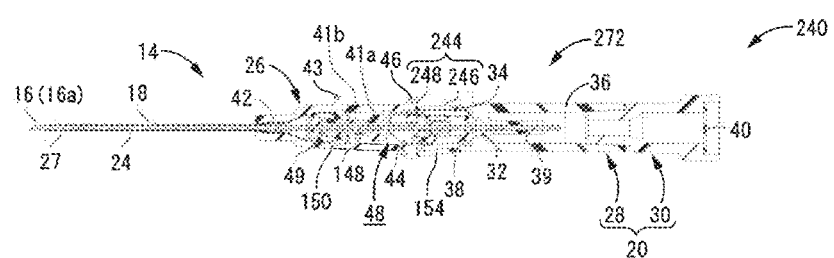
FIG. 36 is a vertical cross sectional view of an indwelling needle assembly as a sixth embodiment of the present invention, taken along line 36-36 of FIG. 38.
Figure 37:
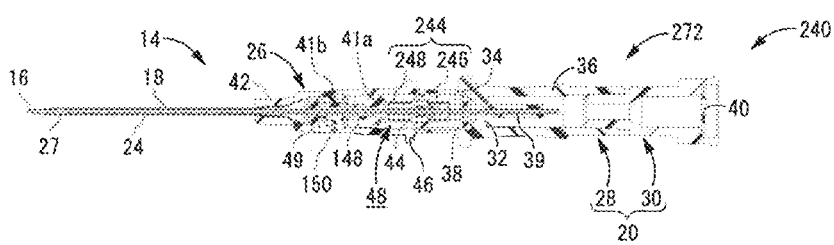
FIG. 37 is another vertical cross sectional view of the indwelling needle assembly shown in FIG. 36, taken along line 37-37 of FIG. 38.
Figure 38:
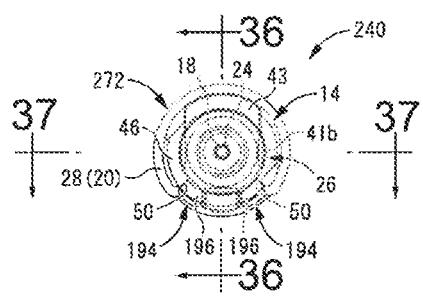
FIG. 38 is a left side view of the indwelling needle assembly shown in FIG. 36.
Figure 39:
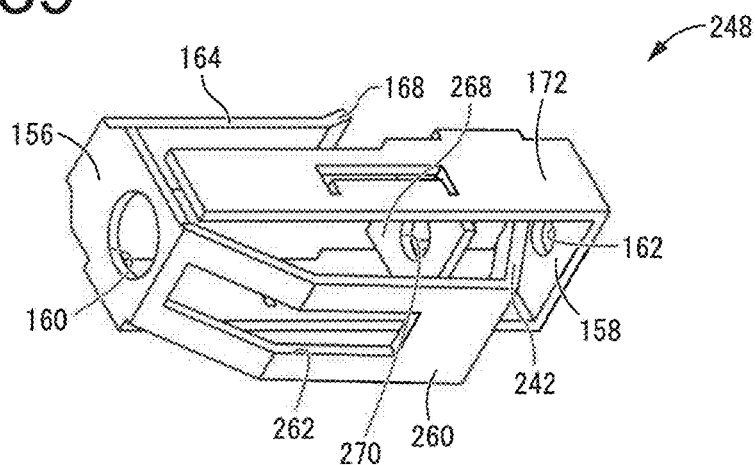
FIG. 39 is a perspective view of a second protector member constituting the indwelling needle assembly shown in FIG. 36.
Figure 40:
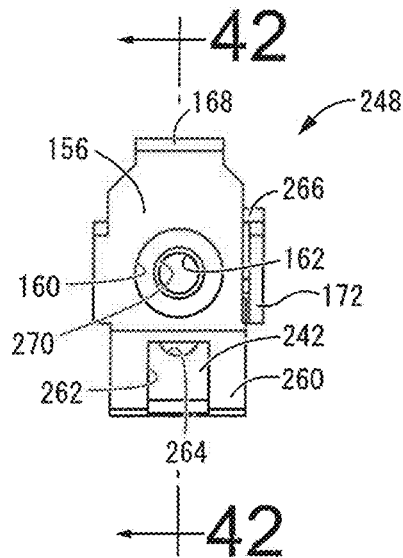
FIG. 40 is a left side view of the second protector member shown in FIG. 39.
Figure 41:
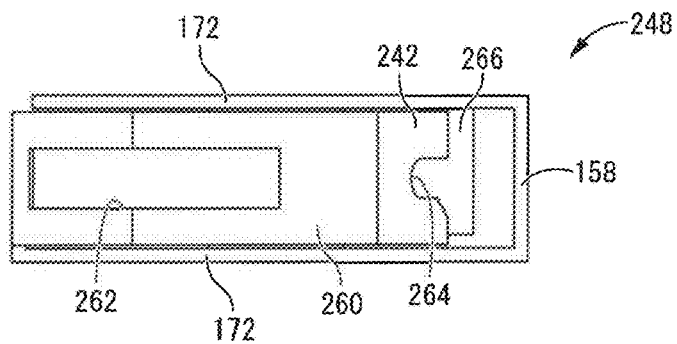
FIG. 41 is a bottom plane view of the second protector member shown in FIG. 39.
Figure 42:
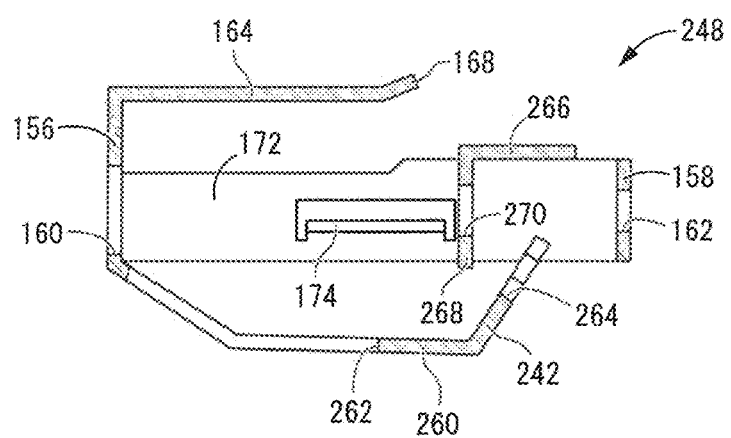
FIG. 42 is a cross sectional view taken along line 42-42 of FIG. 40.
Figure 43:
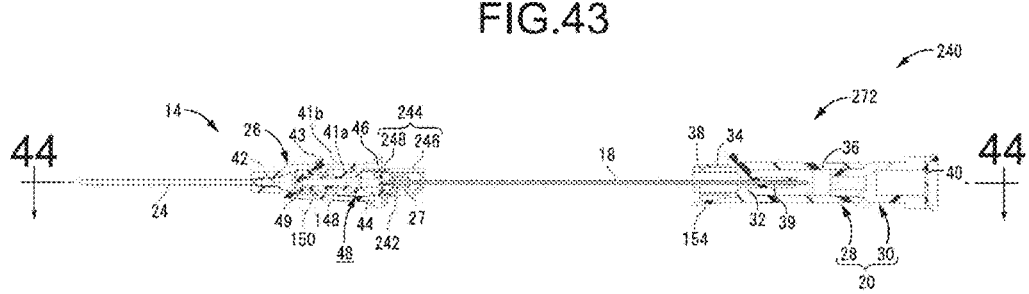
FIG. 43 is a vertical cross sectional view illustrating the state in the middle of pulling an inner needle out of the indwelling needle assembly shown in FIG. 36.
Figure 44:
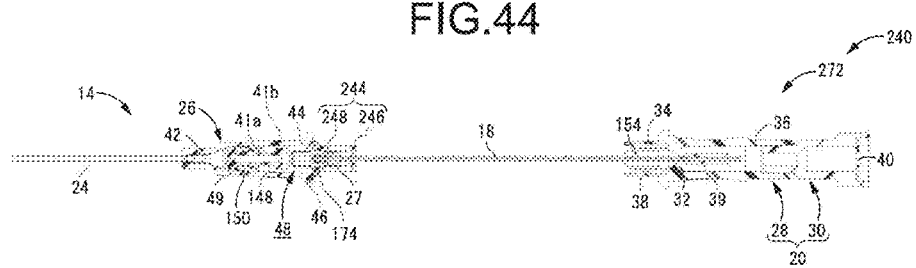
FIG. 44 is a cross sectional view taken along line 44-44 of FIG. 43.

Next, FIGS. 36 to 38 depict an indwelling needle assembly 240 as a sixth embodiment of the present invention. With the indwelling needle assembly 240 of the present embodiment, when the inner needle 18 is pulled out, a needle restricting part 242 (see FIG. 39 etc.) provided to the urging part displaces in the direction of approaching the inner needle 18 so as to come into contact with the side surface of the inner needle 18, thereby preventing the needle tip 16 of the inner needle 18 from protruding from a protector 244 serving as a safety mechanism part.

The protector 244 of the present embodiment has a structure in which a first protector member 246 and a second protector member 248 are attached to each other. The first protector member 246 and the second protector member 248 are movable relative to each other in the needle axis direction of the inner needle 18.

Figure 45:
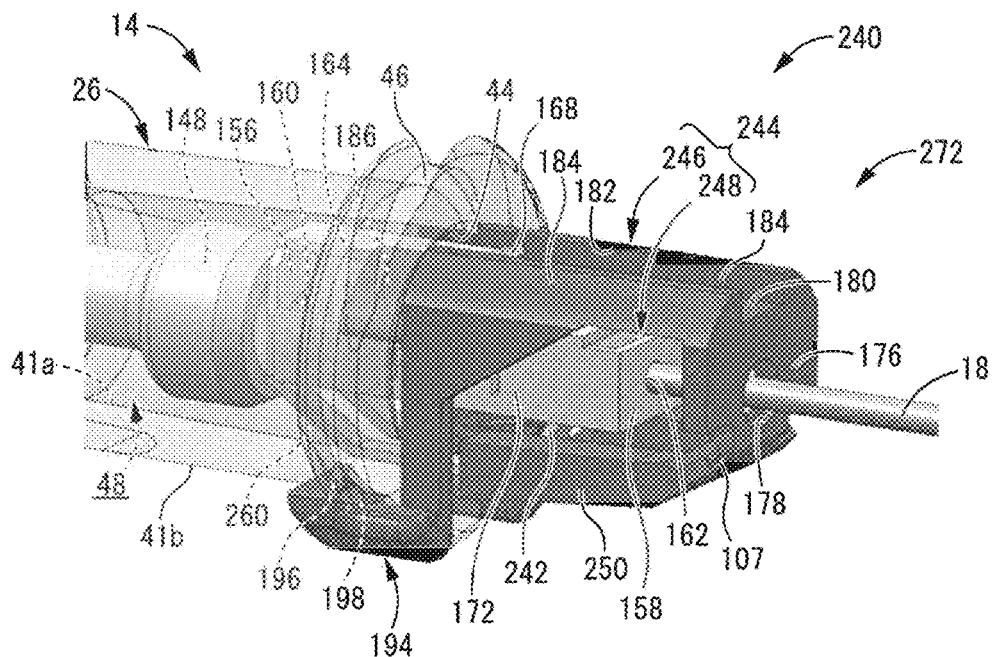
FIG. 45 is a view suitable for explaining a principal part of the indwelling needle assembly shown in FIG. 43.

The first protector member 246 is a component made of rigid synthetic resin. As shown in FIG. 45, 46 or the like described later, the structure of the first protector member 246 is similar to that of the resin member 146 in the third embodiment, but is different in the structure of a retaining wall 250 provided to the lower end portion of the vertical wall 176.

Specifically, the retaining wall 250 of the present embodiment includes at its widthwise center portion a passage window 252 that extends from the medial portion in the needle axis direction to the proximal end side. The passage window 252 penetrates the retaining wall 250 in the plate thickness direction, and has a generally rectangular shape in plan view. The inner peripheral surfaces on the distal end side and the proximal end side of the passage window 252 are sloping surfaces that gradually slope downward toward the distal end side.

Moreover, at the distal end portion of the retaining wall 250, there are integrally formed a pair of contact retaining parts 254, 254 that project upward from the widthwise both ends thereof. The contact retaining parts 254, 254 each have a generally rectangular block shape, and are positioned so as to be roughly in opposition in the vertical direction to the recess 192 that is positioned between the guide projection 188 and the positioning projection 190. Besides, at the distal end portion of the retaining wall 250, a center wall 256 is provided so as to extend from the widthwise center to the distal end side, and the center wall 256 is positioned between the connecting parts 194, 194 serving as the outer-needle-hub engaging parts that are opposed in the width direction. Furthermore, at the distal end of the center wall 256, an inside mating claw 258 is integrally formed so as to project downward. That is, the inside mating claw 258 is positioned between the locking claws 196, 196 that are provided to the respective distal ends of the connecting parts 194, 194 and are opposed in the width direction. As will be described later, in the case where the locking claws 196, 196 and the inside mating claw 258 clasp and retain the peripheral wall of the outer needle hub 26, the locking claws 196, 196 and the inside mating claw 258 are configured to be in opposition to each other at the position deviated in the circumferential direction. Therefore, in the present embodiment, the inside mating claw 258 constitutes the engaging-part opposing wall that is in opposition to the connecting parts 194, 194 (the locking claws 196, 196) serving as the outer-needle-hub engaging parts.

Meanwhile, the second protector member 248 is a component made of metal. As shown in FIGS. 39 to 42, the structure of the second protector member 248 is similar to that of the metal member 144 in the third embodiment, but is different in the structure of a lower elastic wall 260 provided to the lower end portion of the front wall 156. In FIGS. 39 to 42, the second protector member 248 is shown in the attached state to the first protector member 246, where the lower elastic wall 260 is elastically deformed downwardly in comparison with a free state where no external force is exerted thereon.

Figure 47:
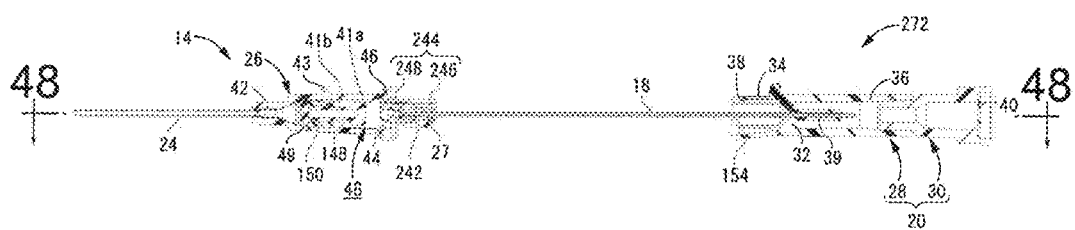
FIG. 47 is a vertical cross sectional view illustrating the state where the inner needle has been pulled out of the indwelling needle assembly shown in FIG. 36 so as to move a contact part.

Specifically, with the lower elastic wall 260 of the present embodiment, the distal end portion and the proximal end portion mutually slope with respect to the medial portion in the needle axis direction. When attached to the first protector member 246 as shown in FIGS. 39 to 42, in comparison with the free state, the lower elastic wall 260 elastically deforms downwardly, so that the medial portion in the needle axis direction extends in the direction roughly orthogonal to the front wall 156, while the distal end portion of the lower elastic wall 260 in the needle axis direction slopes upward as it goes to the distal end side and is connected to the lower end portion of the front wall 156. On the other hand, in the free state where no external load is exerted thereon, the lower elastic wall 260 is positioned on the upper side than the state shown in FIGS. 39 to 42. As shown in FIG. 47 or the like described later, the medial portion of the lower elastic wall 260 in the needle axis direction slightly slopes upwardly toward the proximal end side. Besides, the proximal end portion of the lower elastic wall 260 in the needle axis direction slopes upward as it goes to the proximal end side, and the proximal end portion of the lower elastic wall 260 in the needle axis direction (the projecting distal end portion) constitutes the needle restricting part 242 for preventing the inner needle 18 from protruding from the protector 244 when the inner needle 18 is pulled out.

Moreover, in the widthwise center portion of the lower elastic wall 260, a lock window 262 extends from the distal end portion to the medial portion in the needle axis direction so as to perforate the lower elastic wall 260 in the plate thickness direction. Additionally, at the projecting distal end (the proximal end portion in the needle axis direction) of the needle restricting part 242, a notch 264 is formed in the widthwise center portion so as to open upward (to the inner needle 18 side) in a roughly U-letter shape. The opening width dimension of the notch 264 is made smaller than the outside diameter dimension of the large-diameter part 27 of the inner needle 18, while being made larger than the outside diameter dimension of the portion of the inner needle 18 except the large-diameter part 27.

Furthermore, with the one locking wall 172 (the right one in FIG. 40), a reinforcing upper wall 266 is integrally formed with the upper end in the axially medial portion of the locking wall 172, so as to project inward in the direction of opposition of the locking walls 172, 172. The reinforcing upper wall 266 has a generally rectangular plate shape, and to the distal end thereof, integrally formed is a reinforcing distal end wall 268 serving as the insertion wall that extends downward. The reinforcing distal end wall 268 has a generally rectangular plate shape, and extends in the direction orthogonal to the needle axis direction so as to be in opposition to the front wall 156 and the rear wall 158 with a prescribed distance in between in the needle axis direction. In the center of the reinforcing distal end wall 268, formed is a circular insertion hole 270 in which the inner needle 18 is inserted, and the inside diameter dimension of the insertion hole 270 is made larger than the outside diameter dimension of the large-diameter part 27 of the inner needle 18. Besides, the reinforcing distal end wall 268 is positioned to the proximal end side beyond the locking pieces 174, 174 in the needle axis direction. Also, the distal end (the proximal end portion in the needle axis direction) of the needle restricting part 242 of the lower elastic wall 260 is inserted between the opposed reinforcing distal end wall 268 and rear wall 158 in the needle axis direction.

As described above, the second protector member 248 includes a plurality of insertion walls (the front wall 156, the rear wall 158, and the reinforcing distal end wall 268) in which respective insertion holes of the inner needle 18 (the inner-needle through hole 160, the inner-needle insertion hole 162, and the insertion hole 270) are formed. Accordingly, when the inner needle 18 is inserted, a tilt of the inner needle 18 and the second protector member 248 is limited. By so doing, when the inner needle 18 is pulled out of the outer needle 24, it is possible to prevent the inner needle 18 from tilting with respect to the second protector member 248 and, for example, strongly rubbing the inner surfaces of the insertion holes 160, 162, 270 or the like so as to generate a large resistance due to friction.

Figure 46:
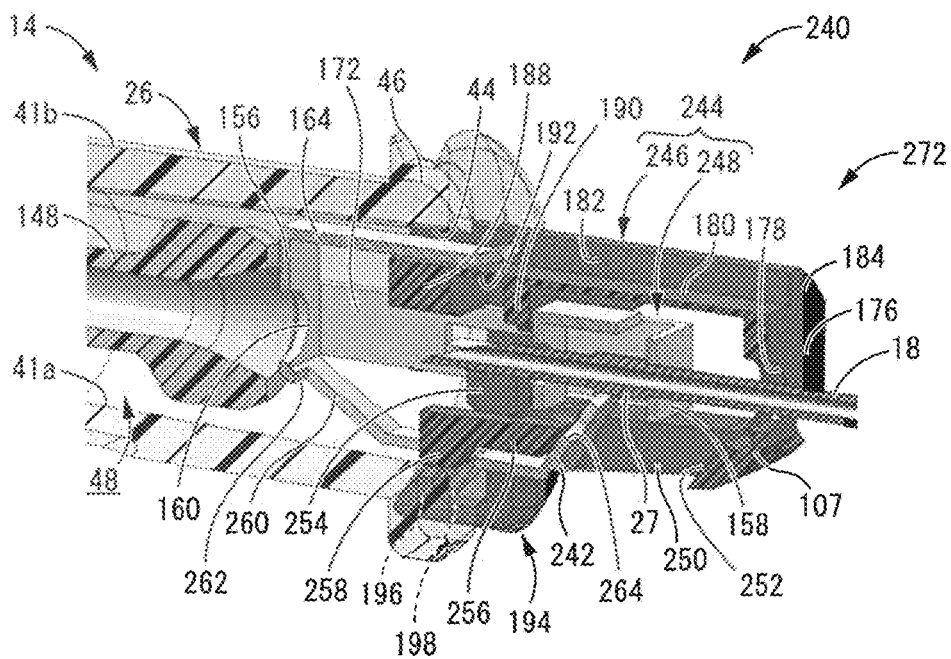
FIG. 46 is a vertical cross sectional view of the indwelling needle assembly shown in FIG. 45.

As shown in FIGS. 45 and 46 described later, such first protector member 246 and second protector member 248 are attached to each other, so as to constitute the protector 244 of the present embodiment.

Specifically, the sliding contact wall 180 and the center wall 256 of the first protector member 246 are inserted between the opposed faces of the upper and lower elastic walls 164, 260 of the second protector member 248 in the needle axis direction and attached thereto. By so doing, the upper elastic wall 164 is inserted into the upper concave groove 182 and overlapped on the sliding contact wall 180, while the lower elastic wall 260 is overlapped on the center wall 256 from below. The reinforcing distal end wall 268 and the rear wall 158 of the second protector member 248 are positioned between the opposed positioning projection 190 and vertical wall 176 of the first protector member 246 in the needle axis direction. With this arrangement, the distal end of the needle restricting part 242, which is the proximal end portion of the lower elastic wall 260, is inserted between the reinforcing distal end wall 268 and the rear wall 158 through the passage window 252 provided to the retaining wall 250, while the inside mating claw 258 provided to the distal end of the center wall 256 projects downward through the lock window 262 provided to the lower elastic wall 260.

In this way, by the upper elastic wall 164 being inserted into the upper concave groove 182, in the case where the first protector member 246 and the second protector member 248 rotate relative to each other, for example, the upper elastic wall 164 comes into contact with the both upper side walls 184, 184 of the upper concave groove 182, so as to prevent relative rotation of the first protector member 246 and the second protector member 248. Similarly, by the needle restricting part 242 coming into contact with the inner peripheral surface of the passage window 252, or by the inside mating claw 258 coming into contact with the inner peripheral surface of the lock window 262, relative rotation of the first protector member 246 and the second protector member 248 is prevented.

In the initial state shown in FIG. 36 or the like, the guide projection 188 provided to the distal end part of the sliding contact wall 180 is inserted between the upper elastic wall 164 and the pair of locking walls 172, 172 in the vertical direction, and the positioning projection 190 is inserted to the upper part between the opposed locking walls 172, 172. Meanwhile, the contact retaining parts 254, 254 provided to the widthwise both ends of the distal end of the retaining wall 250 are in contact with the locking pieces 174, 174 projecting inward in the direction of opposition of the locking walls 172, 172 from below. By so doing, the locking walls 172, 172 are clasped and retained in the vertical direction by the guide projection 188, the positioning projection 190, and the contact retaining parts 254, 254.

Therefore, the structure in which the guide projection 188 is inserted between the upper elastic wall 164 and the pair of locking walls 172, 172, the structure in which the locking walls 172, 172 are clasped and retained in the vertical direction by the guide projection 188, the positioning projection 190, and the contact retaining parts 254, 254, or the like are able to prevent the first protector member 246 and the second protector member 248 from relatively tilting in the vertical direction with respect to the needle axis direction. Of course, in the present embodiment, as the tilting prevention structure for the first protector member 246 and the second protector member 248, in addition to the above-described contact structure of the upper elastic wall 164 and the sliding contact wall 180, or the contact structure of lower elastic wall 260 and the center wall 256, there may be the structure in which the guide projection 188 is inserted between the pair of locking walls 172, 172 and the upper elastic wall 164, the structure in which the guide projection 188 is in contact with the locking wall 172, the structure in which the positioning projection 190 is inserted between the pair of locking walls 172, 172, the structure in which the contact retaining part 254 is in contact with the locking piece 174, or the like. Accordingly, at least one of, preferably a plurality of the above-mentioned structures can suitably be adopted as the mechanism for limiting the tilting of the first protector member 246 and the second protector member 248.

Therefore, with the protector 244 of the present embodiment, the structure for preventing relative tilting and the structure for preventing relative rotation constitute a fixing structure for preventing relative tilting of the first protector member 246 and the second protector member 248. In this embodiment in particular, the second protector member 248 that constitutes the protector 244 includes the insertion walls 156, 158, 268 having the respective insertion holes 160, 162, 270 that are arranged with a prescribed distance in between in the needle axis direction. Thus, when the inner needle 18 is inserted, tilting of the inner needle 18 relative to the second protector member 248, and hence relative to the entire protector 244 will be prevented. With this arrangement, when the inner needle 18 is pulled out of the outer needle 24, it is possible to decrease a risk that the inner needle 18 may tilt to be in contact with the inner surfaces of the insertion holes 160, 162, 270 or the like so as to generate a large resistance. It would also be acceptable to recognize the vertical wall 176 of the first protector member 246 to be the insertion wall, and the passage hole 178 to be the insertion hole in which the inner needle 18 is inserted. However, in the present embodiment, as to the insertion hole for limiting the tilting of the second protector member 248 relative to the inner needle 18, it is acceptable as long as two of the insertion holes 160, 162, 270 of the second protector member 248 are adopted. Also, in the structure in which the first protector member 246 and the second protector member 248 are prevented from tilting with respect to each other, it is sufficient as long as the total number of the insertion holes provided to the first protector member 246 and the second protector member 248 is two at the least.

By the contact retaining parts 254, 254 being in contact from below with the locking pieces 174, 174, the lower elastic wall 260, which is in contact from below with the center wall 256 that is positioned below the contact retaining parts 254, 254, elastically deforms downward. That is, in the initial state, the lower elastic wall 260 (the needle restricting part 242) is urged upward (to the inner needle 18 side) based on elastic recovery action, and such urging force is also exerted on the center wall 256 of the first protector member 246 or the like. However, since the locking pieces 174, 174 and the contact retaining parts 254, 254 are in contact with each other, elastic recovery motion of the lower elastic wall 260 in the upward direction is prevented. Therefore, in the present embodiment, the lower elastic wall 260 (the needle restricting part 242) constitutes the urging part that is urged in the direction of approaching the inner needle 18.

With respect to the attachment of the first protector member 246 and the second protector member 248, no limitation is imposed as to the specific step or method thereof. For example, the guide projection 188 is inserted between the upper elastic wall 164 and the locking walls 172, 172. Meanwhile, the positioning projection 190 of the first protector member 246 and the contact retaining parts 254, 254 are separated from each other, and then the locking walls 172, 172 and the reinforcing upper wall 266 are inserted therebetween. Moreover, the lower elastic wall 260 of the second protector member 248 is elastically deformed downwardly and attached so as to cover the center wall 256 from below. Accordingly, it is possible to insert the needle restricting part 242 into the passage window 252 from below, as well as to insert the inside mating claw 258 into the lock window 262 from above.

With the protector 244 as described above, the first protector member 246 and the second protector member 248 are relatively movable in the needle axis direction. Specifically, the upper elastic wall 164 is movable in the needle axis direction within the upper concave groove 182, while the needle restricting part 242 is movable in the needle axis direction within the passage window 252, and the inside mating claw 258 is movable in the needle axis direction within the lock window 262. When the second protector member 248 is moved to the proximal end side with respect to the first protector member 246, by the rear wall 158 of the second protector member 248 coming into contact with the vertical wall 176 of the first protector member 246, for example, movement of the second protector member 248 is restricted. Also, when the second protector member 248 is moved to the distal end side with respect to the first protector member 246, by the reinforcing upper wall 266 or the reinforcing distal end wall 268 coming into contact with the positioning projection 190, for example, movement of the second protector member 248 is restricted. In the initial state, the second protector member 248 is attached so as to be positioned at the traveling end on the distal end side with respect to the first protector member 246.

Such protector 244 is externally mounted about the inner needle 18. Specifically, by the inner needle 18 being inserted into the insertion holes 160, 162, 178, 270 provided to the protector 244, the protector 244 is made movable in the needle axis direction with respect to the inner needle 18. Then, by the protector 244 being externally placed about the inner needle 18 and by the proximal end of the inner needle 18 being secured to the inner needle hub 20, an inner needle unit 272 of the present embodiment is constituted.

Furthermore, by the inner needle unit 272 and the outer needle unit 14 being attached, the indwelling needle assembly 240 of the present embodiment is constituted. Specifically, the locking claws 196, 196 provided to the distal ends of the connecting parts 194, 194 of the protector 244 are engaged with the flange part 46 provided to the outer surface 41b of the outer needle hub 26. Meanwhile, the inside mating claw 258 projecting from the inside of the protector 244 extends from the proximal end opening part 44 of the outer needle hub 26 to the inside thereof, and the insertion parts 186, 186 provided to the distal end of the first protector member 246 extend from the proximal end opening part 44 of the outer needle hub 26 to the inside thereof.

When the inner needle unit 272 and the outer needle unit 14 are attached, as described above, by the locking pieces 174, 174 and the contact retaining parts 254, 254 being in contact with each other, upward displacement of the lower elastic wall 260 is prevented. With this arrangement, the needle restricting part 242 of the second protector member 248 projects radially inward through the passage window 252, while being retained on the side of the inner needle 18 and at the position such that the needle restricting part 242 is not in contact with the inner needle 18, namely, is not pressed on the inner needle 18. Accordingly, in the present embodiment, the contact retaining parts 254, 254 constitute the block part that keeps the lower elastic wall 260 (the needle restricting part 242) serving as the urging part remote from the inner needle 18.

With the indwelling needle assembly 240 having the structure described above as well, by the inner needle 18 being pulled out to the proximal end side, as depicted in FIGS. 43 to 46, the large-diameter part 27 of the inner needle 18 and the rear wall 158 of the second protector member 248 are configured to be engaged with each other. In this state, by the inner needle 18 being pulled out further to the proximal end side, the second protector member 248 moves to the proximal end side together with the inner needle 18. Here, the first protector member 246 will not move due to the state of engagement with the outer needle hub 26, while the second protector member 248 is configured to move with respect to the first protector member 246 in the direction of approach in the needle axis direction.

Figure 48:
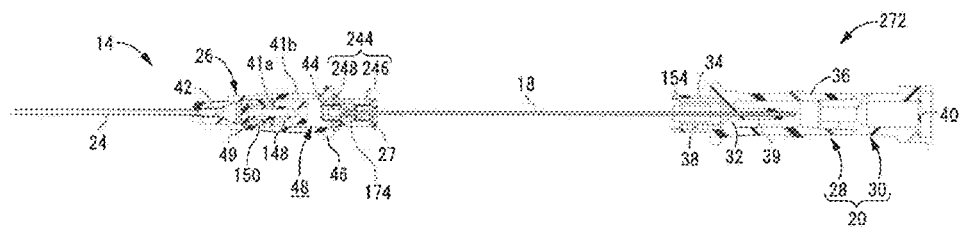
FIG. 48 is a cross sectional view taken along line 48-48 of FIG. 47.
Figure 49:
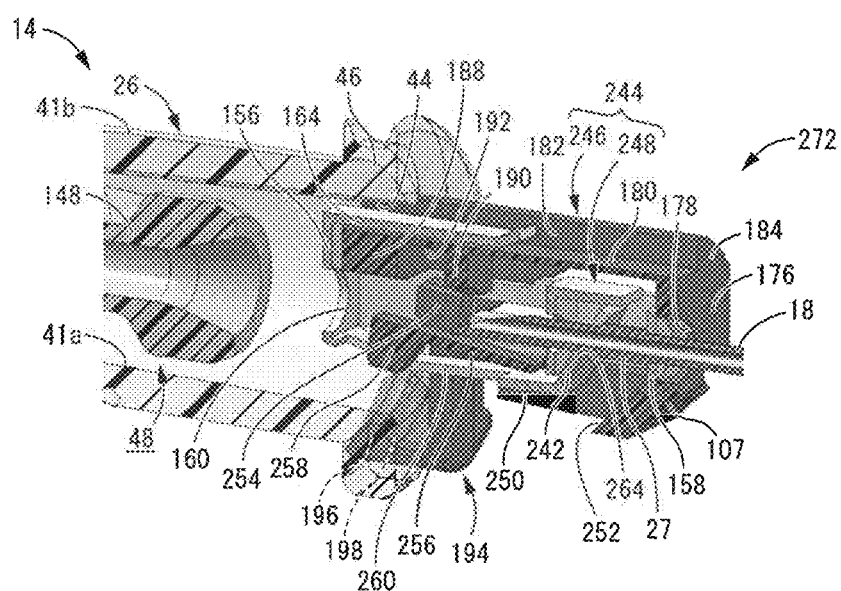
FIG. 49 is a view suitable for explaining a principal part of the indwelling needle assembly shown in FIG. 47, corresponding to FIG. 46.

Then, as depicted in FIGS. 47 to 49, by the second protector member 248 being moved with respect to the first protector member 246 to the proximal end side (the direction of approach in the needle axis direction), the locking pieces 174, 174 move with respect to the contact retaining parts 254, 254 to the proximal end side, so as to release engagement of the contact retaining parts 254, 254 with the locking pieces 174, 174. By so doing, the lower elastic wall 260 exhibits its elastic recovery action, and the lower elastic wall 260 (the needle restricting part 242) and the center wall 256 displace upward (to the inner needle 18 side), while the distal end portion of the inner needle 18 beyond the large-diameter part 27 is inserted in the notch 264 provided to the needle restricting part 242, so that the inner peripheral surface of the notch 264 comes into contact with the outer peripheral surface of the inner needle 18 from the side. At that time, the needle tip 16 of the inner needle 18 is covered by the protector 244, so that the needle tip 16 of the inner needle 18 is protected. Besides, the needle tip 16 of the inner needle 18 is positioned to the distal end side beyond the reinforcing distal end wall 268. Thus, even in the state where the needle restricting part 242 is moved, the inner needle 18 is inserted in a plurality of insertion holes 270, 162 of the respective insertion walls (the reinforcing distal end wall 268 and the rear wall 158), thereby limiting relative tilting of the inner needle 18 and the protector 244.

Here, the large-diameter part 27 of the inner needle 18 is engaged with the rear wall 158 of the second protector member 248, so that movement of the inner needle 18 to the proximal end side is limited. Besides, since the opening width dimension of the notch 264 is made smaller than the outside diameter dimension of the large-diameter part 27 of the inner needle 18, the large-diameter part 27 of the inner needle 18 is engaged with the needle restricting part 242, so that movement of the inner needle 18 to the distal end side is also limited. By so doing, with the inner needle 18 prevented from protruding from the protector 244, displacement of the inner needle 18 to the both sides in the needle axis direction is prevented. This will stably keep the protected state of the needle tip 16.

It should be appreciated that with the needle restricting part 242 moved and the inner needle 18 prevented from moving to the both sides in the needle axis direction in this way, when the inner needle 18 is pushed in to the distal end side, there is a risk that the needle restricting part 242 may deform or displace due to flexure so as to release the engagement of the needle restricting part 242 with the inner needle 18. Here, the second protector member 248 of the present embodiment includes the reinforcing distal end wall 268 or the like. When the needle restricting part 242 deforms or displaces to the distal end side, the reinforcing distal end wall 268 comes into contact with the needle restricting part 242, so as to limit deformation or displacement of the needle restricting part 242. Therefore, in the present embodiment, the reinforcing distal end wall 268 constitutes a reinforcing part for limiting deformation or displacement of the needle restricting part 242.

More specifically, if the angle formed by the axial direction of the inner needle 18 and the direction of extension of the needle restricting part 242 exceeds 90°, there may be an increased risk that the engagement of the needle restricting part 242 with the large-diameter part 27 of the inner needle 18 may be released. Thus, the indwelling needle assembly 240 has the structure in which the reinforcing distal end wall 268 and the needle restricting part 242 come into contact with each other before the angle formed by the axial direction of the inner needle 18 and the direction of extension of the needle restricting part 242 exceeds 90°. Also, in the present embodiment, in case the user should apply further excessive force, the proximal end of the center wall 256 is configured to be positioned on the distal end side in the needle axis direction as well as on the lower side (the needle restricting part 242 side) of the reinforcing part (the reinforcing distal end wall 268). Specifically, when the user applies further excessive force and the distal end side in the needle axis direction and the lower side of the reinforcing part 268 is flexed to the distal end side in the needle axis direction, the reinforcing part 268 is configured to come into contact with the proximal end of the center wall 256 at the moment before the engagement of the large-diameter part 27 of the inner needle 18 with the needle restricting part 242 gets released so as to limit further deformation of the reinforcing part 268, thereby more reliably restricting displacement of the inner needle 18 in the axial direction. In the initial state, the reinforcing part 268 and the needle restricting part 242, or the reinforcing part 268 and the proximal end of the center wall 256, or both of these combinations, may be configured to be in contact with each other. Besides, in the present embodiment, the portion for which deformation or displacement is to be limited by the reinforcing part 268 is defined by the needle restricting part 242 that projects toward the inner needle 18. However, such portion may be defined by the lower elastic wall 260 that is connected to the proximal end part of the needle restricting part 242. It would be acceptable as long as the portion for which deformation or displacement is to be limited by the reinforcing part 268 is defined by a component that moves toward the inner needle 18 in order to restrict displacement of the inner needle 18.

Moreover, by the center wall 256 being displaced upward, the inside mating claw 258 provided to the distal end of the center wall 256 becomes separated from the inner surface 41a of the outer needle hub 26. This will make a gap between the inside mating claw 258 and the outer needle hub 26, permitting downward displacement of the inner needle unit 272 with respect to the outer needle hub 26. Then, by the inner needle unit 272 being displaced downward with respect to the outer needle hub 26, engagement of the locking claws 196, 196 with the flange part 46 of the outer needle hub 26 will be released. This makes it possible to release the engagement of the protector 244 (the first protector member 246) with the outer needle hub 26.

With the indwelling needle assembly 240 of the present embodiment having the structure described above as well, the needle restricting part 242 for preventing protrusion of the inner needle 18 from the protector 244 is kept at the position remote from the inner needle 18 in the initial state. This makes it possible to minimize increase in sliding resistance during pulling out of the inner needle 18, thereby decreasing a risk of the outer needle 24 being pulled out together with the inner needle 18.

Additionally, the needle restricting part 242 of the indwelling needle assembly 240 of the present embodiment moves toward the inner needle 18 due to relative movement of one of the first protector member 246 and the second protector member 248. Thus, restricting force of the needle restricting part 242 will not be influenced by the inner needle 18. Therefore, even if the restricting force of the needle restricting part 242 is made larger, the friction between the inner needle 18 and the needle restricting part 242 will not be increased. Accordingly, it is possible to enhance the restricting force of the needle restricting part 242 and to decrease the sliding resistance due to the friction in a compatible manner.

Furthermore, since the first protector member 246 is a component made of resin, the weight can be decreased in comparison with the case where the first protector member 246 is a component made of metal. Also, since the second protector member 248 provided with the needle restricting part 242 is a component made of metal, the effect of preventing movement of the inner needle 18 can be more stably exhibited.

Next, FIGS. 50A and 50B depict an indwelling needle assembly 280 as a seventh embodiment of the present invention. A protector 282 that constitutes the indwelling needle assembly 280 of the present embodiment and serves as a safety mechanism part includes a clip 284 and an outside tube part 286 in which the clip 284 is inserted.

The outside tube part 286 includes a tubular part 287 that extends across the roughly entire length thereof in the needle axis direction. The tubular part 287 has at its distal end portion an outer-needle-hub engaging part 288 that extends from a part of the circumference of the tubular part 287 (the upper part in FIGS. 50A and 50B) to the distal end side. Besides, the outer-needle-hub engaging part 288 has a locking claw 290 that is integrally formed with its distal end and projects radially inward. The inside diameter dimension at the distal end opening of the tubular part 287 is made smaller than the inside diameter dimension at the proximal end opening part 44 of the outer needle hub 26. Accordingly, with the indwelling needle assembly 280 assembled, the inner surface of the tubular part 287 and the inner surface 41a of the outer needle hub 26 provide a step surface 291.

As shown in FIG. 50A, the clip 284 is formed by a single metal plate or the like being bent through press working or the like, for example, and includes a proximal end part 292 that extends in the vertical direction and a pair of urging parts 294a, 294b that respectively extend from the upper and lower ends of the proximal end part 292 while intersecting each other towards the distal end side. With this arrangement, the urging part 294a that extends while sloping downward from the upper end of the proximal end part 292 is subjected to an upward urging force, while the urging part 294b that extends while sloping upward from the lower end of the proximal end part 292 is subjected to a downward urging force. Moreover, the proximal end part 292 and the pair of urging parts 294a, 294b have respective passage holes that perforate their center portions in the needle axis direction, so that the inner needle 18 and a housing sleeve 296, which is externally placed about the inner needle 18 and serves as a block part, are inserted into the passage holes. The proximal end portion of the housing sleeve 296 constitutes a small-diameter part 296a serving as an inner-needle engaging part, while the distal end side from the axially medial portion of the housing sleeve 296 constitutes a large-diameter part 296b whose inside diameter and outside diameter are made larger than those of the small-diameter part 296a. On the outer circumferential surface of the housing sleeve 296, at the boundary between the small-diameter part 296a and the large-diameter part 296b, there is formed a tapered part 297 whose outside diameter dimension becomes gradually smaller toward the proximal end side.

Besides, the urging parts 294a, 294b have at their distal ends respective bent parts 298a, 298b that are bent to the inner needle 18 side. Specifically, the urging part 294a urged upward is bent at the bent part 298a to the inner needle 18 side, whose distal end constitutes a contact part 300a and is in contact with the housing sleeve 296 from below. Meanwhile, the urging part 294b urged downward is bent at the bent part 298b to the inner needle 18 side, whose distal end constitutes a contact part 300b and is in contact with the housing sleeve 296 from above. The contact parts 300a, 300b, which are the respective distal ends of the urging part 294a and the urging part 294b, are in contact with the housing sleeve 296 at the positions deviated in the needle axis direction.

With the inner needle 18 having such structure inserted, an inner needle unit 302 of the present embodiment is constituted, and by the inner needle unit 302 being inserted into the outer needle unit 14, the indwelling needle assembly 280 of the present embodiment is constituted. At that time, the locking claw 290 provided to the distal end of the outer-needle-hub engaging part 288 is engaged with the flange part 46 of the outer needle hub 26, while the bent parts 298a, 298b provided to the urging parts 294a, 294b of the clip 284 extend from the proximal end opening part 44 of the outer needle hub 26 to the inside of the outer needle hub 26. By so doing, displacement of the outer-needle-hub engaging part 288 in the direction of disengagement from the outer needle hub 26 is limited. Therefore, in the present embodiment, the bent part 298b of the urging part 294b, which is one of the urging parts 294a, 294b, constitutes the engaging-part opposing wall that is in opposition to the outer-needle-hub engaging part 288.

In this embodiment in particular, the inner peripheral surface of the tubular part 287 and the outer peripheral surface of the clip 284 viewed in the needle axis direction have generally rectangular shapes that correspond to each other. Thus, by the clip 284 being inserted into the tubular part 287, the clip 284 and the tubular part 287 are positioned with a slight gap therebetween in the peripheral direction, so that relative rotation is restricted due to their contact. With this arrangement, the engaging-part opposing wall (the bent part 298b of the urging part 294b) is stably positioned in opposition to the outer-needle-hub engaging part 288, thereby effectively preventing unexpected release of engagement of the outer-needle-hub engaging part 288 with the outer needle hub 26. Therefore, in the present embodiment, the inner peripheral surface of the tubular part 287 and the outer peripheral surface of the clip 284 constitute a rotation restricting part that restricts rotation of the outside tube part 286 relative to the urging parts 294a, 294b (the clip 284). It is acceptable as long as the inner peripheral surface of the tubular part 287 and the outer peripheral surface of the clip 284 have the corresponding shapes such that relative rotation will be restricted due to their contact in the peripheral direction. Thus, their shapes are not limited to a rectangular shape, and a polygonal shape, an oval shape can suitably be adopted. However, the tubular part 287 (the outer-needle-hub engaging part 288) and the clip 284 (the engaging-part opposing wall 298b) may be permitted relative rotation to the extent that their relative rotation will not generate such a gap between the inner surface 41a of the outer needle hub 26 and the engaging-part opposing wall 298b as to cause release of engagement of the outer-needle-hub engaging part 288 with the outer needle hub 26 through the gap.

Besides, the maximum remote distance between the bent parts 298a, 298b are made larger than the inside diameter dimension of the distal end opening of the tubular part 287. Thus, when the inner needle unit 302 and the outer needle unit 14 are attached as shown in FIG. 50A, the bent parts 298a, 298b are engaged with the step surface 291. With this arrangement, the clip 284 is prevented from being unexpectedly housed within the tubular part 287, thereby stably preventing displacement of the outer-needle-hub engaging part 288 and the engaging-part opposing wall 298b in the direction of disengagement from the outer needle hub 26.

With the indwelling needle assembly 280 of the present embodiment having the structure described above, as shown in FIG. 50B, by the inner needle 18 being pulled out to the proximal end side, the large-diameter part 27 of the inner needle 18 and the small-diameter part 296a of the housing sleeve 296 are engaged, so that the housing sleeve 296 is pulled out to the proximal end side together with the inner needle 18. Accordingly, contact of the housing sleeve 296 (the large-diameter part 296b) with the contact parts 300a, 300b of the clip 284 will be released, and the urging parts 294a, 294b each displace in the direction of approaching the inner needle 18. As a result, the distal end portions of the urging parts 294a, 294b protect the needle tip 16 of the inner needle 18, while the engaging-part opposing wall (the bent part 298b) displaces integrally with the urging part 294b. This will generate a gap between the engaging-part opposing wall 298b and the inner surface 41a of the outer needle hub 26, making it possible to release the engagement of the outer needle hub 26 with the outer-needle-hub engaging part 288 through the gap. Here, displacement of the housing sleeve 296 to the proximal end can be restricted by the tapered part 297 provided to the outer circumferential surface of the housing sleeve 296 and the proximal end part 292 of the clip 284 coming into contact with each other.

With the indwelling needle assembly 280 having the structure described above as well, the urging parts 294a, 294b (the contact parts 300a, 300b) are in contact with the housing sleeve 296, and will not directly slide with respect to the inner needle 18. Thus, in comparison with the case of directly sliding with respect to the inner needle 18, sliding resistance can be reduced. This makes it possible to decrease a risk of occurrence of troubles that the outer needle (24) is pulled out together with the inner needle 18.

In this embodiment in particular, relative rotation of the clip 284 and the outside tube part 286 is prevented. This makes it possible to decrease a risk that, for example, the clip 284 rotates with respect to the outside tube part 286 and generates a gap so as to release the engagement of the outer needle hub 26 with the outer-needle-hub engaging part 288 through the gap.

Figure 51A:
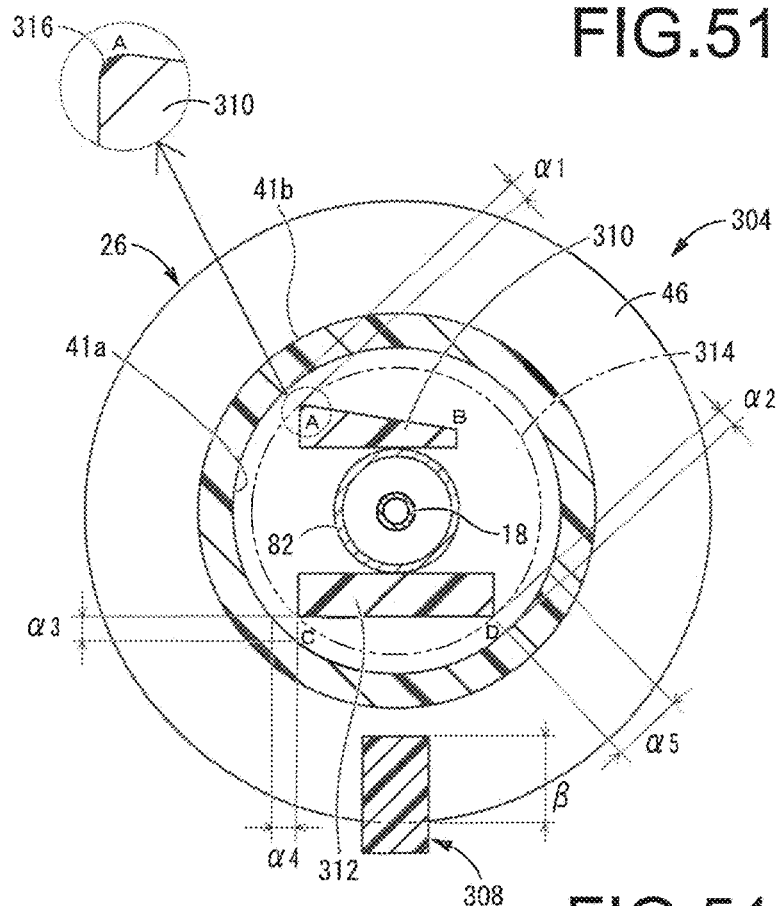
FIGS. 51A and 51B are views schematically showing transverse cross sections of indwelling needle assemblies as an eighth embodiment of the present invention.
Figure 51B:
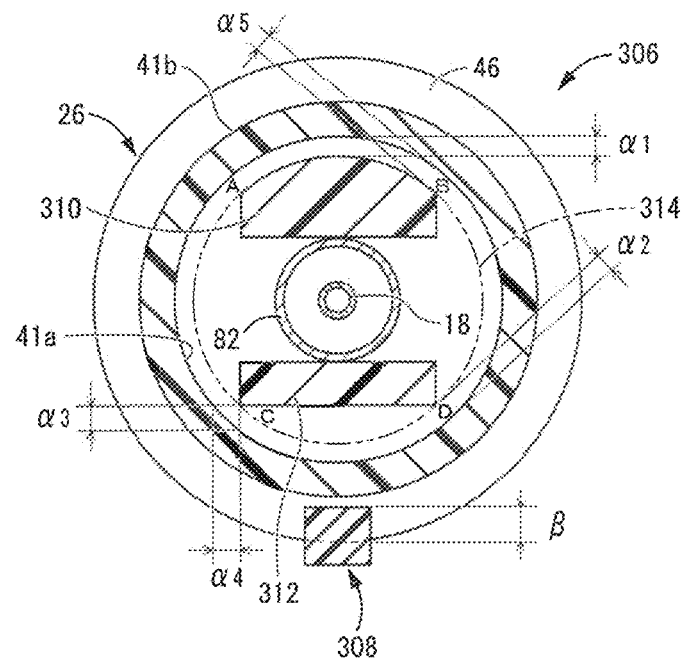

Next, FIGS. 51A and 51B schematically depict respective transverse cross sections of indwelling needle assemblies 304, 306 each according to an eighth embodiment of the present invention. In the present embodiment, the same as the seventh embodiment, the outer-needle-hub engaging part 308 engaged with the flange part 46, which serves as the engaging projection, of the outer needle hub 26 is a separate component from an urging part 310 and an urging-part opposing wall 312 urged toward the inner needle 18. The urging part 310 and the urging-part opposing wall 312 of the present embodiment correspond to the pair of urging parts 294a, 294b. Thus, it is possible to understand FIGS. 51A and 51B to be cross sectional views of the portion having the maximum contours (the portion positioned on the outermost circumference) at the proximal end opening part 44 of the outer needle hub 26. Meanwhile, the present embodiment does not include the rotation restricting part, so that the outer-needle-hub engaging part 308 is rotatable relative to the urging part 310 and the urging-part opposing wall 312 around the inner needle 18. Therefore, in the present embodiment, both the urging part 310 and the urging-part opposing wall 312 constitute the engaging-part opposing walls that are in opposition to the outer-needle-hub engaging part 308.

In the mode shown in FIG. 51A, the transverse cross sections of the urging part 310 and the urging-part opposing wall 312 each have a quadrangular shape. Where the vertexes on the outer peripheral side of the urging part 310 are defined as A and B, while the vertexes on the outer peripheral side of the urging-part opposing wall 312 are defined as C and D, distances a from the vertexes A, C, and D to the inner surface 41a of the outer needle hub 26 are roughly equal. Specifically, these vertexes A, C, and D are positioned on the circumference of a virtual circle 314 around the central axis of the inner needle 18, and the distance in each direction from the virtual circle 314 to the inner surface 41a of the outer needle hub 26 is α (α1 to α5). Therefore, if the engaging-part opposing walls 310, 312 displace, such displacement is limited by the engaging-part opposing walls 310, 312 coming into contact with the inner surface 41a outer needle hub 26. In the example shown in FIG. 51A, the maximum value of the amount of such displacement is α5. The vertex B may be positioned on the virtual circle 314, or alternatively may be positioned on inside or outside of the virtual circle 314.

Meanwhile, the outer-needle-hub engaging part 308 is engaged with the flange part 46 by the engagement margin β. Therefore, the amount of displacement of β is required for disengagement of the outer-needle-hub engaging part 308 radially outward from the flange part 46 (the engaging projection).

Here, the distances α (α1 to α5) from the vertexes A, C, and D to the inner surface 41a of the outer needle hub 26 are smaller than the engagement margin β of the outer-needle-hub engaging part 308 and the flange part 46. Therefore, in whichever position the urging part 310 or the urging-part opposing wall (the engaging-part opposing wall) 312 is located after relative rotation, the urging part 310 or the urging-part opposing wall 312 comes into contact with the inner surface 41a of the outer needle hub 26 before the outer-needle-hub engaging part 308 displaces by the amount of β in order to get disengaged radially outward from the flange part 46. Thus, even if the outer-needle-hub engaging part 308 is rotatable relative to the urging part 310 and the urging-part opposing wall (the engaging-part opposing wall) 312 around the inner needle 18, the engagement of the outer needle hub 26 with the outer-needle-hub engaging part 308 will be retained. This arrangement is able to decrease a risk that a gap is generated due to relative rotation of the engaging-part opposing wall with respect to the outer-needle-hub engaging part so as to release the engagement of the outer needle hub with the outer-needle-hub engaging part through the gap, as in the case shown in FIG. 29 of Patent Document 1 mentioned above.

In the case where the above-described mechanism is adopted, it is acceptable as long as three vertexes out of four vertexes (A, B, C, and D) on the outer peripheral side are on the circumference of the virtual circle 314 or on the outside of the virtual circle 314.

Besides, in the present embodiment, as depicted in an enlarged view at the upper left in FIG. 51A, which shows a part around the vertex A of the urging part (the engaging-part opposing wall) 310, the portions of the engaging-part opposing walls 310, 312 which are configured to be in contact with the inner surface 41a of the outer needle hub 26 are defined by a curving surface 316. This makes it possible to decrease a risk that the engaging-part opposing walls 310, 312 and the inner surface 41a of the outer needle hub 26 come into contact and rub against each other so that a fragment of the outer needle hub 26 may enter the blood vessel, for example.

Alternatively, as shown in FIG. 51B, the outer peripheral surface of at least one of the urging part 310 and the urging-part opposing wall 312 (the urging part 310 in FIG. 51B) may be defined by an arcuate surface that conforms to the virtual circle 314. In the case of the arcuate surface, it can be assumed that an infinite number of vertexes on the outer peripheral side exist on the arcuate surface in continuous fashion.

While the present invention has been described hereinabove in terms of certain embodiments, the invention shall not be construed as limited to the specific disclosures in the embodiments. It is also to be understood that the present invention may be embodied with various changes, modifications and improvements which may occur to those skilled in the art.

Figure 52:
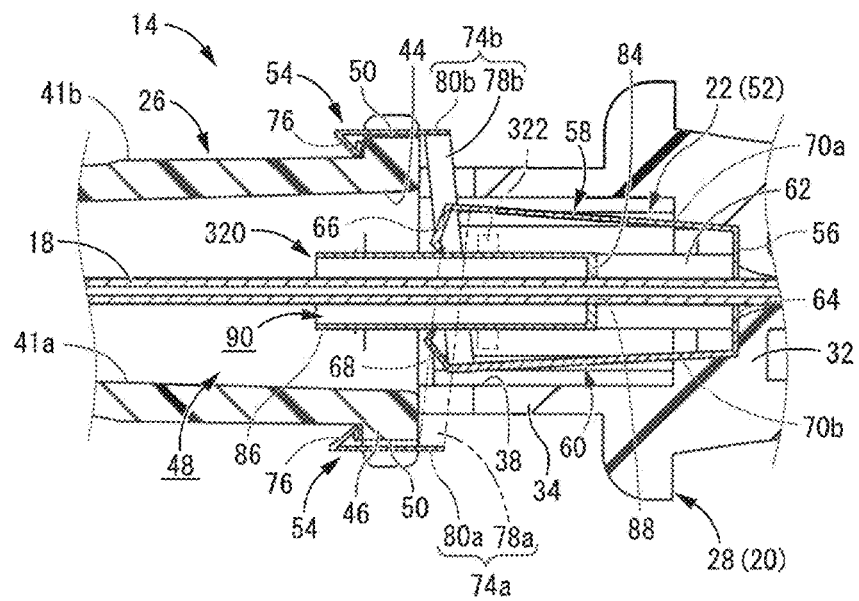
FIG. 52 is an enlarged vertical cross sectional view of a principal part of an indwelling needle assembly of the present invention, which is suitable for explaining another embodiment of a block part.

For example, while in the first, second, seventh, and eighth embodiments, the housing sleeve 82, 296 has an approximately round tubular shape with a bottom, it is acceptable as long as the housing sleeve is a tubular body like a roughly bottomed tubular shape including an engaging part configured to be engaged with the large-diameter part 27 of the inner needle 18. Besides, as indicated by the chain double-dashed line in FIG. 52, it is possible to adopt a housing sleeve 320 serving as a block part that includes at its axially medial portion an engaging convex part 322 projecting radially outward from the outer peripheral surface of the housing sleeve 320. By the engaging convex part 322 being provided further on the proximal end side than the contact parts 66, 68 provided to the protector 22, even if the housing sleeve 320 displaces to the distal end side, the engaging convex part 322 becomes engaged with the contact parts 66, 68, thereby preventing the housing sleeve 320 from falling out of the protector 22 to the distal end side. The engaging convex part 322 may be provided on the outer peripheral surface of the housing sleeve 320 about the entire periphery in the peripheral direction, for example, or may alternatively be provided so as to project in either one of the directions in which the contact parts 66, 68 are formed or extend (for example, either one of the upper and lower directions in FIG. 52). Also, whereas in FIG. 52, the engaging convex part 322 has a rectangular cross section, the cross section of the engaging convex part 322 may be a semicircular shape, or a polygonal shape such as a triangle, for example.

Figure 53:
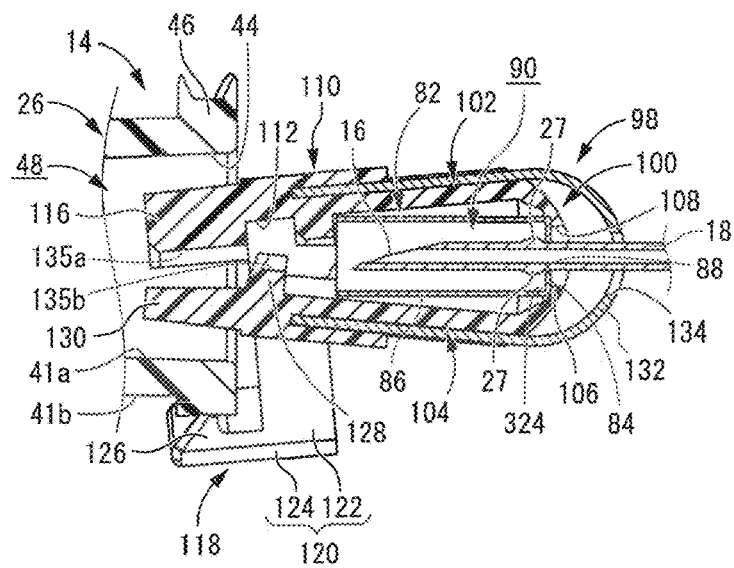
FIG. 53 is an enlarged vertical cross sectional view of a principal part of an indwelling needle assembly of the present invention, which is suitable for explaining another embodiment of a safety mechanism part.

Moreover, in the second embodiment, the traveling end of the housing sleeve 82 on the proximal end side is determined by coming into contact with the proximal end wall 106. However, as shown in FIG. 53, for example, the proximal end wall 106 may include a circular housing concave part 324 opening to the distal end side. The housing concave part 324 is provided by, for example, a semicircular concave part being formed on each of the upper and lower mating pieces 102, 104 and being combined with each other so as to be a circular concave part. The inside diameter dimension of the housing concave part 324 is made roughly equal to the outside diameter dimension of the housing sleeve 82. Thus, when the housing sleeve 82 moves to the proximal end side due to the inner needle 18 being pulled out, the housing sleeve 82 is configured to be fitted into the housing concave part 324. By providing such housing concave part 324, the traveling end of the housing sleeve 82 on the proximal end side can be determined by the bottom wall face of the housing concave part 324. Besides, since the distal end side of the housing sleeve 82 is in contact with and retained between the upper and lower mating pieces 102, 104 while the proximal end side of the housing sleeve 82 is fitted into and retained by the housing concave part 324, it is possible to more stably retain the housing sleeve 82 within the protector 98.

Also, in the first, second, and seventh embodiments, the protection part that covers the needle tip 16 of the inner needle 18 is in contact with the housing sleeve 82, 296 from the side, so as to constitute the contact parts 66, 68, 110, 128, 300a, and 300b that are in contact with the housing sleeve 82, 296. However, the contact part and the protection part may be separately provided from each other.

For example, it would also be acceptable that the protection part extends from the contact part to the further distal end side, and by the contact between the contact part and the block part being released and the contact part displacing in the direction of approaching the inner needle, the needle tip of the inner needle is protected by the protection part. The release of contact between the contact part and the block part may include the mode in which a concave part is provided on the outer circumferential surface of the block part and the contact part is inserted into the concave part. Specifically, it would also be possible that by the contact part being inserted in the concave part provided to the outer circumferential surface of the block part, the contact part displaces in the direction of approaching the inner needle, and the protection part extending from the contact part to the further distal end side protects the needle tip of the inner needle. Therefore, in the case where the block part 82, 296 is provided as described in the first, second, and seventh embodiments, the contact between the contact part and the block part may be released before the block part is completely housed within the protector.

Furthermore, the protector 22 of the first embodiment may include an urging means constituted by a separate component, as described in the second embodiment. However, the urging means shall not be limited to the plate shape piece 132 as described in the second embodiment.

Additionally, whereas in the preceding embodiments, the outer-needle-hub engaging part 54, 118, 194, 288, 308 is engaged with the flange part 46 provided to the proximal end opening part 44 of the outer needle hub 26, the present invention is not limited to such mode. Specifically, the flange part 46 is not essential, and for example, it would also be acceptable to provide the outer peripheral surface of the outer needle hub 26 with a concave part that corresponds to the locking claw of the outer-needle-hub engaging part. Of course, the engagement of the protector with the outer needle hub by means of the outer-needle-hub engaging part shall not be limited to the engagement by means of the concave/convex part as described above. For example, it would also be possible to adopt the mode in which no locking claw is provided, and the inner peripheral surface of the outer-needle-hub engaging part and the outer circumferential surface of the flange part 46 are engaged by means of friction.

Moreover, in the second embodiment, the positioning concave parts 135a, 135b for positioning the housing sleeve 82 are provided to the respective opposed faces of the upper and lower contact parts 110, 128. Similarly, in the first embodiment as well, the upper and lower contact parts 66, 68 may be provided with the positioning concave part as described above. Besides, in the first embodiment, the upper and lower contact parts 66, 68 are in contact with the housing sleeve 82 at the roughly same positions as each other in the axial direction. However, as in the second embodiment, the upper and lower contact parts 66, 68 may be in contact with the housing sleeve 82 at the deviated positions from each other in the axial direction.

Furthermore, in the first, second, and seventh embodiments, during engagement of the inner needle 18 with the housing sleeve 82, the distal end side from the large-diameter part 27 of the inner needle 18 is housed within the housing sleeve 82. However, the present invention shall not be limited to such mode. Specifically, it would also be possible to set the axial dimension from the large-diameter part of the inner needle to the needle tip larger than the axial dimension of the housing sleeve so that, during engagement of the inner needle with the housing sleeve, the needle tip of the inner needle protrudes from the housing sleeve. Even in such case, it is acceptable as long as the needle tip of the inner needle is protected by the protection part of the protector.

Additionally, in the preceding embodiments, one or two urging parts are provided, however, three or more urging parts may be provided. In such case, for example, it would be possible to adopt the mode in which each urging part includes one of the contact part and the urging part, or both of them, and at least one elastic piece includes the outer-needle-hub engaging part, or the like.

Besides, in the sixth embodiment, the protector may include a mating part configured to mate with each other due to movement of the needle restricting part towards the inner needle. Specifically, for example, by pulling out the inner needle 18 so as to move the second protector member 248 to the proximal end side, the contact of the locking pieces 174, 174 with the contact retaining parts 254, 254 is configured to be released, so that the center wall 256 and the contact retaining parts 254, 254 displace upward due to elastic recovery action of the lower elastic wall 260. At that time, it would be possible for the contact retaining parts 254, 254 to be inserted in the recess 192 provided between the guide projection 188 and the positioning projection 190. In such case, the contact retaining parts 254, 254 and the recess 192 constitute the mating part. Alternatively, it would also be acceptable that a concave part is provided to the reinforcing upper wall 266 so as to open downward, and the projecting distal end of the needle restricting part 242 is configured to be inserted in the concave part of the reinforcing upper wall 266 due to movement of the needle restricting part 242. In such case, the projecting distal end of the needle restricting part 242 and the concave part of the reinforcing upper wall 266 constitute the mating part. Owing to such mating part, it is possible to more stably maintain the shape of the protector 244 after movement of the needle restricting part 242. In addition, in the sixth embodiment, the needle restricting part 242 is configured to come into contact with only the distal end surface of the large-diameter part 27 of the inner needle 18. However, the needle restricting part may include a distal-end-side needle restricting part and a proximal-end-side needle restricting part in order to come into contact with both the distal end surface and the proximal end surface of the large-diameter part of the inner needle. In such case, it is preferable for the inner needle to be provided with a first inner-needle large-diameter part to be engaged with the needle restricting part, and a second inner-needle large-diameter part to be engaged with the proximal end wall of the second protector member. The second inner-needle large-diameter part can be simply fabricated by, for example, adopting a processing method by which the large-diameter part is not formed about the entire circumference in the circumferential direction (for example, crushing processing).

Moreover, in the sixth embodiment, the large-diameter part of the inner needle 18 to be engaged with the second protector member 248 and the large-diameter part of the inner needle 18 to be engaged with the needle restricting part 242 after movement of the needle restricting part 242 are constituted by the identical large-diameter part 27, but may be constituted by different large-diameter parts. Specifically, for example, it would be possible for the inner needle to be provided with a plurality of large-diameter parts separated by a prescribed distance in the needle axis direction, so that the large-diameter part on the proximal end side of the inner needle is configured to be engaged with the second protector member, while the large-diameter part on the distal end side is configured to be engaged with the needle restricting part. It would also be acceptable to form a concave part on the side surface of the inner needle so as to provide a large-diameter part having a larger outside diameter than that of the concave part at the edge of the concave part. By positioning the needle restricting part in the concave part, the relative movement of the inner needle and the needle tip protector may be restricted.

Furthermore, in the third, fourth, and sixth embodiments, movement of the inner needle 18 to the proximal end side is limited by the large-diameter part of the inner needle 18 being engaged with the rear wall 158 of the resin member 146 or the second protector member 248. However, the inner needle may alternatively be engaged with the vertical wall of the metal member or the first protector member so that it is possible to limit the movement of the inner needle to the proximal end by means of the vertical wall of the metal member or the first protector member by, for example, making the inside diameter dimension of the insertion hole of the rear wall larger than the outside diameter dimension of the large-diameter part of the inner needle as well as making the inside diameter dimension of the passage hole of the vertical wall smaller than the outside diameter dimension of the large-diameter part of the inner needle. In such case, it would be preferable to separately provide a mechanism for having the resin member or the second protector member undergo relative movement to the proximal end side due to pulling out of the inner needle.

Additionally, in the seventh embodiment, whereas the outer-needle-hub engaging part 288 is integrally formed with the outside tube part 286 so as to be in opposition to the engaging-part opposing wall (the bent part 298*b*), the present invention shall not be limited to such mode. For example, the protectors 22, 98, 142, 212, 226, 244 or the like of the first through sixth embodiments, respectively, which integrally include the outer-needle-hub engaging part and the engaging-part opposing wall, may be adopted as the clip to be inserted into the outside tube part. Besides, in the seventh embodiment, whereas the outer-needle-hub engaging part is integrally formed with the outside tube part while the engaging-part opposing wall is integrally formed with the clip, opposite combinations may also be acceptable. Specifically, it would also be possible that the outer-needle-hub engaging part is provided to the clip while the engaging-part opposing wall is provided to the outside tube part, and engagement of the outer needle hub by means of the outer-needle-hub engaging part may be released due to displacement of the clip.

It should be appreciated that the present invention is characterized in the structure of the protector for protecting the needle tip of the inner needle. Thus, the structures of the inner needle hub, the outer needle hub, the housing sleeve, or the like shall not be limited in any way.

Besides, modes described hereinbelow as to the indwelling needle assembly are each characterized in the structure of the housing sleeve, and can be recognized as an independent invention capable of solving a different problem from that of the present invention.

A first mode provides an indwelling needle assembly wherein an inner needle is inserted into an outer needle hub, a protector is externally mounted about the inner needle and is configured to protect a needle tip of the inner needle when the inner needle is pulled out of the outer needle hub, the indwelling needle assembly being characterized in that: a housing sleeve is externally placed about an inserted portion of the inner needle into the protector; and the protector includes at least one contact part that is in contact with the housing sleeve from a side.

A second mode provides the indwelling needle assembly according to the first mode, wherein the at least one contact part comprises a pair of contact parts, opposed faces of the contact parts include respective positioning concave parts, and the positioning concave parts clasp and retain the housing sleeve.

A third mode provides the indwelling needle assembly according to the second mode, wherein one of the contact parts and another of the contact parts are remote from each other in an axial direction such that the housing sleeve is clasped and retained by the positioning concave parts that are remote from each other in the axial direction.

A fourth mode provides the indwelling needle assembly according to any one of the first through third modes, wherein an engaging convex part projecting radially outward is provided to an outer peripheral surface of the housing sleeve further on a proximal end side than a contact portion with the contact part.

A fifth mode provides the indwelling needle assembly according to any one of the first through fourth modes, wherein the inner needle includes an engaging part whose diametrical dimension is made large, and an axial dimension of the housing sleeve is made larger than an axial dimension from the engaging part to the needle tip of the inner needle.

A sixth mode provides the indwelling needle assembly according to any one of the first through fifth modes, wherein an axial dimension of the housing sleeve is made smaller than an axial dimension of the protector.

A seventh mode provides the indwelling needle assembly according to any one of the first through sixth modes, wherein the at least one contact part comprises a pair of contact parts, and the protector includes a pair of side plate parts positioned in opposition on opposite sides of the housing sleeve in a direction which is orthogonal to a direction of opposition of the contact parts of the protector.

An eighth mode provides the indwelling needle assembly according to any one of the first through seventh modes, wherein at a proximal end portion of the protector, there is formed a housing concave part that positions a proximal end of the housing sleeve.

A ninth mode provides the indwelling needle assembly according to any one of the first through eighth modes, wherein an inside diameter dimension of the housing sleeve is made larger than an outside diameter dimension of the inner needle such that a gap is provided between the inner needle and the housing sleeve.

A tenth mode provides the indwelling needle assembly according to any one of the first through ninth modes, wherein the housing sleeve includes a bottom wall at a proximal end thereof, and the bottom wall includes a passage hole at a center thereof in which the inner needle is inserted.

KEYS TO SYMBOLS

10, 96, 140, 240, 280, 304, 306: indwelling needle assembly, 16: needle tip, 18: inner needle, 22, 98, 142, 212, 226, 244, 282: protector (safety mechanism part), 26: outer needle hub, 27: large-diameter part (convex part), 41a: inner surface, 41b: outer surface, 46: flange part (engaging projection), 54, 118, 288, 308: outer-needle-hub engaging part, 55: engaging-part opposing wall, 58: upper plate part (urging part), 60: lower plate part (urging part), 82, 296, 320: housing sleeve (block part), 84: bottom wall (inner-needle engaging part), 102: upper mating piece (urging part), 104: lower mating piece (urging-part opposing wall), 130: inside mating part (engaging-part opposing wall), 132: plate shape piece (plate spring), 133a, 133b: guiding groove, 158: rear wall (inner-needle engaging part), 164: upper elastic wall, 166, 218: lower elastic wall, 174: locking piece (block part), 182: upper concave groove (guiding groove), 194: connecting part (outer-needle-hub engaging part), 198: sloping part, 200: retaining wall (urging part), 202: distal end portion (engaging-part opposing wall), 208: lower concave groove (guiding groove), 222: locking convex part (engaging-part opposing wall), 234: middle wall (inner-needle engaging part), 242: needle restricting part, 254: contact retaining part (block part), 258: inside mating claw (engaging-part opposing wall), 260: lower elastic wall (urging part), 268: reinforcing distal end wall (reinforcing part), 284: clip (rotation restricting part), 286: outside tube part, 287: tubular part (rotation restricting part), 294a, 294b: urging part, 298b: bent part (engaging-part opposing wall), 310: urging part (engaging-part opposing wall), 312: urging-part opposing wall (engaging-part opposing wall), 316: curving surface

The invention claimed is:

1. An indwelling needle assembly comprising:
    an outer needle hub;
    an inner needle inserted into the outer needle hub; and
    a safety mechanism part externally mounted about the inner needle and is configured to protect a needle tip of the inner needle when the inner needle is pulled out of the outer needle hub,
    wherein the safety mechanism part includes at least one urging part urged in a direction of approaching the inner needle and a block part that is in contact with the urging part such that the urging part is kept remote from the inner needle, the block part includes an inner-needle engaging part that is engaged with the inner needle in an axial direction and a peripheral wall part on which the urging part is held in contact and being disposed about the inner needle with a radial space therebetween so that the peripheral wall part is radially spaced away from the inner needle, and the urging part and the block part are movable relative to each other in a lengthwise direction of the inner needle,
    the safety mechanism part further includes an outer-needle-hub engaging part that is engaged with an outer surface of the outer needle hub and an engaging-part opposing wall that is positioned in opposition to the outer-needle-hub engaging part and limits displacement of the outer needle hub in a direction of disengagement from the outer-needle-hub engaging part by being in contact with the outer needle hub, and relative rotation of the outer-needle-hub engaging part and the engaging-part opposing wall around the inner needle is restricted, at least one of the outer-needle-hub engaging part and the engaging-part opposing wall is configured to displace integrally with the urging part, and by the inner needle being pulled out of the outer needle hub, the block part engaged with the inner needle by the inner-needle engaging part is configured to move relative to the urging part to be in a state of non-contact, while the urging part is configured to displace in the direction of approaching the inner needle such that the needle tip of the inner needle is prevented from protruding from the safety mechanism part and engagement of the outer needle hub with the safety mechanism part is allowed to be released.

2. The indwelling needle assembly according to claim 1, wherein the engaging-part opposing wall extends to an inside of the outer needle hub.

3. The indwelling needle assembly according to claim 2, wherein the outer-needle-hub engaging part includes on an inner surface thereof a sloping part that gradually slopes in the direction of approaching the inner needle towards a distal end side in a needle axis direction.

4. The indwelling needle assembly according to claim 1, wherein the safety mechanism part further includes an outside tube part in which the urging part is inserted, and
one of the outer-needle-hub engaging part and the engaging-part opposing wall is integrally provided with the outside tube part, while another of the outer-needle-hub engaging part and the engaging-part opposing wall is configured to displace integrally with the urging part.

5. The indwelling needle assembly according to claim 4, wherein the outside tube part includes a rotation restricting part that restricts rotation relative to the urging part, and the rotation restricting part restricts the rotation of the outside tube part relative to the urging part while limiting disengagement of the outside tube part from the outer needle hub.

6. The indwelling needle assembly according to claim 1, wherein by the inner needle being pulled out of the outer needle hub, the urging part is configured to displace onto a needle axis of the inner needle such that the needle tip of the inner needle is prevented from protruding from the safety mechanism part.

7. An indwelling needle assembly comprising:
an outer needle hub;
an inner needle inserted into the outer needle hub; and
a safety mechanism part externally mounted about the inner needle and is configured to protect a needle tip of the inner needle when the inner needle is pulled out of the outer needle hub,
wherein the safety mechanism part includes at least one urging part urged in a direction of approaching the inner needle and a block part that is in contact with the urging part such that the urging part is kept remote from the inner needle, the block part includes an inner-needle engaging part that is engaged with the inner needle in an axial direction, and the urging part and the block part are movable relative to each other in a lengthwise direction of the inner needle,
the safety mechanism part further includes an outer-needle-hub engaging part that is engaged with an outer surface of the outer needle hub and an engaging-part opposing wall that is positioned in opposition to the outer-needle-hub engaging part and limits displacement of the outer needle hub in a direction of disengagement from the outer-needle-hub engaging part by being in contact with the outer needle hub, and relative rotation of the outer-needle-hub engaging part and the engaging-part opposing wall around the inner needle is restricted,
at least one of the outer-needle-hub engaging part and the engaging-part opposing wall is configured to displace integrally with the urging part,
by the inner needle being pulled out of the outer needle hub, the block part engaged with the inner needle by the inner-needle engaging part is configured to move relative to the urging part to be in a state of non-contact, while the urging part is configured to displace in the direction of approaching the inner needle such that the needle tip of the inner needle is prevented from protruding from the safety mechanism part and engagement of the outer needle hub with the safety mechanism part is allowed to be released,
the engaging-part opposing wall extends to an inside of the outer needle hub, and
the engaging-part opposing wall is made of synthetic resin.

8. An indwelling needle assembly comprising:
an outer needle hub;
an inner needle inserted into the outer needle hub; and
a safety mechanism part externally mounted about the inner needle and is configured to protect a needle tip of the inner needle when the inner needle is pulled out of the outer needle hub,
wherein the safety mechanism part includes at least one urging part urged in a direction of approaching the inner needle and a block part that is in contact with the urging part such that the urging part is kept remote from the inner needle, the block part includes an inner-needle engaging part that is engaged with the inner needle in an axial direction, and the urging part and the block part are movable relative to each other in a lengthwise direction of the inner needle,
the safety mechanism part further includes an outer-needle-hub engaging part that is engaged with an outer surface of the outer needle hub and an engaging-part opposing wall that is positioned in opposition to the outer-needle-hub engaging part and limits displacement of the outer needle hub in a direction of disengagement from the outer-needle-hub engaging part by being in contact with the outer needle hub, and relative rotation of the outer-needle-hub engaging part and the engaging-part opposing wall around the inner needle is restricted,
at least one of the outer-needle-hub engaging part and the engaging-part opposing wall is configured to displace integrally with the urging part,
by the inner needle being pulled out of the outer needle hub, the block part engaged with the inner needle by the inner-needle engaging part is configured to move relative to the urging part to be in a state of non-contact, while the urging part is configured to displace in the direction of approaching the inner needle such that the needle tip of the inner needle is prevented from protruding from the safety mechanism part and engagement of the outer needle hub with the safety mechanism part is allowed to be released, and
the engaging-part opposing wall is engaged with the outer surface of the outer needle hub.

9. The indwelling needle assembly according to claim 8, wherein the at least one urging part comprises a pair of urging parts provided in opposition to each other, the outer-needle-hub engaging part continuously extends from one of the urging parts positioned on an opposite side thereof with the inner needle being interposed therebetween, while the engaging-part opposing wall continuously extends from another of the urging parts positioned on an opposite side thereof with the inner needle being interposed therebetween, and by the pair of urging parts displacing in the direction of approaching the inner needle, the outer-needle-hub engaging part and the engaging-part opposing wall are configured to displace with respect to the outer needle hub in a direction of separation from the inner needle such that engagement of the outer-needle-hub engaging part and the engaging-part opposing wall with the outer surface of the outer needle hub is released.

10. An indwelling needle assembly comprising:

an outer needle hub;

an inner needle inserted into the outer needle hub;

a safety mechanism part externally mounted about the inner needle and is configured to protect a needle tip of the inner needle when the inner needle is pulled out of the outer needle hub; and a plate spring, wherein the safety mechanism part includes at least one urging part urged in a direction of approaching the inner needle and a block part that is in contact with the urging part such that the urging part is kept remote from the inner needle, the block part includes an inner-needle engaging part that is engaged with the inner needle in an axial direction, and the urging part and the block part are movable relative to each other in a lengthwise direction of the inner needle, the safety mechanism part further includes an outer-needle-hub engaging part that is engaged with an outer surface of the outer needle hub and an engaging-part opposing wall that is positioned in opposition to the outer-needle-hub engaging part and limits displacement of the outer needle hub in a direction of disengagement from the outer-needle-hub engaging part by being in contact with the outer needle hub, and relative rotation of the outer-needle-hub engaging part and the engaging-part opposing wall around the inner needle is restricted, at least one of the outer-needle-hub engaging part and the engaging-part opposing wall is configured to displace integrally with the urging part, by the inner needle being pulled out of the outer needle hub, the block part engaged with the inner needle by the inner-needle engaging part is configured to move relative to the urging part to be in a state of non-contact, while the urging part is configured to displace in the direction of approaching the inner needle such that the needle tip of the inner needle is prevented from protruding from the safety mechanism part and engagement of the outer needle hub with the safety mechanism part is allowed to be released, and the urging part is made of synthetic resin at least in a portion that is in contact with the block part, and the portion made of synthetic resin is urged by the plate spring in the direction of approaching the inner needle.

11. The indwelling needle assembly according to claim 10, wherein the safety mechanism part further includes an urging-part opposing wall that is provided integrally with the urging part and positioned mutually in opposition to the urging part with the inner needle being interposed therebetween, the plate spring is made of metal and has a U-letter shape, the urging part and the urging-part opposing wall have respective guiding grooves on outer surfaces thereof, and distal end portions of the plate spring, which are on an opening side of the plate spring, are inserted into the respective guiding grooves such that the urging part and the urging-part opposing wall are urged in the direction of approaching the inner needle.

12. The indwelling needle assembly according to claim 10, wherein the plate spring is made of metal and has a U-letter shape, and distal end portions of the plate spring extend toward a proximal end side in a needle axis direction.

13. An indwelling needle assembly comprising:

an outer needle hub;

an inner needle inserted into the outer needle hub; and a safety mechanism part externally mounted about the inner needle and is configured to protect a needle tip of the inner needle when the inner needle is pulled out of the outer needle hub, wherein the safety mechanism part includes at least one urging part urged in a direction of approaching the inner needle and a block part that is in contact with the urging part such that the urging part is kept remote from the inner needle, the block part includes an inner-needle engaging part that is engaged with the inner needle in an axial direction, and the urging part and the block part are movable relative to each other in a lengthwise direction of the inner needle, the safety mechanism part further includes an outer-needle-hub engaging part that is engaged with an outer surface of the outer needle hub and an engaging-part opposing wall that is positioned in opposition to the outer-needle-hub engaging part and limits displacement of the outer needle hub in a direction of disengagement from the outer-needle-hub engaging part by being in contact with the outer needle hub, and relative rotation of the outer-needle-hub engaging part and the engaging-part opposing wall around the inner needle is restricted, at least one of the outer-needle-hub engaging part and the engaging-part opposing wall is configured to displace integrally with the urging part, by the inner needle being pulled out of the outer needle hub, the block part engaged with the inner needle by the inner-needle engaging part is configured to move relative to the urging part to be in a state of non-contact, while the urging part is configured to displace in the direction of approaching the inner needle such that the needle tip of the inner needle is prevented from protruding from the safety mechanism part and engagement of the outer needle hub with the safety mechanism part is allowed to be released, and the block part has a plate shape.

14. An indwelling needle assembly comprising:

an outer needle hub;

an inner needle inserted into the outer needle hub; and a safety mechanism part externally mounted about the inner needle and is configured to protect a needle tip of the inner needle when the inner needle is pulled out of the outer needle hub, wherein the safety mechanism part includes at least one urging part urged in a direction of approaching the inner needle and a block part that is in contact with the urging part such that the urging part is kept remote from the inner needle, the block part includes an inner-needle engaging part that is engaged with the inner needle in an axial direction, and the urging part and the block part are movable relative to each other in a lengthwise direction of the inner needle, the safety mechanism part further includes an outer-needle-hub engaging part that is engaged with an outer surface of the outer needle hub and an engaging-part opposing wall that is positioned in opposition to the outer-needle-hub engaging part and limits displacement of the outer needle hub in a direction of disengagement from the outer-needle-hub engaging part by being in contact with the outer needle hub, and relative rotation of the outer-needle-hub engaging part and the engaging-part opposing wall around the inner needle is restricted, at least one of the outer-needle-hub engaging part and the engaging-part opposing wall is configured to displace integrally with the urging part, by the inner needle being pulled out of the outer needle hub, the block part engaged with the inner needle by the inner-needle engaging part is configured to move relative to the urging part to be in a state of non-contact, while the urging part is configured to displace in the direction of approaching the inner needle such that the needle tip of the inner needle is prevented from protruding from the safety mechanism part and engagement of the outer needle hub with the safety mechanism part is allowed to be released, and the urging part includes a needle restricting part that is configured to come into contact with a side surface of the inner needle, and by the inner needle being pulled out of the outer needle hub, the needle restricting part is configured to come into contact with the side surface of the inner needle such that the needle tip of the inner needle is prevented from protruding from the safety mechanism part.

15. The indwelling needle assembly according to claim 14, wherein the needle restricting part is configured to be engaged with either one of a convex part and a concave part formed on an outer circumferential surface of the inner needle by the inner needle being pulled out of the outer needle hub.

16. The indwelling needle assembly according to claim 14, wherein the safety mechanism part further includes a reinforcing part that is configured to limit flexure of the needle restricting part in a position to which the urging part displaces in the direction of approaching the inner needle.

17. An indwelling needle assembly comprising:
an outer needle hub;
an inner needle inserted into the outer needle hub; and
a safety mechanism part is externally mounted about the inner needle and is configured to protect a needle tip of the inner needle when the inner needle is pulled out of the outer needle hub, wherein the safety mechanism part includes an urging part urged in a direction of approaching the inner needle and a block part that is in contact with the urging part such that the urging part is kept remote from the inner needle, the block part includes an inner-needle engaging part that is engaged with the inner needle in an axial direction and a peripheral wall part on which the urging part is held in contact and being disposed about the inner needle with a radial space therebetween so that the peripheral wall part is radially spaced away from the inner needle, and the urging part and the block part are movable relative to each other in a lengthwise direction of the inner needle, the outer needle hub is provided with an engaging projection on an outer surface thereof, the safety mechanism part further includes an outer-needle-hub engaging part that is engaged with the engaging projection and an engaging-part opposing wall that limits disengaging displacement of the outer-needle-hub engaging part radially outward from the engaging projection by coming into contact with an inner surface of the outer needle hub, an amount of displacement to be limited by the engaging-part opposing wall coming into contact with the inner surface of the outer needle hub is set so as not to reach an amount of displacement required for disengagement of the outer-needle-hub engaging part radially outward from the engaging projection in every axis-perpendicular direction of the outer needle hub, at least one of the outer-needle-hub engaging part and the engaging-part opposing wall is configured to displace integrally with the urging part, and by the inner needle being pulled out of the outer needle hub, the block part engaged with the inner needle by the inner-needle engaging part is configured to move relative to the urging part to be in a state of non-contact, while the urging part is configured to displace in the direction of approaching the inner needle such that the needle tip of the inner needle is prevented from protruding from the safety mechanism part and engagement of the outer needle hub with the safety mechanism part is allowed to be released.

18. The indwelling needle assembly according to claim 17, wherein the engaging-part opposing wall has a curving surface shape in a portion that is configured to come into contact with the inner surface of the outer needle hub.

* * * * *